US012742174B2

(12) United States Patent
Bovet et al.

(10) Patent No.: US 12,742,174 B2
(45) Date of Patent: Sep. 22, 2026

(54) **MODULATING ALKALOID PROFILES IN *NICOTIANA TABACUM***

(71) Applicant: Philip Morris Products S.A., Neuchatel (CH)

(72) Inventors: Lucien Bovet, Neuchatel (CH); Aurore Hilfiker, Neuchatel (CH); Kacper Piotr Kaminski, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 120 days.

(21) Appl. No.: 18/688,480

(22) PCT Filed: Sep. 1, 2022

(86) PCT No.: PCT/EP2022/074368
§ 371 (c)(1),
(2) Date: Mar. 1, 2024

(87) PCT Pub. No.: WO2023/036691
PCT Pub. Date: Mar. 16, 2023

(65) Prior Publication Data

US 2024/0368615 A1 Nov. 7, 2024

(30) Foreign Application Priority Data

Sep. 10, 2021 (EP) .................................... 21196023

(51) Int. Cl.
*C12N 15/82* (2006.01)
*C12N 9/88* (2006.01)

(52) U.S. Cl.
CPC ........... *C12N 15/8243* (2013.01); *C12N 9/88* (2013.01); *C12Y 401/01019* (2013.01)

(58) Field of Classification Search
None
See application file for complete search history.

(56) References Cited

U.S. PATENT DOCUMENTS

| | | | | |
|---|---|---|---|---|
| 10,405,571 | B2 * | 9/2019 | Adams | A24D 1/045 |
| 2007/0034220 | A1 | 2/2007 | Pandolfino | |
| 2015/0007364 | A1 | 1/2015 | Maor et al. | |
| 2018/0153207 | A1 | 6/2018 | Pandolfino | |
| 2019/0085354 | A1 | 3/2019 | Maor et al. | |

FOREIGN PATENT DOCUMENTS

| | | | |
|---|---|---|---|
| WO | WO 00/67558 | A1 | 11/2000 |
| WO | WO 2005/018307 | A1 | 3/2005 |
| WO | WO 2013/118120 | A2 | 8/2013 |

OTHER PUBLICATIONS

Bortolotti et al, 2004, Physiol. Plantarum 120 (1), 84-92.*
Burtin et al, 1997, Biochem. J., 325, 331-337.*
Martinez et al, 2020, Planta, 251(92), 1-14.*
Sisson, 1990, Beitrage zur Tabakforschung International, 14(6), 327-339.*
Sierro et al, 2013, Genome Biol. 14:R60.1-R60.17.*
International Search Report & Written Opinion mailed on Dec. 7, 2022 in PCT/EP2022/074368 filed on Sep. 1, 2022 (17 pages).
European Search Report dated Feb. 8, 2022, 2022 in EP Application 21196023.2 filed on Sep. 10, 2021, (9 pages.
Anonymous et al: "TSA: Nicotiana benthamiana isotig04028.Nb_leaf mRNA sequence—Nucleotide—NCBI", Sep. 30, 2012 (Sep. 30, 2012), XP055888501, 2 pages.
Zenkner Fernanda Fleig et al: "Nicotine Biosynthesis in Nicotiana: A Metabolic Overview", Tobacco Science, 56, Apr. 1, 2019 (Apr. 1, 2019), pp. 1-9, XP055888894.
Bunsupa S. et al., Molecular Evolution and Functional Characterization of a Bifunctional Decarboxylase Involved in Lycopodium Alkaloid Biosynthesis. Plant Physiol. Aug. 2016:171(4):2432-44. doi: 10.1104/pp. 16.00639. Epub Jun. 14, 2016. PMID: 27303024; PMCID: PMC4972286.
DeBoer KD et al., RNAi-mediated down-regulation of ornithine decarboxylase (ODC) leads to reduced nicotine and increased anatabine levels in transgenic *Nicotiana tabacum* L. Phytochemistry. Apr. 2011;72(4-5):344-55. doi: 10.1016/j.phytochem.2010.12.012. Epub Jan. 11, 2011. PMID: 21232776.
Furer V. et al., *Nicotiana glauca* (tree tobacco) intoxication—two cases in one family. J Med Toxicol. Mar. 2011;7(1):47-51. doi: 10.1007/s13181-010-0102-x. PMID: 20652661; PMCID: PMC3614112.
Kaminski KP et al., Alkaloid chemophenetics and transcriptomics of the *Nicotiana* genus. Phytochemistry. Sep. 2020; 177:112424. doi: 10.1016/j.phytochem.2020.112424. Epub Jun. 8, 2020. PMID: 32526514.
Keeler RF et al., Teratogenicity and toxicity of wild tree tobacco, *Nicotiana glauca* in sheep. Cornell Vet. Jan. 1984;74(1):50-9. PMID: 6705539, https://babel.hathitrust.org/cgi/pt?id=uc1.b4179410&seq=58.
Lee YS et al., Identification of essential active-site residues in ornithine decarboxylase of *Nicotiana glutinosa* decarboxylating both L-ornithine and L-lysine. Biochem J. Dec. 15, 2001;360(Pt 3):657-65. doi: 10.1042/0264-6021:3600657. PMID: 11736657; PMCID: PMC1222270.
Tiburcio AF et al., Effect of polyamine biosynthetic inhibitors on alkaloids and organogenesis in tobacco callus cultures. Plant Cell Tissue Organ Cult. 1987; 9:111-20. doi: 10.1007/BF00044246. PMID: 11539719.
Welch KD et al., A study on embryonic death in goats due to *Nicotiana glauca* ingestion. Toxicon. Nov. 2014; 90:64-9. doi: 10.1016/j.toxicon.2014.07.020. Epub Aug. 7, 2014. PMID: 25108148 https://pubmed.ncbi.nlm.nih.gov/25108148/.

(Continued)

*Primary Examiner* — Jason Deveau Rosen
(74) *Attorney, Agent, or Firm* — Oblon, McClelland, Maier & Neustadt, L.L.P.

(57) ABSTRACT

A non-naturally occurring or transgenic *Nicotiana tabacum* plant cell encompassing a heterologous polynucleotide that encodes arginine decarboxylase (ADC) and a method for producing such a cell are provided. Transgenic *Nicotiana tabacum* plants, plant parts, and plant tissues including these cells and plant materials and biomass produced by these cells and plants cells forming such a plant are provided. Materials produced by this plant, including plant leaves, flowers, seeds, extracts, and other plant biomass obtained from this plant including materials that have altered alkaloid levels are disclosed. Also provided are smoking articles including various tobacco products containing these materials.

18 Claims, 4 Drawing Sheets

Specification includes a Sequence Listing.

(56) References Cited

OTHER PUBLICATIONS

Sanchez-Rangel D. et al., Simultaneous Silencing of Two Arginine Decarboxylase Genes Alters Development in *Arabidopsis*. Front Plant Sci. Mar. 14, 2016; 7:300. doi: 10.3389/fpls.2016.00300. PMID: 27014322; PMCID: PMC4789552.

Masgrau C. et al., Inducible overexpression of oat arginine decarboxylase in transgenic tobacco plants. Plant J. Mar. 1997;11(3):465-73. doi: 10.1046/j.1365-313x.1997.11030465. x. PMID: 9107036.

Burtin D. et al., Overexpression of arginine decarboxylase in transgenic plants. Biochem J. Jul. 15, 1997;325 ( Pt 2)(Pt 2):331-7. doi: 10.1042/bj3250331. PMID: 9230111; PMCID: PMC1218565. https://pmc.ncbi.nlm.nih.gov/articles/PMC1218565/pdf/9230111.pdf.

Chintapakorn Y. et al., Antisense-mediated reduction in ADC activity causes minor alterations in the alkaloid profile of cultured hairy roots and regenerated transgenic plants of Nicotiana tabacum. Phytochemistry. Oct. 2007;68(19):2465-79. doi: 10.1016/j.phytochem.2007.05.025. Epub Jul. 5, 2007. Erratum in: Phytochemistry. Jan. 2008:69(1):288. PMID: 17612583.

Urano K. et al., *Arabidopsis* ADC genes involved in polyamine biosynthesis are essential for seed development. FEBS Lett. Feb. 28, 2005;579(6):1557-64. doi: 10.1016/j.febslet.2005.01.048. PMID: 15733873. https://febs.onlinelibrary.wiley.com/doi/epdf/10.1016/j.febslet.2005.01.048.

Noury M. et al., A transgenic rice cell lineage expressing the oat arginine decarboxylase (adc) cDNA constitutively accumulates putrescine in callus and seeds but not in vegetative tissues. Plant Mol Biol. Jul. 2000;43(4):537-44. doi: 10.1023/a:1006480304879. PMID: 11052205. https://pubmed.ncbi.nlm.nih.gov/11052205/.

* cited by examiner

MODULATING ALKALOID PROFILES IN *NICOTIANA TABACUM*

REFERENCE TO A SEQUENCE LISTING

In accordance with 37 CFR § 1.833-1835 and 37 CFR § 1.77 (b) (5), the specification makes reference to a Sequence Listing submitted electronically as a .xml file named "551110US_ST26.xml". The .xml file was generated on Jan. 26, 2024 and is 39,618 bytes in size. The entire contents of the Sequence Listing are hereby incorporated by reference.

FIELD OF THE INVENTION

The present invention relates to *Nicotiana tabacum* plant cells, plants or parts thereof with altered levels of one or more alkaloids, and methods of producing said plant cells, plants or parts thereof. The present invention also relates to plant material with altered levels of one or more alkaloids and tobacco products or smoking articles incorporating the plant material. The present invention also relates to methods of producing alkaloids, suitably anabasine and anatabine.

BACKGROUND OF THE INVENTION

The presence of alkaloids is a characteristic trait of the *Nicotiana* genus. Alkaloids are thought to have evolved as a chemical defence against predators (DeBoer et al., 2013. *Phytochemistry,* 86:21-28). Generally, four alkaloids constitute the majority of the alkaloid pool in most *Nicotiana* species namely, nicotine, nornicotine, anabasine, and anatabine (DeBoer et al., 2013 supra). The level and pattern of each alkaloid varies depending on the *Nicotiana* species (Sisson and Severson (1990) Beiträge zur Tabakforschung International, 14 (6): 327-339).

The pathways involved in alkaloid production in *Nicotiana* species have not yet been fully elucidated. However, it is understood that putrescine is the key reactant to generate the pyrrolidine ring of nicotine. In most plants, including *Nicotiana* species, putrescine is derived directly from the amino acid ornithine. Ornithine can be converted into putrescine by one of two pathways. The first pathway is the direct pathway, where ornithine decarboxylase (ODC) catalyses the conversion of ornithine into putrescine. The second pathway involves the indirect production of putrescine via a three-enzymatic step process. The first step is the conversion of arginine into agmatine by arginine decarboxylase (ADC). This is followed by the conversion of agmatine into N-carbamoyl putresceine by agmatine iminohydrolase (agmatine deiminase or AIC). Finally, the N-carbamoyl putrescine is converted into putrescine by N-carbamoyl putrescine amidohydrolase (DeBoer et al., 2013 supra). Alternatively, nornicotine is a metabolite formed by demethylation of nicotine by a small family of closely related cytochrome P450 enzymes collectively known as nicotine N-demethylases which are encoded by CYP82E genes (DeBoer et al., 2013 supra). The pathways leading to the production of anabasine and anatabine appear to involve the presence of cadaverine and nicotinic acid, respectively. Modulating alkaloid levels in *Nicotiana* is desirable for a variety of reasons.

There has been a longstanding view that cigarettes with reduced levels of nicotine could reduce nicotine dependence, thus reducing daily consumption, reducing the uptake of smoking and increasing attempts at quitting and increasing successful quitting (Benowitz and 1a Henningfield, 1994. *The New England Journal of Medicine,* 331 (2): 123-125). This could reduce tobacco exposure and levels of smoking-associated morbidity or mortality.

Reducing levels of nornicotine may be desirable as nornicotine is associated with various negative health effects-such as aberrant protein glycation in the cell (Dickerson and Janda, 2002. *PNAS,* 99 (23): 15084-15088). Nornicotine is also known to react with nitrosating agents to form nitrosamines-such as N'-nitrosonoricotine (NNN) and 4-(methylnitrosamino)-1-(3-pyridyl)-1-butanone (NNK) which are carcinogenic in humans and linked to various cancers. The alkaloid content of cigarettes has also been linked to the sensory experience of smoking. In particular, alkaloids are bitter compounds, so altering the total alkaloid content can alter the taste, impact, softness and aroma of the tobacco and tobacco smoke (Lin et al., 2016. *Regulatory Toxicology and Pharmacology,* 75:27-34). Therefore, modulating the levels of alkaloids may be desirable in commercial *Nicotiana* varieties to produce tobacco products or smoking articles with different flavours, aromas and sensory experiences.

Increasing the levels of alkaloids in plants may be desirable to allow isolation of these alkaloids from the plant for other uses. For example, alkaloids can be used as insecticides, and antimicrobials. Similarly, alkaloids, particularly anatabine and anabasine, have anti-inflammatory properties and have been found to be useful in the treatment or prevention of various inflammatory diseases.

Previous studies have attempted to modulate the levels of alkaloids in *Nicotiana tabacum* by targeting the genes involved in the alkaloid synthesis pathways. In particular, ODC appears to be the most important enzyme in modulating alkaloid levels in *N. tabacum*. Downregulation of ODC in *N. tabacum* using RNAi has been found to result in reduced nicotine content and an increased anatabine content (DeBoer et al., 2011. *Phytochemistry,* 72:344-355, DeBoer et al., 2013 supra, Dalton et al., 2016. *Journal of Experimental Botany,* 67 (11): 3367-3381), whereas downregulation of ADC activity in transgenic *N. tabacum* plants did not result in any significant changes to the alkaloid content compared to control lines suggesting that ODC is more important than ADC in nicotine biosynthesis. Similarly, RNA interference of the endogenous ADC genes in *N. tabacum* did not result in any significant changes of nicotine content compared to control lines throughout most of the culture cycle (Chintapakorn and Hamill, 2007. *Phytochemistry,* 68:2465-2479) suggesting that ADC is not of primary importance in nicotine synthesis. In a more recent study by Martinez et al. (2020) Planta 251, 92, RNA interference of ODC, ADC and aspartate oxidase in *Nicotiana tabacum* was reported to result in viable plants with a lower nicotine content. Martinez et al. (2020) contemplate that multiple different biosynthetic pathways catalysed by a variety of different enzymes may feed substrate towards nicotine biosynthesis in commercial cultivars of tobacco.

There is a continuing need in the art for commercially viable *N. tabacum* plants with modified levels of one or more alkaloids. The present invention seeks to address this and other needs.

SUMMARY OF THE INVENTION

The present inventors have determined that expression of heterologous ADCs in a *Nicotiana tabacum* host can result in altered levels of alkaloids therein. Advantageously, the altered levels of alkaloids are observed without any significant impact on the growth phenotype of the *Nicotiana tabacum* host, which is important in the context of the commercial production of tobacco. When ADC1 from *Nico-*

*tiana glauca* (NgADC1) was expressed in a *Nicotiana tabacum* host, there was a significant reduction of nicotine and nornicotine levels with a slight, but non-significant increase in anabasine and anatabine levels as compared to a control. When ADC2 from *Nicotiana glauca* (NgADC2) was expressed in a *Nicotiana tabacum* host, there was a significant reduction in nicotine and nornicotine but there was no significant impact on anabasine or anatabine levels as compared to a control. The total amount of nicotine, nornicotine, anabasine and anatabine was lower when ADC1 or ADC2 from *Nicotiana glauca* was expressed in a *Nicotiana tabacum* host as compared to the control. These are surprising results in view of Martinez et al. (2020) who demonstrate that RNA interference of ADC in *Nicotiana tabacum* results in viable plants with a lower nicotine content. In other words, they demonstrate that reduced expression of ADC results in lower nicotine content. Accordingly, the skilled person would expect that increased expression of ADC in *Nicotiana tabacum* would result in higher nicotine content. However, this is not the case when ADC1 or ADC2 from *Nicotiana glauca* (NgADC1 or NgADC2) is expressed in a *Nicotiana tabacum* host as there was a significant reduction in nicotine (and also nornicotine).

When ADC from *Nicotiana debneyi* (NdADC1) was expressed in a *Nicotiana tabacum* host, there was a significant increase in nicotine, anabasine and anatabine with a slight but non-significant increase in nornicotine levels. The total amount of nicotine, nornicotine, anabasine and anatabine was higher when ADC1 from *Nicotiana debneyi* was expressed in a *Nicotiana tabacum* host as compared to the control. It is highly unexpected that the impact on the alkaloids using *Nicotiana debneyi* ADC would be the opposite to what was found when using *Nicotiana glauca* ADC. It is also highly unexpected that anabasine and anatabine levels are increased.

The present results unexpectedly suggest that ADCs play different roles in different *Nicotiana* species. For example, based on these results, and without being bound by any particular theory, expressing *Nicotiana glauca* ADC may mask the activity of the endogenous *Nicotiana tabacum* ADC. In other words, by the fact that *Nicotiana tabacum* ADC is less performant than *Nicotiana glauca* ADC, it results in less nicotine accumulation in leaves.

Accordingly, expressing *Nicotiana glauca* ADC in a *Nicotiana tabacum* host is a particularly effective route for reducing nicotine and nornicotine accumulation in *Nicotiana tabacum* and without any significant impact on the growth phenotype of the *Nicotiana tabacum* host. On the other hand, expressing *Nicotiana debneyi* ADC in a *Nicotiana tabacum* host without any significant impact on the growth phenotype of the *Nicotiana tabacum* host is a particularly effective route for increasing nicotine, anatabine and anabasine levels, which is especially useful for the production of each of these alkaloids in *Nicotiana tabacum*.

In a first aspect, there is disclosed a non-naturally occurring or transgenic host *Nicotiana tabacum* plant cell comprising at least one of: (i) a heterologous polynucleotide comprising, consisting, or consisting essentially of a polynucleotide sequence having at least 96% sequence identity to SEQ ID NO: 1, or at least 97% sequence identity to SEQ ID NO: 3; or (ii) a heterologous polypeptide encoded by the polynucleotide set forth in (i); or (iii) a heterologous polypeptide comprising, consisting or consisting essentially of a polypeptide sequence having at least 97% sequence identity to SEQ ID NO: 2, at least 97.5% sequence identity to SEQ ID NO: 4; or (iv) a construct, vector or expression vector comprising the heterologous polynucleotide of (i); or (v) a heterologous polynucleotide comprising, consisting, or consisting essentially of a polynucleotide sequence having at least 96.5% sequence identity to SEQ ID NO: 5; or (vi) a heterologous polypeptide encoded by the polynucleotide set forth in (v); or (vii) a heterologous polypeptide comprising, consisting or consisting essentially of a polypeptide sequence having at least 97.5% sequence identity to SEQ ID NO: 6; or (viii) a construct, vector or expression vector comprising the heterologous polynucleotide of (v), wherein said heterologous polynucleotide or polypeptide encodes an arginine decarboxylase (ADC).

Suitably, the expression of the at least one heterologous polynucleotide or heterologous polypeptide encoding the ADC alters the levels of one or more alkaloids in the host *Nicotiana tabacum* plant cell as compared to a control *Nicotiana tabacum* plant cell not comprising the at least one heterologous polynucleotide or heterologous polypeptide, suitably, wherein the one or more alkaloids are selected from: nicotine, nornicotine, anabasine or anatabine.

Suitably, the at least one heterologous polynucleotide or polypeptide encoding the ADC is from *Nicotiana glauca* or *Nicotiana debneyi*.

Suitably, the levels of nicotine and nornicotine are decreased in the host *Nicotiana tabacum* plant cell as compared to a control *Nicotiana tabacum* plant cell and the levels of anabasine and anatabine are between about 90% and about 110% in the host *Nicotiana tabacum* plant cell as compared to the amount in the control *Nicotiana tabacum* plant cell.

Suitably, the levels of nicotine, anabasine and anatabine are increased and the level of nornicotine in the host *Nicotiana tabacum* plant cell is the same or increased as compared to a control *Nicotiana tabacum* plant cell.

Suitably, a dried or lyophilised green plant leaf harvested from a mature flowering plant comprising the non-naturally occurring or transgenic host *Nicotiana tabacum* plant cell comprises a ratio of anabasine:anatabine of between about 0.19 and about 0.25 or about 0.15; or a ratio of anabasine:nornicotine of between about 0.09 and about 0.15; or a ratio of anabasine:nicotine of between 0 and about 0.01; or a ratio of anatabine:nornicotine of between about 0.58 and about 0.73; or a ratio of anatabine:nicotine is between about 0.03 and about 0.04; or a ratio of nornicotine:nicotine of between about 0.05 and about 0.06; or a ratio of anabasine:anatabine of between about 0.19 and about 0.25 or about 0.15; and a ratio of anabasine:nornicotine of between about 0.09 and about 0.15; and a ratio of anabasine:nicotine of between 0 and about 0.01; and a ratio of nornicotine:nicotine of between about 0.05 and about 0.06; or a ratio of anabasine:anatabine of between about 0.19 and about 0.25 or about 0.15; and a ratio of anatabine:nornicotine of between about 0.58 and about 0.73; and a ratio of anatabine:nicotine of between about 0.03 and about 0.04; and a ratio of nornicotine:nicotine of between about 0.05 and about 0.06.

Suitably, a dried or lyophilised green plant leaf harvested from a mature flowering plant comprising the non-naturally occurring or transgenic host *Nicotiana tabacum* plant cell comprises: (i) a nicotine content of 8.1 mg/g±2.2 mg/g; (iii) a nornicotine content of 0.43 mg/g±0.09 mg/g: (iv) an anabasine content 0.06 mg/g±0.03 mg/g; and (v) an anatabine content of 0.31 mg/g±0.11 mg/g.

Suitably, a dried or lyophilised green plant leaf harvested from a mature flowering plant comprising the non-naturally occurring or transgenic host *Nicotiana tabacum* plant cell comprises: (i) a nicotine content of 7.8 mg/g±2.1 mg/g; (iii) a nornicotine content of 0.43 mg/g±0.10 mg/g; (iv) an anabasine content 0.06 mg/g±0.05 mg/g; and (v) an anatabine content of 0.27 mg/g±0.24 mg/g.

Suitably, a dried or lyophilised green plant leaf harvested from a mature flowering plant comprising the non-naturally occurring or transgenic host *Nicotiana tabacum* plant cell comprises: (i) a nicotine content of 14.0 mg/g±3.2 mg/g; (iii) a nornicotine content of 0.70 mg/g±0.15 mg/g; (iv) an anabasine content 0.06 mg/g±0.01 mg/g; and (v) an anatabine content of 0.41 mg/g±0.09 mg/g.

Suitably, the expression or activity of ADC in the host *Nicotiana tabacum* plant cell is reduced or inactivated.

In another aspect, there is disclosed a *Nicotiana tabacum* plant or part thereof comprising the non-naturally occurring or transgenic host *Nicotiana tabacum* plant cell described herein.

In another aspect, there is disclosed plant material from the *Nicotiana tabacum* plant or part thereof described herein, suitably, wherein the *Nicotiana tabacum* plant material is cured or dried plant material, suitably wherein the cured or dried *Nicotiana tabacum* plant material is flue-cured, fire-cured, smoke-cured, sun-cured, or air cured.

In another aspect, there is disclosed a tobacco product or smoking article comprising a part of the *Nicotiana tabacum* plant, or the *Nicotiana tabacum* plant material as described herein.

In another aspect, there is disclosed a method for producing the non-naturally occurring or transgenic host *Nicotiana tabacum* plant cell described herein, said method comprising: (a) providing a host plant cell from a *Nicotiana tabacum* plant; (b) modifying said host *Nicotiana tabacum* plant cell to comprise at least one of: (i) a heterologous polynucleotide comprising, consisting, or consisting essentially of a polynucleotide sequence having at least 96% sequence identity to SEQ ID NO: 1, or at least 97% sequence identity to SEQ ID NO: 3; or (ii) a heterologous polypeptide encoded by the polynucleotide set forth in (i); or (iii) a heterologous polypeptide comprising, consisting or consisting essentially of a polypeptide sequence having at least 97% sequence identity to SEQ ID NO: 2, at least 97.5% sequence identity to SEQ ID NO: 4; or (iv) a construct, vector or expression vector comprising the heterologous polynucleotide of (i), suitably wherein the heterologous polynucleotide is operably linked in the construct, vector or expression construct to a regulatory element, more suitably wherein the regulatory element is a promoter; or (v) a heterologous polynucleotide comprising, consisting, or consisting essentially of a polynucleotide sequence having at least 96.5% sequence identity to SEQ ID NO: 5; or (vi) a heterologous polypeptide encoded by the polynucleotide set forth in (v); or (vii) a heterologous polypeptide comprising, consisting or consisting essentially of a polypeptide sequence having at least 97.5% sequence identity to SEQ ID NO: 6; or (viii) a construct, vector or expression vector comprising the heterologous polynucleotide of (v), suitably wherein the heterologous polynucleotide is operably linked in the construct, vector or expression construct to a regulatory element, more suitably wherein the regulatory element is a promoter; wherein said heterologous polynucleotide or polypeptide encodes an arginine decarboxylase (ADC).

There is also described a non-naturally occurring or transgenic host *Nicotiana tabacum* plant cell obtained or obtainable by said method.

In another aspect, there is disclosed a method of altering the levels of one or more alkaloids in a *Nicotiana tabacum* plant, said method comprising: (i) performing (a) and (b) of the method set forth immediately above; and (ii) regenerating the non-naturally occurring or transgenic host *Nicotiana tabacum* plant cell into a *Nicotiana tabacum* plant; suitably, wherein the one or more alkaloids are selected from nicotine, nornicotine, anabasine and anatabine or a combination thereof.

In another aspect, there is disclosed a method for producing *Nicotiana tabacum* plant material with altered levels of one or more alkaloids, said method comprising: (A) performing (i) and (ii) of the method set forth immediately above; (B) propagating the *Nicotiana tabacum* plant; and C) harvesting plant material from the *Nicotiana tabacum* plant; suitably, wherein the one or more alkaloids with altered levels are selected from nicotine, nornicotine, anabasine and anatabine or a combination thereof.

Suitably, the method further comprises curing or drying the plant material.

Suitably, the method further comprises homogenising the plant material and extracting one or more alkaloids from the homogenised plant material and optionally further comprising separating one or more alkaloids of interest from other alkaloids, suitably wherein the alkaloid of interest is anatabine or anabasine.

In another aspect, there is disclosed a dried or lyophilised green plant leaf harvested from a mature flowering plant comprising the non-naturally occurring or transgenic host *Nicotiana tabacum* plant cell comprises a ratio of anabasine:anatabine of between about 0.19 and about 0.25 or about 0.15; or a ratio of anabasine:nornicotine of between about 0.09 and about 0.15; or a ratio of anabasine:nicotine of between 0 and about 0.01; or a ratio of anatabine:nornicotine of between about 0.58 and about 0.73; or a ratio of anatabine:nicotine is between about 0.03 and about 0.04; or a ratio of nornicotine:nicotine of between about 0.05 and about 0.06; or a ratio of anabasine:anatabine of between about 0.19 and about 0.25 or about 0.15; and a ratio of anabasine:nornicotine of between about 0.09 and about 0.15; and a ratio of anabasine:nicotine of between 0 and about 0.01; and a ratio of nornicotine:nicotine of between about 0.05 and about 0.06; or a ratio of anabasine:anatabine of between about 0.19 and about 0.25 or about 0.15; and a ratio of anatabine:nornicotine of between about 0.58 and about 0.73; and a ratio of anatabine:nicotine of between about 0.03 and about 0.04; and a ratio of nornicotine:nicotine of between about 0.05 and about 0.06.

Suitably, alkaloid amounts described herein are measured in dried or lyophilised green leaves of mature, flowering TO plants picked at the B-T position on the stalk (upper stalk position). Flowering T0 plants are picked about 3 months after transplantation in pots.

DETAILED DESCRIPTION OF THE INVENTION

Figure 1:
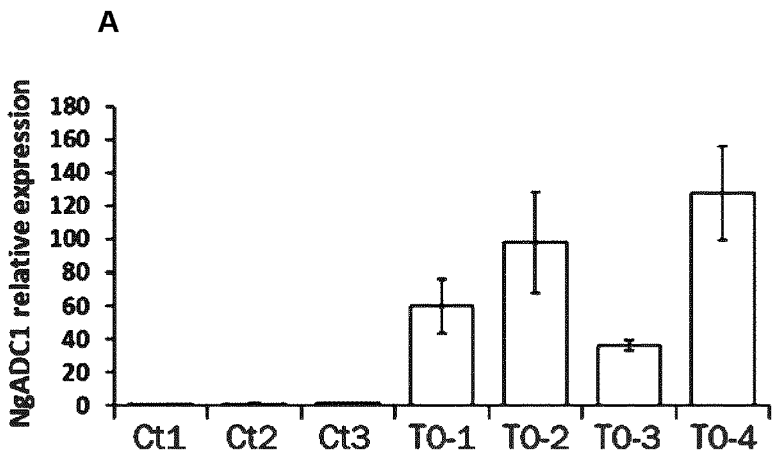
FIG. 1 is a series of graphs showing the expression of (A) NgADC1, (B) NgADC2 and (C) NdADC1 in TO transgenic overexpressing (OE) single plants.
Figure 1:
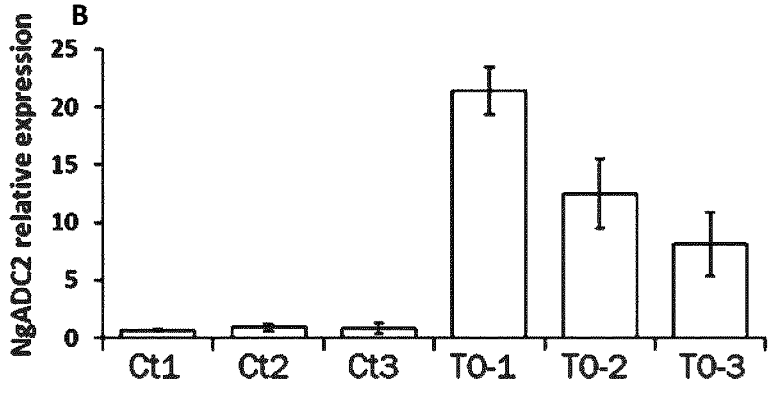
Figure 1:
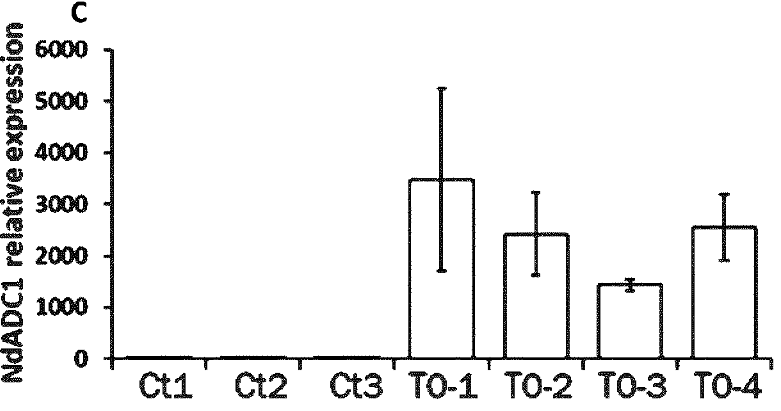

Unless otherwise defined below, all technical terms used herein have the same meaning as commonly understood by one of ordinary skill in the art in the field to which this disclosure belongs.

For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated. As used herein, the singular forms 'a', 'an', and 'the' include both singular and plural referents unless the context clearly dictates otherwise.

The term 'about' in the context of a given numerate value or range refers to a value or range that is ±20%, or ±10%, or ±5%, or ±4%, or ±3%, or ±2% or ±1% of the given value or range.

The terms 'total alkaloid content', 'alkaloid content', 'total alkaloid levels' and 'alkaloid levels' are used interchangeably to refer to the total amount of the most abundant alkaloids found in the plant cell, plant or part thereof, tobacco product or smoking article, that is, the sum of nicotine, nornicotine, anatabine, anabasine. Nicotine, nornicotine, anatabine and anabasine are the most abundant alkaloids in *Nicotiana tabacum*.

The terms 'comprising', 'comprises' and 'comprised of' are synonymous with 'including', 'includes', 'containing', 'contains', 'has', 'having', and 'can' are intended to be open-ended transitional phrases, terms, or words that do not preclude the possibility of additional acts or structures.

The term 'consisting of' is used to indicate that no further features are present other than those recited.

The term 'consisting essentially of' indicates that specific further components are present that do not materially affect the essential characteristics of the main component.

The term 'construct' refers to a double-stranded, recombinant nucleic acid fragment comprising one or more polynucleotides. The construct comprises a template strand base-paired with a complementary sense or coding strand. A given construct can be inserted into a vector in two possible orientations, either in the same (or sense) orientation or in the reverse (or anti-sense) orientation with respect to the orientation of a promoter positioned within a vector-such as an expression vector.

A 'control' in the context of a plant cell, plant or part thereof refers to a plant cell, plant or part thereof (or the resulting tobacco product or smoking article), into which a heterologous polynucleotide or polypeptide encoding an ADC as disclosed herein has not been introduced, but has been grown or cultured under the same conditions as the host into which the heterologous polynucleotide or polypeptide encoding the ADC has been introduced and is of the same species. For control tobacco products or smoking articles, the resulting tobacco product or smoking article is manufactured in the same way as the tobacco product or smoking article from the host plant cell, plant or part thereof. Thus, a control plant cell, plant or part thereof, tobacco product or smoking article, is equivalent to the host plant cell, plant or part thereof comprising the host plant cell or tobacco product or smoking article comprising the plant or part thereof comprising the host plant cell, including plant material in all parameters with the exception of the test parameters, that is, the introduction of at least one heterologous polynucleotide or polypeptide encoding the ADC.

The terms 'endogenous' or 'homologous' are used to refer to a polynucleotide or polypeptide which is naturally found in or native to the plant cell.

As used herein, the term 'expression' denotes the production of an RNA product through transcription of a gene, DNA or polynucleotide sequence, or the production of a polypeptide product encoded by a gene, DNA or polynucleotide sequence. 'Overexpression' is used herein to refer to an increase in expression of a polynucleotide or polypeptide.

'Expression vector' or 'expression cassette' are used herein to refer to a polynucleotide vehicle that comprises a combination of polynucleotide components for enabling the expression of the at least one heterologous polynucleotide encoding an ADC as disclosed herein. Expression cassettes or vectors may include episomes capable of extra-chromosomal replication such as circular, double stranded nucleotide plasmids; (circular or linearised) and other functionally equivalent expression vectors of any origin. The expression cassette or vector can be incorporated into a construct suitable for introducing into a plant cell, plant or part thereof.

The terms 'genome editing' or 'genetic editing' includes changing a polynucleotide such that expression of the polynucleotide is prohibited; or produces a truncated or modified RNA transcript; or a truncated or modified polypeptide.

The term 'growth phenotype' is used to refer to characteristics of plant growth such as degree of maturity, biomass, plant height, the absence of yellowing or chlorotic leaves, chlorophyll content, growth rate, number of leaves per plant, root length, root branching, stalk height, leaf insertion angle, stress tolerance, leaf size (width and length), internode distance, and lamina-midrib ratio. Growth phenotypic characteristics can be assessed by field observations at any stage of the growth cycle, including during plant development, senescence, or after curing. Changes in phenotype can be measured in plants grown under any conditions. Measurements of growth phenotypes may be performed using techniques standard in the art. The transgenic or non-naturally occurring host plant described herein can have the same growth phenotype as the control plant.

The term 'heterologous' in the context of a polynucleotide or polypeptide sequence refers to a foreign polynucleotide or polypeptide sequence that is artificially introduced into a host plant cell or inserted into the plant genome in a host plant cell, which does not normally or naturally comprise the artificially introduced or inserted polynucleotide or polypeptide sequence. For example, the host does not normally or naturally comprise the artificially introduced or inserted polynucleotide or polypeptide sequence in any of its material, cells, genome, DNA or RNA. Heterologous nucleic acids or proteins are not endogenous to the cell into which they are introduced but have been obtained from another cell, plant or synthetically or recombinantly produced. The heterologous polynucleotide or polypeptide sequence is from a plant species that is different to the host plant cell. By way of example, a polynucleotide or polypeptide sequence from *Nicotiana glauca* or *Nicotiana debneyi* that is not normally or naturally present in *Nicotiana tabacum* is a heterologous polynucleotide or polypeptide sequence.

'Homogenised' plant material is used herein to refer to 'lyophilised', 'pulverised', 'ground' or 'pulped' plant material, including cured or dried *Nicotiana* plant material. In embodiments, the homogenised plant material is from *Nicotiana tabacum*. Methods of homogenising plant material are standard in the art, and include, but are not limited to, mechanical grinding methods such as a bead beater, mill, blender, or mortar and pestle. As such, the present invention provides homogenised transgenic or non-naturally occurring host plant material comprising at least one heterologous polynucleotide or polypeptide encoding an ADC as disclosed herein.

The terms 'homology' or 'similarity' refers to the degree of sequence similarity between two polynucleotides or two polypeptides compared by sequence alignment. The degree of homology between two discrete polynucleotides being compared is a function of the number of identical, or matching, nucleotides at comparable positions.

The term 'host' refers to a plant cell or plant or part thereof comprising the plant cell into which at least one heterologous polynucleotide or polypeptide sequence encoding an ADC as disclosed herein is introduced by genetic engineering techniques such that the host comprising the sequence would not otherwise be found in nature. The 'host' of the present invention is *Nicotiana tabacum.*

The terms 'modulate' or 'alter' are used interchangeably to refer to causing or facilitating a qualitative or quantitative change, alteration, modification, modulation or variation in the levels, content, expression, activity or function of a given member. This may be an increase or a decrease. 'Increased' refers to an increase of at least 10%, at least 20%, at least 25%, at least 30%, at least 40%, at least 50%, at least 60%, at least 70%, at least 80%, at least 90%, at least 95%, at least 98%, at least 100%, at least 150%, at least 200% or more. For example, the increase may be in the level of one or more alkaloids in a transgenic or non-naturally occurring host plant cell, plant or part thereof, tobacco product or smoking article as disclosed herein as compared to a control. For example, the increase may be in the level of total alkaloids in the transgenic or non-naturally occurring host plant cell, plant or part thereof, tobacco product or smoking article as disclosed herein as compared to a control. For example, the increase may be in the level of expression of ADC as compared to a control. 'Decreased' refers to a decrease of at least 10%, at least 20%, at least 25%, at least 30%, at least 40%, at least 50%, at least 60%, at least 70%, at least 80%, at least 90%, at least 95%, at least 98%, at least 100%, at least 150%, at least 200% or more. For example, the decrease may be in the level of one or more alkaloids in the host transgenic or non-naturally occurring plant cell, plant or part thereof, tobacco product or smoking article as disclosed herein as compared to a control. For example, the decrease may be in the level of total alkaloids in the transgenic or non-naturally occurring host plant cell, plant or part thereof, tobacco product or smoking article as disclosed herein as compared to a control. For example, the decrease may be in the level of expression of ADC as compared to a control.

The term 'non-naturally occurring' describes an entity-such as a polynucleotide, polypeptide, plant cell, plant or part thereof—that is not formed by nature or that does not exist in nature.

The term 'nucleoside' refers to a molecule having a purine or pyrimidine base covalently linked to a ribose or deoxyribose sugar. Exemplary nucleosides include adenosine, guanosine, cytidine, uridine and thymidine. Additional exemplary nucleosides include inosine, 1-methyl inosine, pseudouridine, 5,6-dihydrouridine, ribothymidine, 2N-methylguanosine and 2,2N,N-dimethylguanosine (also referred to as rare nucleosides). 'Nucleosides' include synthetic, naturally occurring, modified nucleosides and nucleoside analogues.

The term 'nucleotide' or 'nucleotide residues' refers to any nucleoside having one or more phosphate groups joined in ester linkages to the sugar moiety. Exemplary nucleotides include nucleoside monophosphates, diphosphates and triphosphates. The term nucleotide is used generally to refer to nucleotides found in DNA and RNA; adenine (A), guanine (G), cytosine (C), thymine (T) and uracil (U). The term 'nucleotide' includes synthetic, or naturally occurring, nucleotides. In embodiments, the present nucleotide sequences may be modified to replace the intended nucleotide with 'nucleotide analogues', 'modified nucleotides' or 'altered nucleotides' which are non-standard, non-naturally occurring ribonucleotides or deoxyribonucleotides. Exemplary nucleotide analogues are modified at any position so as to alter certain chemical properties of the nucleotide yet retain the ability of the nucleotide analogue to perform its intended function. In addition, the phosphate group of the nucleotide may be modified by making substitutions which still allow the nucleotide to perform its intended function. Examples of nucleotide modifications include phosphoramidate, phosphorothioate, phosphorodithioate, or O-methylphophoroamidite linkages; and peptide polynucleotide backbones and linkages. Other analogue polynucleotides include those with positive backbones; non-ionic backbones, and non-ribose backbones.

The term 'one or more' or 'at least one' refers to a list of members, and refers to any one of said members, or any two or more of said members, including ≥3, ≥4, ≥5, ≥6 or ≥7 etc. of said members, and up to all said members.

The term 'operably linked' refers to a functional linkage between two or more elements, such as a regulatory element and the heterologous polynucleotide sequence encoding an ADC. Operably linked elements may be contiguous or non-contiguous.

As used herein, the term 'promoter' refers to a polynucleotide sequence that serves to control the transcription of heterologous polynucleotide sequence encoding an ADC, located upstream from the heterologous polynucleotide sequence encoding an ADC. In some embodiments, the promoter sequence is expressed in many tissue/cell types, while in other embodiments, the promoter may be tissue specific (that is, that expression is only affected in specific tissues but remains unchanged in others). Different promoters can have different strengths which can result in different amounts of heterologous polypeptide being produced in a host plant cell, plant or part thereof comprising the host plant cell or tobacco product or smoking article comprising the plant or part thereof comprising the host plant cell.

The terms 'propagating', 'propagate' or 'propagated' are used to refer to the process of breeding plants and includes both sexual and asexual propagation unless otherwise stated.

The term 'regenerating' or 'regeneration' is used to refer to the production of whole new plant organs (including roots and shoots) or plants from plant cells or plant tissue. Methods for regenerating plants or parts thereof from plant cells or plant tissue are standard in the art.

The term 'substantially the same' is used where entities are highly similar-such as within 5% or less or within 4% or less, or within 3% or less, or within 2% or less or within 1% or less, or within 0.5% or less, or with 0.1% of each other.

The term 'plant' encompasses whole plants, plant organs (for example, leaves, stems, roots), seeds, differentiated or undifferentiated plant cells, and progeny of the same at any stage of the life cycle.

'Plant cell' refers to a structural and physiological unit of a plant. The plant cell may be in the form of a protoplast without a cell wall, an isolated single cell or a cultured cell, or as a part of higher organized unit such as, but not limited to, plant tissues, a plant organ, or a whole plant. The plant cell may be derived or derivable from a plant, or it may be a cultured plant cell that is cultured outside of a plant, that is, in vitro. Methods for deriving a plant cell from a plant, and for culturing plant cells in vitro are standard in the art and are described in Davey and Anthony 2010. Plant cell culture: essential methods. Wiley-Blackwell and Negrutiu 1992. In Linsey (eds). Plant Tissue Culture Manual: 213-223.), and Hsu et al. (2020. *Frontiers in Genome Editing,* 2:39), for example.

'Parts thereof' in the context of a plant include, but are not limited to, plant cells, plant material, plant organs, plant protoplasts, plant cell tissues cultures, plant calli, plant clumps, embryos, pollen, anthers, ovules, branches, fruit, root tips, roots, stems, leaves, flowers, or seeds. In embodiments, the plant part may be leaves, stems or flowers or a combination thereof. The present disclosure provides parts of a plant, wherein said plant part comprises at least one heterologous polynucleotide or polypeptide encoding an ADC.

As used herein, the term 'plant material' includes seeds, biomass, flowers or flower parts, zygotes, cuttings, secretions, extracts, cell or tissue cultures, suspension cultures, embryos, meristematic regions, callus tissues, leaves, roots, shoots, stems, fruit, gametophytes, sporophytes, pollen, and microspores.

The terms 'polynucleotide', 'polynucleotide sequence', 'polynucleotide fragment' or 'nucleic acid molecule' are used interchangeably herein to refer to a polymer of nucleotides joined together by a phosphodiester or phosphorothioate linkage between 5' and 3' carbon atoms, including DNA. As used herein, the term 'DNA' or 'deoxyribonucleic acid' is used to specifically refer to a polymer of A, T, C and G nucleotides. A 'polynucleotide', as referred to herein, may be any length, including at least 2, 3, 4, 5, 10, 15, 20, 25, 30, 50, 100, 1000, 2000 or more nucleotides. The polynucleotide may be heterologous, homologous or artificially synthesised. The polynucleotide may be double stranded or single stranded.

'Polypeptide', 'polypeptide sequence', or 'protein' refers to a polymer of amino acids. The terms are also inclusive of synthetic and naturally occurring amino acids or modified amino acids. Examples of modifications include, but are not limited to, glycosylation, lipid attachment, sulfation, gamma-carboxylation of glutamic acid residues, hydroxylation and ADP-ribosylation.

The term 'sequence' refers to any contiguous string of nucleotides or amino acids. It may be at least 2, 5, 10, 15, 20, 30, 40, 50, 100, 200, 500, 1000, 2000 or more nucleotides or amino acids in length or the length can be defined by the polynucleotides or polypeptides in the sequence listing.

As used herein, the term 'sequence identity' refers to the similarity between two or more polynucleotide or polypeptide sequences.

'Significant' or 'significance' refer to statistical significance, that is, the calculation of the probability that entities do not differ only by chance or random events using standard methods known in the art, such as those detailed in Smith (2018) Statistical analysis handbook. *Drumlin Security Ltd.*

'Smoking articles' and 'smokable articles' are used interchangeably to refer to types of aerosol forming devices. Examples of smoking articles or smokable articles include cigarettes, cigarillos, and cigars. The tobacco in the smoking articles and smokable articles may be combusted or heated.

'Tobacco' refers to plant cells, plants or parts thereof, plant material or cured or dried plant material from *Nicotiana tabacum.*

'Tobacco product' refers to a consumer tobacco product comprising material produced by a *Nicotiana tabacum* plant, including, but not limited to, nicotine gum and patches for smoking cessation, smoking articles (including cigarillos, cigarettes, cigars, cigarette tobacco, pipe tobacco, expanded (puffed), homogenised and reconstituted tobacco, cigar tobacco), aerosol forming materials and devices, and all forms of smokeless tobacco products such as chewing tobacco, snuff, gum, and lozenges, as well as components, materials and ingredients for manufacture of consumer tobacco products. Suitably, these tobacco products are manufactured from tobacco leaves and stems harvested from tobacco and cut, dried, cured, and optionally fermented according to conventional techniques for tobacco preparation.

Tobacco products may contain tobacco in any form, including as dried particles, shreds, granules, powders, or a slurry, deposited on, mixed in, surrounded by, or otherwise combined with other ingredients in any format, such as flakes, films, tabs, foams, or beads. The tobacco products can be a blended tobacco product which may further comprise unmodified, wild-type tobacco.

'Transgenic' refers to any plant cell, plant or part thereof (including the resulting tobacco product or smoking article) where the genome has been altered by the presence of a heterologous polynucleotide, including the initial transgenic events as well as those plant cells, plants or parts thereof created by sexual crosses or asexual propagation from the initial transgenic event which may be stably integrated into the genome. The term does not encompass the alteration of the genome (chromosomal or extra-chromosomal) by conventional plant breeding methods or by naturally occurring events-such as random cross-fertilization, non-recombinant viral infection, non-recombinant bacterial transformation, non-recombinant transposition, or spontaneous mutation. Therefore, a 'transgenic' plant cell, plant or part thereof (including the resulting tobacco product or smoking article) comprises at least one heterologous polynucleotides or polypeptides encoding an ADC as disclosed herein.

The terms 'variant' or 'analogue' are used interchangeably to refer to a sequence which deviates from the given polynucleotide or polypeptide sequence, such as by the addition, removal or substitution or one or more nucleotides or amino acids.

The term 'plant variety' refers to a population of plants that share characteristics that separate them from other plants of the same species, and there is very small overall variation between individuals within that variety. Suitable varieties for use in the present invention are disclosed herein.

The term 'vector' is used to refer to any means capable of delivering or introducing any of the heterologous polynucleotides described herein into the host plant cell, plant or part thereof. 'Arginine decarboxylase' or 'ADC' is used herein to refer to the enzyme that is known to catalyse the formation of agmatine and carbon dioxide from arginine. The ADC can be encoded by a polynucleotide or polypeptide as disclosed herein.

ADC polynucleotides are disclosed herein. The polynucleotide may comprise, consist or consist essentially of SEQ ID NOs: 1 (NgADC1), 3 (NgADC2), or 5 (NdADC1). In embodiments, the polynucleotide may comprise a sequence with at least 70%, 75%, 80%, 81%, 82%, 83%, 85%, 86%, 90%, 91%, 92%, 93%, 94%, 95%, 95.5%, 96%, 96.5%, 97%, 98%, or 99% sequence identity with SEQ ID NOs: 1, 3 or 5 counted over the full length of the sequence.

In one embodiment, the polynucleotide may comprise, consist or consist essentially of SEQ ID NO: 1 or a sequence with at least 80%, 81%, 82%, 83%, 85%, 86%, 90%, 91%, 92%, 93%, 94%, 95%, 95.5%, 96%, 96.5%, 97%, 98%, or 99% sequence identity or at least 80% or at least 95% or at least 96% sequence identity counted over the full length of the sequence.

In another embodiment, the polynucleotide may comprise, consist or consist essentially of SEQ ID NO: 3 or a sequence with at least 80%, 81%, 82%, 83%, 85%, 86%, 90%, 91%, 92%, 93%, 94%, 95%, 95.5%, 96%, 96.5%, 97%, 98%, or 99% sequence identity or at least 80% or at least 81% or at least 95% or at least 97% sequence identity counted over the full length of the sequence.

In another embodiment, the polynucleotide may comprise, consist or consist essentially of SEQ ID NO: 5 or a sequence with at least 80%, 81%, 82%, 83%, 85%, 86%, 90%, 91%, 92%, 93%, 94%, 95%, 95.5%, 96%, 96.5%, 97%, 98%, or 99% sequence identity or at least 80% or at least 80% or at least 95% or at least 96.5% sequence identity counted over the full length of the sequence.

ADC polypeptides are also disclosed herein. The polypeptide may comprise, consist or consist essentially of SEQ ID NOs: 2 (NgADC1), 4 (NgADC2), or 6 (NdADC). In embodiments, the polypeptide may comprise a sequence with at least 70%, 75%, 80%, 83%, 84%, 85%, 86%, 90%, 91%, 92%, 93%, 94%, 95%, 96%, 96.5%, 97%, 97.5%, 98%, or 99% sequence identity to SEQ ID NOs: 2, 4 or 6 counted over the full length of the sequence.

In one embodiment, the polypeptide may comprise, consist or consist essentially of SEQ ID NO: 2 or a sequence with at least 80%, 81%, 82%, 83%, 85%, 86%, 90%, 91%, 92%, 93%, 94%, 95%, 95.5%, 96%, 96.5%, 97%, 98%, or 99% sequence identity or at least 83% or at least 97% sequence identity counted over the full length of the sequence.

In another embodiment, the polypeptide may comprise, consist or consist essentially of SEQ ID NO: 4 or a sequence with at least 80%, 81%, 82%, 83%, 85%, 86%, 90%, 91%, 92%, 93%, 94%, 95%, 95.5%, 96%, 96.5%, 97%, 97.5%, 98%, or 99% sequence identity or at least 83% or at least 96% or at least 97% or at least 97.5% sequence identity counted over the full length of the sequence.

In another embodiment, the polypeptide may comprise, consist or consist essentially of SEQ ID NO: 6 or a sequence with at least 80%, 81%, 82%, 83%, 85%, 86%, 90%, 91%, 92%, 93%, 94%, 95%, 95.5%, 96%, 96.5%, 97%, 97.5%, 98%, or 99% sequence identity or at least 83% or at least 80% or at least 96% or at least 97% or at least 97.5% sequence identity counted over the full length of the sequence.

In another embodiment, there is provided a polypeptide encoded by a polynucleotide comprising, consisting or consisting essentially of SEQ ID NOs: 1, 3 or 5.

In another embodiment, there is provided a polypeptide encoded by a polynucleotide comprising a sequence with at least 70%, 75%, 80%, 81%, 82%, 83%, 85%, 86%, 90%, 91%, 92%, 93%, 94%, 95%, 95.5%, 96%, 96.5%, 97%, 98%, or 99% sequence identity with SEQ ID NOs: 1, 3 or 5 counted over the full length of the sequence.

In a particular embodiment, there is disclosed a non-naturally occurring or transgenic host *Nicotiana tabacum* plant cell or plant or part thereof comprising the plant cell (including the resulting tobacco product or smoking article) comprising at least one of: a heterologous polynucleotide comprising, consisting, or consisting essentially of a polynucleotide sequence having at least 96% sequence identity to SEQ ID NO: 1, or at least 97% sequence identity to SEQ ID NO: 3; or a heterologous polypeptide encoded by the polynucleotide set forth in (i); or a heterologous polypeptide comprising, consisting or consisting essentially of a polypeptide sequence having at least 97% sequence identity to SEQ ID NO: 2, at least 97.5% sequence identity to SEQ ID NO: 4; or a heterologous polynucleotide comprising, consisting, or consisting essentially of a polynucleotide sequence having at least 96.5% sequence identity to SEQ ID NO: 5; or a heterologous polypeptide encoded by the polynucleotide set forth in (v); or a heterologous polypeptide comprising, consisting or consisting essentially of a polypeptide sequence having at least 97.5% sequence identity to SEQ ID NO: 6; or wherein said heterologous polynucleotide or polypeptide encodes an arginine decarboxylase (ADC).

Combinations of the polynucleotides and polypeptides disclosed herein are also contemplated. Such combinations can be contained in the non-naturally occurring or transgenic host *Nicotiana tabacum* plant cell or plant or part thereof comprising the host plant cell or tobacco product or smoking article comprising the plant or part thereof comprising the host plant cell, or plant material comprising host plant cell and the like as described herein. Such combinations may be contained in a vector or construct and the like.

By way of example, a *Nicotiana tabacum* plant cell, plant, plant part or plant material, vector or construct and the like comprising of at least one polynucleotide sequence comprising, consisting or consisting essentially of SEQ ID NOs: 13 (NtADC1-S) or 15 (NtADC1-T) or 17 (NtADC2-S) or 19 (NtADC2-T) may contain more than one heterologous polynucleotide sequence-such as more than one polynucleotide comprising, consisting or consisting essentially of SEQ ID NOs: 1 (NgADC1), 3 (NgADC2) and 5 (NdADC1) or a polynucleotide with at least 70%, 75%, 80%, 81%, 82%, 83%, 85%, 86%, 90%, 91%, 92%, 93%, 94%, 95%, 95.5%, 96%, 96.5%, 97%, 98%, or 99% sequence identity thereto. For example, the combination may be SEQ ID NO: 1 and 3 or SEQ ID NO: 1 and 5 or SEQ ID NO: 3 and 5 or SEQ ID NO: 1 and 3 and 5. Introducing combinations of polynucleotide sequences into a *Nicotiana tabacum* host may further modulate or alter alkaloid levels.

By way of example, a *Nicotiana tabacum* plant cell, plant, plant part or plant material, vector or construct comprising of at least one polypeptide sequence comprising, consisting or consisting essentially of SEQ ID NOs: 14 (NtADC1-S) or 16 (NtADC1-T) or 18 (NtADC2-S) or 20 (NtADC2-T) may contain more than one heterologous polypeptide sequence-such as more than one polypeptide comprising, consisting or consisting essentially of SEQ ID NO: 2 (NgADC1), 4 (NgADC2) and 6 (NdADC) or a polypeptide with at least 70%, 75%, 80%, 81%, 82%, 83%, 85%, 86%, 90%, 91%, 92%, 93%, 94%, 95%, 95.5%, 96%, 96.5%, 97%, 97.5%, 98%, or 99% sequence identity thereto. For example, the combination may be SEQ ID NO: 2 and 4 or SEQ ID NO: 2 and 6 or SEQ ID NO: 4 and 6 or SEQ ID NO: 2, 4 and 6. Introducing combinations of polypeptide sequences into the *Nicotiana tabacum* host may further modulate or alter alkaloid levels.

The polynucleotide of the present invention encodes a polypeptide having ADC activity.

Suitably, the at least one heterologous polynucleotide or heterologous polypeptide encoding the ADC is or is derived from *Nicotiana glauca* or *Nicotiana debneyi*.

Sequence identity is frequently measured in terms of percentage identity (or similarity or homology), so that the higher the percentage, the more similar the two sequences are. Homologs or variants of the nucleotide sequence will possess a relatively high degree of sequence identity when aligned using standard methods known in the art. For example, the percentage may be calculated by aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. Comparisons may be made over at least 50,100,200, 500, 1000, 1500 or 2000 nucleotides or amino acids but are preferably over the full length of the polynucleotide or polypeptide sequence. Identity may be determined manually or by using a computer sequence algorithm such as ClustalW, ClustalX, BLAST, FASTA, NCBI Blast 2.0 or Smith-Waterman. The popular multiple alignment program ClustalW (Nucleic Acids Research (1994) 22, 4673-4680; Nucleic Acids Research (1997), 24, 4876-4882) is a suitable way for generating multiple alignments of polypeptides or polynucleotides. Suitable parameters for ClustalW maybe as follows: For polynucleotide alignments: Gap Open Penalty=15.0, Gap Extension Penalty=6.66, and Matrix=Identity. For polypeptide alignments: Gap Open Penalty=10.0, Gap Extension Penalty=0.2, and Matrix=Gonnet. For DNA and Protein alignments: ENDGAP=−1, and GAPDIST=4. Those skilled in the art will be aware that it may be necessary to vary these and other parameters for optimal sequence alignment. Suitably, calculation of percentage identities is then calculated from such an alignment as (N/T), where N is the number of positions at which the sequences share an identical residue, and T is the total number of positions compared including gaps but excluding overhangs.

Variants of the polynucleotide or polypeptide sequences described herein are also contemplated. When percentage of sequence identity is used in reference to polypeptides, it is recognized that amino acids may be substituted for another amino acid with similar chemical properties, such as charge and hydrophobicity, and therefore do not change the functional properties of the molecule. These are referred to as 'conservative substitutions'. Determining which amino acids may be substituted, inserted or deleted can be achieved using computer programs—such as Vector NTI Suite (InforMax, MD) software. Conservative substitutions may be made, for example according to the Table below. Amino acids in the same block in the second column and preferably in the same line in the third column may be substituted for each other (see Table 1).

Where sequences differ in conservative substitutions, the percentage sequence identity may be adjusted upwards to correct for the conservative nature of the substitution. Sequences which differ by such conservative substitutions are said to have 'sequence similarity' or 'similarity'. Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, for example, according to the algorithm of Meyers & Miller, *Computer Applic. Biol. Sci.* 4:11-17 (1988), as implemented in the program PC/GENE (Intelligenetics, Mountain View, California, USA). Scale-invariant feature transform (SIFT) scores may also be used to predict whether an amino acid substitution affects protein function based on sequence homology and the physical properties of the amino acids. SIFT scores may be calculated based on methods known in the art, such as those described in Kumar et al. (2009) *Nature Protocols,* 4 (8): 1073-1082.

Use in this description of a percentage of sequence identity denotes a value determined by comparing two optimally aligned sequences over a comparison window, wherein the portion of the polynucleotide sequence in the comparison window may comprise additions or deletions (gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The present disclosure provides a transgenic or non-naturally occurring host *Nicotiana tabacum* plant cell, plant or part thereof, tobacco product or smoking article, comprising at least one heterologous polynucleotide or polypeptide encoding an ADC from *Nicotiana glauca* or *Nicotiana debneyi* as described herein. In one embodiment, the endogenous ADC of the host *Nicotiana tabacum* plant cell or plant or part thereof comprising the host plant cell or tobacco product or smoking article comprising the plant or part thereof comprising the host plant cell comprises of at least one polynucleotide sequence comprising, consisting or consisting essentially of SEQ ID NOs: 13 (NtADC1-S), 15 (NtADC1-T), 17 (NtADC2-S) or 19 (NtADC2-T). In another embodiment, the endogenous ADC of the host *Nicotiana tabacum* plant cell or plant or part thereof comprising the host plant cell or tobacco product or smoking article comprising the plant or part thereof comprising the host plant cell comprises at least one polypeptide sequence comprising, consisting or consisting essentially of SEQ ID NOs: 14 (NtADC1-S), 16 (NtADC1-T), 18 (NtADC2-S) or 20 (NtADC2-T).

Non-naturally occurring or artificial host plants or parts thereof may be made by methods described herein or that are well known in the art. Such entities may be made by man. Non-naturally occurring or artificial host plants or parts thereof contain one or more heterologous polynucleotides or polypeptides that from a different plant species to the non-naturally occurring or artificial host plant or parts thereof. The host plant cell, plant or part thereof is *Nicotiana tabacum.*

In embodiments, the heterologous polynucleotide or polypeptide is from *Nicotiana glauca* or *Nicotiana debneyi*. More than one heterologous polynucleotide or polypeptide from *Nicotiana glauca* and *Nicotiana debneyi* may be present in the *Nicotiana tabacum* host.

Wild type *Nicotiana tabacum, Nicotiana glauca* and *Nicotiana debneyi* are publicly available. For example, these species are available from the United States Department of Agriculture, Agricultural Research Service, North Carolina State University, Department of Crop Science, Box 7620, 4309 Williams Hall, Raleigh, North Carolina 27695. For example, *Nicotiana glauca* is available as cultivar TW53, TW55, TW56 and TW57 and *Nicotiana debneyi* (named as forsteri) is available as cultivar TW37, TW38, TW39 and TW40. *Nicotiana tabacum, Nicotiana glauca* and *Nicotiana debneyi* seeds are available from NiCoTa GmbH, Kutschenweg 20, 76287 Rheinstetten, Germany as registration number 16 (*Nicotiana tabacum*), registration number 1 (*Nicotiana glauca*) and registration number 49 (*Nicotiana debneyi*). Bergerac Seed & Breeding, La Tour, 24100 Bergerac, France also supplies *Nicotiana tabacum, Nicotiana glauca* (accession numbers 486, 487 and 488) and *Nicotiana debneyi* (accession numbers 584 to 588, idem USDA-GRIN (NCSU)).

Wild type *Nicotiana glauca* accumulates predominantly anabasine rather than nicotine and nornicotine as the main component of its leaf pyridine alkaloid fraction. As shown in Sisson and Severson (1990) supra and in Table 2 herein, wild type *Nicotiana glauca* has a very low level of nicotine, thereby suggesting that there is a possible pathway shift preventing the formation of putrescine and stimulating the formation of cadaverine, both being precursors of nicotine and anabasine, respectively. Wild type *Nicotiana debneyi* is not as altered in the production of nicotine as wild type *Nicotiana glauca* and balanced in nicotine and anabasine production (Sisson and Severson (1990) supra and Table 2). As described herein, expression of *Nicotiana glauca* ADC or *Nicotiana debneyi* ADC in a *Nicotiana tabacum* host can result in altered levels of alkaloids therein.

Also provided is a tissue culture of regenerable plant cells, which is capable of being regenerated into a plant. The regenerable cells may include cells from leaves, pollen, embryos, cotyledons, hypocotyls, roots, root tips, anthers, flowers and a part thereof, ovules, shoots, stems, stalks, pith and capsules or callus or protoplasts derived therefrom. The present disclosure therefore provides tissue cultures of transgenic or non-naturally occurring *Nicotiana tabacum* host plant cells comprising at least one heterologous polynucleotide or polypeptide encoding an ADC as disclosed herein.

Plant parts, including seeds, of the plant described herein can be conditioned and bagged in packaging material by means known in the art to form an article of manufacture. Packaging material are well known in the art. A package of seeds can have a label, for example, a tag or label secured to the packaging material or a label printed on the package that describes the nature of the seeds therein.

In one embodiment, the plant material is a leaf or stem or a combination thereof. Suitably, the plant material is 'cured or dried'. Processes of curing green tobacco leaves are known by those skilled in the art and include, without limitation, air-curing, fire-curing, flue-curing and sun-curing. Examples of drying process include fast drying, for example, in an oven, and lyophilisation. The process of curing green tobacco leaves depends on the type of tobacco harvested. For example, Virginia flue (bright) tobacco is typically flue-cured, Burley and certain dark strains are usually air-cured, and pipe tobacco, chewing tobacco, and snuff are usually fire-cured. The present disclosure therefore provides transgenic or non-naturally occurring *Nicotiana tabacum* plant material, including cured or dried plant material, comprising at least one heterologous polynucleotide or polypeptide encoding an ADC from *Nicotiana glauca* or *Nicotiana debneyi* or a combination thereof as disclosed herein.

In a further embodiment, the *Nicotiana tabacum* host plant cell, plant or part thereof (including the tobacco product or smoking article thereof) is a *Nicotiana tabacum* variety, cultivar or elite *Nicotiana tabacum* cultivar. *Nicotiana tabacum* varieties include Burley type, dark type, flue-cured type, and Oriental type tobaccos. Non-limiting examples of varieties or cultivars are: AA37, BO 64, CC 101, CC 200, CC 27, CC 301, CC 400, CC 500, CC 600, CC 700, CC 800, CC 900, Coker 176, Coker 319, Coker 371 Gold, Coker 48, CD 263, DF911, OT 538 LC Galpao tobacco, GL 26H, GL 350, GL 600, GL 737, GL 939, GL 973, HB 04P, HB 04P LC, HB3307PLC, Hybrid 403LC, Hybrid 404LC, Hybrid 501 LC, K 149, K 326, K 346, K 358, K394, K 399, K 730, KOH 959, KT 200, KT204LC, KY10, KY14, KY 160, KY 17, KY 171, KY 907, KY907LC, KY14xL8 LC, Little Crittenden, McNair 373, McNair 944, msKY 14xL8, Narrow Leaf Madole, Narrow Leaf Madole LC, NBH 98, N-126, N-777LC, N-7371LC, NC 100, NC 102, NC 2000, NC 291, NC 297, NC 299, NC 3, NC 4, NC 5, NC 6, NC 606, NC 71, NC 72, NC 810, NC BH 129, NC 2002, Neal Smith Madole, OXFORD 207, PD 7302 LC, PD 7309 LC, PD 7312 LC, 'Perique' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN97, TN97LC, TN D94, TN D950, TR (Tom Rosson) Madole, VA 309, VA359, AA 37-1, B13P, Xanthi (Mitchell-Mor), Bel-W3, 79-615, Samsun Holmes NN, KTRDC number 2 Hybrid 49, Burley 21, KY8959, KY9, MD 609, PG01, PG04, PO1, PO2, PO3, RG11, RG 8, VA509, AS44, Banket A 1, Basma Drama B84/31, Basma I Zichna ZP4/B, Basma Xanthi BX 2A, Batek, Besuki Jember, C104, Coker 347, Criollo Misionero, Delcrest, Djebel 81, DVH 405, Galpao Comum, HB04P, Hicks Broadleaf, Kabakulak Elassona, Kutsage E1, LA BU 21, NC 2326, NC 297, PVH 2110, Red Russian, Samsun, Saplak, Simmaba, Talgar 28, Wislica, Yayaldag, Prilep HC-72, Prilep P23, Prilep PB 156/1, Prilep P12-2/1, Yaka JK-48, Yaka JB 125/3, TI-1068, KDH-960, TI-1070, TW136, Basma, TKF 4028, LS, TKF 2002, GR141, Basma xanthi, GR149, GR153, or Petit Havana. Low converter subvarieties of the above, even if not specifically identified herein, are also contemplated.

The *Nicotiana tabacum* host plant may be grown under any suitable conditions, including hydroponically, in a greenhouse or in a field using standard techniques in the art.

'Alkaloids' are complex organic molecules comprising or containing a heterocyclic nitrogen ring. Approximately 10% of all plant species are thought to produce alkaloids as secondary metabolites from amino acids, and in plants, alkaloids are thought to function as a defence against herbivores and pathogens. A 'pyrrolidine alkaloid' is an alkaloid containing a pyrrolidine ring as part of its molecular structure. Nicotine, nornicotine, anatabine and anabasine are pyrrolidine alkaloids. Nicotine, nornicotine, anatabine and anabasine are also referred to as 'pyridine alkaloids' in the published literature. A 'pyridine alkaloid' is an alkaloid containing a pyridine ring as part of its molecular structure. A 'nicotinic alkaloid' refers to nicotine, or an alkaloid that is structurally related to nicotine and is synthesized from a compound produced in the nicotine biosynthesis pathway. 'Nicotinic alkaloids' include, but are not limited to nicotine, nornicotine, anatabine, anabasine, anatalline, N-methylanatabine, N-methylanabasine, myosmine, anabaseine, formylnornicotine, nicotyrine, and cotinine. Other minor nicotinic alkaloids in *N. tabacum* are reported, for example, in Hecht et al. 1979. *Accounts of Chemical Research* 12:92-98. In embodiments, the term 'alkaloids' refers preferentially to nicotine ($C_{10}H_{14}N_2$), nornicotine ($C_9H_{12}N_2$), anatabine ($C_{10}H_{12}N_2$) or anabasine ($C_{10}H_{14}N_2$). Structures for alkaloids are shown in Hecht et al. (1979) supra.

The levels of total or individual alkaloids may be measured as μg/g or mg/g dry weight (DW) or fresh weight (FW) of plant material. References to total or individual alkaloids includes reference to all enantiomers of the relevant alkaloid(s) unless otherwise specified. References to total or individual alkaloids refers to the naturally occurring enantiomer found in the host *Nicotiana tabacum* plant cell, plant or part thereof, tobacco product or smoking article as disclosed herein.

As described herein, the levels of total or individual alkaloids may be increased or decreased in the non-naturally occurring or transgenic *Nicotiana tabacum* host plant cell, plant or part thereof, tobacco product or smoking article as disclosed herein, as compared to a control. The levels or amounts of total or individual alkaloids can be measured as μg/g, mg/g or percent per dry weight (DW) or fresh weight (FW) compared to a control. Levels reported herein are in μg/g or mg/g.

The levels of total or individual alkaloids (nicotine or nornicotine or anabasine or anatabine) are modulated in accordance with the present disclosure. The levels of total or individual alkaloids may be increased or decreased as compared to a control in accordance with the present disclosure. In one embodiment, the levels of nicotine and nornicotine are decreased in the host *Nicotiana tabacum* plant cell as compared to a control *Nicotiana tabacum* plant cell and the levels of anabasine and anatabine are between about 90% and about 110% in the host *Nicotiana tabacum* plant cell as compared to the amount in the control *Nicotiana tabacum* plant cell. Suitably the levels of anabasine and anatabine are between about 95% and about 105%, or between about 98% and about 102%, or between about 99% and about 101% in the host *Nicotiana tabacum* plant cell as compared to the amount in the control *Nicotiana tabacum* plant cell. Suitably the levels of anabasine and anatabine are the same in the host *Nicotiana tabacum* plant cell as compared to the amount in the control *Nicotiana tabacum* plant cell. In another embodiment, the levels of nicotine, anabasine and anatabine are increased and the level of nornicotine in the host *Nicotiana tabacum* plant cell is the same or increased as compared to a control *Nicotiana tabacum* plant cell. Suitably, the levels are modulated, increased or decreased in leaf-such as dried or lyophilised green plant leaf harvested from a mature flowering plant. Suitably, the levels or amounts or percentages or ratios indicated below are in leaf-such as dried or lyophilised green plant leaf harvested from a mature flowering plant.

In embodiments, the levels of total alkaloids may be increased by at least 1000, 2000, 3000, or 4000 μg/g as compared to a control. In embodiments, the level of total alkaloids may be increased to between 11000 to 19000, 11000 to 17000, 12000 to 16000, or 13000 to 16000 μg/g.

In embodiments, the levels of total alkaloids may be decreased by at least 1000, 1500, 2000, or 2500 μg/g as compared to a control. In embodiments, the level of total alkaloids may be decreased to between 5000 to 10000, 6000 to 10000, or 7000 to 9000 μg/g.

In embodiments, the level of total alkaloids in the control plant cell, plant or part thereof, tobacco product or smoking article may be between 10100 to 15000, 11000 to 15000, 10000 to 14000, or 11000 to 13000 μg/g.

In embodiments, the level of nicotine may be increased by at least 500, 1000, 2000, 2500, 3000 or 3500 μg/g as compared to a control. In embodiments, the level of nicotine may be increased to between 11000 to 18000, 11000 to 17000, 11000 to 16000, 12000 to 18000, 12000 to 17000, 12000 to 16000, 13000 to 16000, 13000 to 15000, or 13500 to 14500 μg/g. In embodiments, the level of nicotine may be decreased by at least 500, 1000, 1500, 2000, or 2500 μg/g as compared to a control. In embodiments, the level of nicotine may be decreased to between 4500 to 9500, 5000 to 9500, 6000 to 9500, 6000 to 9000, 6500 to 9500, 6500 to 9000, 7000 to 9500, 7000 to 9000, or 7500 to 8500 μg/g.

In embodiments, the level of nicotine in the control plant cell, plant or part thereof, tobacco product or smoking article may be between 9000 to 13000, 9000 to 13000, 9500 to 13000, 9500 to 12500, 9000 to 12000, 9500 to 12000, 9000 to 11150, 9500 to 11150, or 9000 to 11000 μg/g.

In embodiments, the level of nornicotine may be increased by at least 20, 40, 50, 60, 80, 100, 110, 120, 130, or 140 μg/g as compared to a control. In embodiments, the level of nornicotine may be increased to between 590 to 900, 600 to 900, 600 to 850, or 600 to 800 μg/g.

In embodiments, the level of nornicotine may be decreased by at least 20, 40, 50, 60, 80, 100, 110, 120, 125, or 130 μg/g as compared to a control. In embodiments, the level of nornicotine may be decreased to between 200 to 520, 200 to 500, 250 to 520, 250 to 500, 300 to 520, 300 to 500, 350 to 520, 350 to 500, or 400 to 500 μg/g.

In embodiments, the level of nornicotine may not be significantly different from the level of nornicotine in a control as determined by standard statistical tests. In embodiments, the level of nornicotine may be substantially the same as a control. In embodiments, the level of nornicotine in the control plant cell or plant or part thereof comprising the host plant cell or tobacco product or smoking article comprising the plant or part thereof comprising the host plant cell may be between 400 to 660, 450 to 610, 450 to 600, 500 to 600, 510 to 610 μg/g. In embodiments, the level of anabasine may not be significantly different from a control as determined by standard statistical tests. In embodiments, the level of anabasine may be substantially the same as a control. In embodiments, the level of anabasine may be increased by at least 5, 10, 15, 17, 18, 19, 20, 21 or 23 μg/g as compared to a control. In embodiments, the level of anabasine may be increased to between 50 to 75, 55 to 75, 55 to 70, or 60 to 70 μg/g. In embodiments, the level of anabasine in the control plant cell, plant or part thereof, tobacco product or smoking article may be between 30 to 50 or 35 to 45 μg/g.

In embodiments, the level of anatabine may not be significantly different from a control as determined by standard statistical tests. In embodiments, the level of anatabine may be substantially the same as a control. In embodiments, the level of anatabine may be increased by at least 10, 15, 20, 25, 50, 60, 65, 70, 100, 110, 120, 130, 140, 150, or 160 μg/g as compared to a control. In embodiments, the level of anatabine may be increased to between 280 to 600, 300 to 500, 300 to 450, 350 to 450, 280 to 360, 290 to 350, 300 to 340, 310 to 330, 305 to 330 or 305 to 330 μg/g. In embodiments, the level of anatabine in the control plant cell, plant or part thereof, tobacco product or smoking article may be between 210 to 270, 220 to 260, 230 to 250, or 237 to 2457 μg/g.

In one embodiment, the present disclosure provides a transgenic or non-naturally occurring host *Nicotiana tabacum* plant cell, plant or part thereof, tobacco product or smoking article, comprising (i) a total alkaloid content of between 5.0 and 10.0 mg/g; and (ii) a nicotine content of between 6.0 and 9.5 mg/g; and (ill) a nornicotine content of between 0.2 and 0.49 mg/g; and (iv) an anabasine content of between 0.050 and 0.080 mg/g; and (v) an anatabine content of between 0.255 and 0.60 mg/g.

In another embodiment, the transgenic or non-naturally occurring host *Nicotiana tabacum* plant cell, plant or part thereof, tobacco product or smoking article comprises (i) a total alkaloid content of between 7.0 and 10.0 mg/g: (ii) a nicotine content of between 6.0 and 9.0 mg/g; (iii) a nornicotine content of between 0.35 and 0.5 mg/g; (iv) an anabasine content of between 0.055 and 0.070 mg/g; and (v) an anatabine content of between 0.255 and 0.4 mg/g.

In another embodiment, the present invention provides a transgenic or non-naturally occurring host *Nicotiana tabacum* plant cell, plant or part thereof, tobacco product or smoking article, comprising: (i) a total alkaloid content of between 12.5 and 17.0 mg/g; (ii) a nicotine content of between 11.5 and 17.0 mg/g; (iii) a nornicotine content of between 0.60 and 0.80 mg/g; (iv) an anabasine content of between 0.050 and 0.080 mg/g; and (v) an anatabine content of between 0.30 and 0.60 mg/g.

In another embodiment, the transgenic or non-naturally occurring host *Nicotiana tabacum* plant cell, plant or part thereof, tobacco product or smoking article, comprises: (i) a total alkaloid content of between 13.0 and 17.0 mg/g; (ii) a nicotine content of between 12.0 and 16.0 mg/g; (iii) a nornicotine content of between 0.60 and 0.80 mg/g; (Iv) an anabasine content of between 0.055 and 0.070 mg/g; and (v) an anatabine content of between 0.3 and 0.5 mg/g. In embodiments, the control *Nicotiana tabacum* plant cell, plant or part thereof, tobacco product or smoking article comprises: (i) a total alkaloid content of between 10.1 and 12.9 mg/g; (ii) a nicotine content of between 9.1 and 11.9 mg/g; (iii) a nornicotine content of between 0.50 to 0.59 mg/g; (iv) an anabasine content of 0.030 to 0.049 mg/g; and (v) an anatabine content of between 0.20 to 0.270 mg/g.

In another embodiment, the transgenic or non-naturally occurring host *Nicotiana tabacum* plant cell, plant or part thereof, tobacco product or smoking article, comprises: (i) a nicotine content of 8.1 mg/g±2.2 mg/g; (ii) a nornicotine content of 0.43 mg/g±0.09 mg/g; (iii) an anabasine content 0.06 mg/g±0.03 mg/g; and (iv) an anatabine content of 0.31 mg/g±0.11 mg/g.

In another embodiment, the transgenic or non-naturally occurring host *Nicotiana tabacum* plant cell, plant or part thereof, tobacco product or smoking article, comprises: (i) a nicotine content of 7.8 mg/g±2.1 mg/g; (ii) a nornicotine content of 0.43 mg/g±0.10 mg/g; (iii) an anabasine content 0.06 mg/g±0.05 mg/g; and (iv) an anatabine content of 0.27 mg/g±0.24 mg/g.

In another embodiment, the transgenic or non-naturally occurring host *Nicotiana tabacum* plant cell, plant or part thereof, tobacco product or smoking article, comprises: (i) a nicotine content of 14.0 mg/g±3.2 mg/g; (ii) a nornicotine content of 0.70 mg/g±0.15 mg/g; (iii) an anabasine content 0.06 mg/g±0.01 mg/g; and (iv) an anatabine content of 0.41 mg/g±0.09 mg/g.

In another embodiment, the control *Nicotiana tabacum* plant cell, plant or part thereof, tobacco product or smoking article comprises: (i) a nicotine content of 10.4 mg/g±1.0 mg/g; (ii) a nornicotine content of 0.56 mg/g±0.06 mg/g; (iii) an anabasine content of 0.043 mg/g #0.007 mg/g; and (iv) an anatabine content of 0.24 mg/g±0.04 mg/g.

The levels of total or individual alkaloids in the non-naturally occurring or transgenic host plant cell, plant or part thereof, tobacco product or smoking article may be measured as a percentage of the levels of total or individual alkaloids in a control plant cell, plant or part thereof, tobacco product or smoking article.

In one embodiment, the level of total alkaloids in the transgenic or non-naturally occurring host plant cell, plant or part thereof, tobacco product or smoking article may be increased by at least 10%, 15%, 20%, 25%, 30%, 35%, 40%, 50%, 60%, 70%, 80%, 90% as compared to a control. In another embodiment, the level of total alkaloids in the transgenic or non-naturally occurring host plant cell, plant or part thereof, tobacco product or smoking article may be increased by between 10% to 100%, 10% to 90%, 10% to 80%, 10% to 70%, 10% to 60%, 10% to 50%, 15% to 50%, 20% to 45%, or 30% to 40% as compared to a control. In another embodiment, the level of total alkaloids in the transgenic or non-naturally occurring host plant cell, plant or part thereof, tobacco product or smoking article may be increased by over 100% as compared to a control. In another embodiment, the level of total alkaloids in the transgenic or non-naturally occurring host plant cell, plant or part thereof, tobacco product or smoking article may be decreased by at least 5%, 10%, 15%, 20% or 25% as compared to a control. In embodiments, the level of total alkaloids in the transgenic or non-naturally occurring host plant cell, plant or part thereof, tobacco product or smoking article may be decreased by between 5% to 100%, 10% to 100%, 15% to 100%, 20% to 100%, 10% to 90%, 15% to 90%, 10% to 80%, 15% to 80%, 10% to 70%, 15% to 70%, 10% to 60%, 15% to 60%, 10% to 50%, 15% to 50%, 10% to 40%, 15% to 40%, 10% to 30%, 15% to 30%, or 20% to 30% as compared to a control.

In another embodiment, the level of nicotine in the transgenic or non-naturally occurring host plant cell, plant or part thereof, tobacco product or smoking article may be increased by at least 10%, 15%, 20%, 25%, 30%, or 35%, as compared to a control. In another embodiment, the level of nicotine in the transgenic or non-naturally occurring host plant cell, plant or part thereof, tobacco product or smoking article may be increased by over 100% as compared to a control. In another embodiment, the level of nicotine in the transgenic or non-naturally occurring host plant cell, plant or part thereof, tobacco product or smoking article may be increased by between 10% to 100%, 10% to 90%, 10% to 80%, 10% to 70%, 10% to 60%, 10% to 50%, 15% to 50%, 20% to 45%, or 30% to 40% as compared to a control.

In another embodiment, the level of nicotine in the transgenic or non-naturally occurring host plant cell, plant or part thereof, tobacco product or smoking article may be decreased by at least 5%, 10%, 15%, 20% or 25% as compared to a control. In another embodiment, the level of nicotine in the transgenic or non-naturally occurring host plant cell, plant or part thereof, tobacco product or smoking article may be decreased by between 5% to 100%, 10% to 100%, 15% to 100%, 20% to 100%, 10% to 90%, 15% to 90%, 10% to 80%, 15% to 80%, 10% to 70%, 15% to 70%, 10% to 60%, 15% to 60%, 10% to 50%, 15% to 50%, 10% to 40%, 15% to 40%, 10% to 35%, 15% to 35%, 10% to 30%, 15% to 30%, or 20% to 30% as compared to a control.

In another embodiment, the level of nornicotine may be increased by at least 5%, 10%, 15%, 20%, 21%, 22%, 23%, or 24% as compared to a control. In another embodiment, the level of nornicotine may be increased by over 100% as compared to a control. In another embodiment, the level of nornicotine may be increased by between 10% to 100%, 10% to 90%, 10% to 80%, 10% to 70%, 10% to 60%, 10% to 50%, 10% to 40%, 15% to 35% or 20% to 30% as compared to a control.

In another embodiment, the level of may be decreased by at least 5%, 10%, 15%, 20%, 21%, 22%, 23%, 24% or 25% as compared to a control. In another embodiment, the level may be decreased by between 5% to 100%, 10% to 100%, 15% to 100%, 20% to 100%, 10% to 90%, 15% to 90%, 10% to 80%, 15% to 80%, 10% to 70%, 15% to 70%, 10% to 60%, 15% to 60%, 10% to 50%, 10% to 40%, 15% to 35%, or 20% to 30% as compared to a control.

In another embodiment, the levels of nornicotine may not be significantly different from the level of nornicotine in a control as determined by standard statistical tests. In embodiments, the level of nornicotine may be substantially the same as a control-such as within 5% or less or within 4% or less, or within 3% or less, or within 2% or less or within 1% or less, or within 0.5% or less or within 0.1% of the control.

In another embodiment, the level of anabasine may be increased by at least 10%, 20%, 30%, 35%, 40%, 41%, 42%, 43%, 45%, 50%, 51%, 52% or 53% as compared to a control. In another embodiment, the level of anabasine may be increased by over 100% as compared to a control. In embodiments, the level of anabasine may be increased by between 10% to 100%, 10% to 90%, 10% to 80%, 10% to 70%, 10% to 65%, 10% to 60%, 15% to 60%, 20% to 70%, 20% to 60%, 25% to 75%, 30% to 65%, 30% to 60%, 35% to 60%, or 40% to 60% as compared to a control.

In another embodiment, the level of anabasine may not be significantly different from a control as determined by standard statistical tests. In embodiments, the level of anabasine may be substantially the same as a control-such as within 5% or less or within 4% or less, or within 3% or less, or within 2% or less or within 1% or less, or within 0.5% or less or within 0.1% of the control.

In another embodiment, the level of anatabine may be increased by at least 5%, 6%, 7%, 8%, 9%, 10%, 15%, 20%, 25%, 28%, 29%, 30%, 35%, 40%, 45%, 50%, 55%, 60%, 65% or 67% as compared to a control. In another embodiment, the level of anatabine may be increased by over 100% as compared to a control. In another embodiment, the level of anatabine may be increased by between 5% to 20%, 5% to 15%, 10% to 100%, 10% to 90%, 10% to 80%, 10% to 70%, 20% to 100%, 20% to 90%, 20% to 80%, 20% to 70%, 15% to 45%, 20% to 40%, 30% to 100%, 40% to 100%, 50% to 100%, 50% to 90%, 55% to 85%, 60% to 80%, or 60% to 90% as compared to a control. In another embodiment, the level of anatabine may not be significantly different from a control as determined by standard statistical tests. In embodiments, the level of anatabine may be substantially the same as a control-such as within 5% or less or within 4% or less, or within 3% or less, or within 2% or less or within 1% or less, or within 0.5% or less or within 0.1% of the control.

In another embodiment, the transgenic or non-naturally occurring host *Nicotiana tabacum* plant cell, plant or part thereof, tobacco product or smoking article, comprises: (i) 91% nicotine; (ii) 5% nornicotine; (iii) 0.5% anabasine; and (iv) 3.5% anatabine.

In another embodiment, the transgenic or non-naturally occurring host *Nicotiana tabacum* plant cell, plant or part thereof, tobacco product or smoking article, comprises: (i) 91% nicotine; (ii) 5% nornicotine; (iii) 1% anabasine; and (iv) 3% anatabine.

In another embodiment, the transgenic or non-naturally occurring host *Nicotiana tabacum* plant cell, plant or part thereof, tobacco product or smoking article, comprises: (i) 92% nicotine; (ii) 4.6% nornicotine: (iii) 0.6% anabasine; and (v) 2.8% anatabine.

In another embodiment, the control *Nicotiana tabacum* plant cell, plant or part thereof, tobacco product or smoking article comprises: (i) 92% nicotine; (ii) 5.3% nornicotine; (iii) 0.4% anabasine; and (iv) 2.3% anatabine.

The amounts of anabasine, anatabine, nornicotine and nicotine can also be expressed as ratios. All ratios described herein are calculated by dividing the amount of the first named alkaloid into the amount of the second named alkaloid, for example, to calculate the ratio of anabasine:anatabine the amount of anabasine is divided into the amount of anatabine. In one aspect, there is disclosed a dried or lyophilised green plant leaf harvested from a mature flowering *Nicotiana tabacum* plant comprising a ratio of anabasine:anatabine of about 0.19; or a ratio of anabasine:nornicotine of about 0.14; or a ratio of anabasine:nicotine of about 0.007; or a ratio of anatabine:nornicotine of about 0.73; or a ratio of anatabine:nicotine is about 0.04; or a ratio of nornicotine:nicotine of about 0.05; or a ratio of anabasine:anatabine of about 0.19; or a ratio of anabasine:anatabine of abut 0.19; and a ratio of anabasine:nornicotine of about 0.14 and a ratio of anabasine:nicotine of about 0.007; and a ratio of nornicotine:nicotine of about 0.05; or a ratio of anabasine:anatabine of about 0.19; and a ratio of anatabine:nornicotine of about 0.73; and a ratio of anatabine:nicotine of about 0.04; and a ratio of nornicotine:nicotine of about 0.05. Suitably, the *Nicotiana tabacum* plant is a non-naturally occurring or transgenic host *Nicotiana tabacum* plant comprising a heterologous ADC from *Nicotiana glauca* (NgADC1).

In another aspect, there is disclosed a dried or lyophilised green plant leaf harvested from a mature flowering *Nicotiana tabacum* plant comprising a ratio of anabasine:anatabine of about 0.25; or a ratio of anabasine:nornicotine of about 0.15; or a ratio of anabasine:nicotine of about 0.008; or a ratio of anatabine:nornicotine of about 0.62; or a ratio of anatabine:nicotine is about 0.03; or a ratio of nornicotine:nicotine of about 0.05; or a ratio of anabasine:anatabine of about 0.25; and a ratio of anabasine:nornicotine of about 0.15 and a ratio of anabasine:nicotine of about 0.008; and a ratio of nornicotine:nicotine of about 0.03; or a ratio of anabasine:anatabine of about 0.25; and a ratio of anatabine:nornicotine of about 0.62; and a ratio of anatabine:nicotine of about 0.03; and a ratio of nornicotine:nicotine of about 0.03. Suitably, the *Nicotiana tabacum* plant is a non-naturally occurring or transgenic host *Nicotiana tabacum* plant comprising a heterologous ADC from *Nicotiana glauca* (NgADC2).

In another aspect, there is disclosed a dried or lyophilised green plant leaf harvested from a mature flowering *Nicotiana tabacum* plant comprising a ratio of anabasine:anatabine of about 0.15; or a ratio of anabasine:nornicotine of about 0.08; or a ratio of anabasine:nicotine of about 0.004; or a ratio of anatabine:nornicotine of about 0.58; or a ratio of anatabine:nicotine is about 0.03; or a ratio of nornicotine:nicotine of about 0.05; or a ratio of anabasine:anatabine of about 0.15; or a ratio of anabasine:anatabine of about 0.15; and a ratio of anabasine:nornicotine of about 0.08 and a ratio of anabasine:nicotine of about 0.004; and a ratio of nornicotine:nicotine of about 0.05; or a ratio of anabasine:anatabine of about 0.15; and a ratio of anatabine:nornicotine of about 0.58; and a ratio of anatabine:nicotine of about 0.03; and a ratio of nornicotine:nicotine of about 0.05. Suitably, the *Nicotiana tabacum* plant is a non-naturally occurring or transgenic host *Nicotiana tabacum* plant comprising a heterologous ADC from *Nicotiana debneyi* (NdADC1).

The alkaloids can be extracted from *Nicotiana tabacum* host plants using methods described in the art (for example, see Jones, Bernado-Gil and Lourenco (2001) *Journal of AOAC International,* 84 (2): 309-316). Alkaloids are typically extracted by harvesting the plant material, extracting the alkaloids from the plant using a solvent, and filtering the solvent. The amount of solvent added is typically about 1:1 with the plant matter. The plant material may first be cured or dried and then homogenised or lyophilised into a powder. A typically example of a solvent is water mixed with lime ($Ca(OH)_2$) and extraction is carried out with organic solvents (such as ether or petroleum spirit), shaken with aqueous acid and allowed to separate. Alkaloid salts are then in the aqueous liquid, while impurities remain in the organic liquid. In a specific example, the solvent can be water or aqueous alcohol combined with a weak or dilute acid, such as water/methanol and shaken. The water/methanol can be in a 3:7 ratio. 1 quinolone may be added to the water/methanol as an internal standard. The mixture may then be filtered. The mixture is then shaken with chloroform or other organic solvents and the alkaloids precipitated by the addition of excess sodium bicarbonate or ammonia before filtration or by extraction with organic solvents. In an alternative, the alkaloids may be extracted using supercritical fluid extraction as described in Kim, Choi and Yoo (2001) Alkaloids: Chemical and Biological Perspectives, Edited by S. William Pelletier, Volume 15, pages 415-431 (2001).

Supercritical fluid extraction (SFE) possesses several advantages over traditional methods of extracting alkaloids, such as good selectivity, environmental safety, less or no use of organic solvents, and higher speed of extraction. The alkaloids may also be extracted using other methods that are known in the art-such as microwave, soxhlet, steam distillation or ultrasonic extraction as described in Jones et al., (2001) supra. Removal of the solvent from the desired alkaloids may be carried out by known processes, including, but not limited to, distillation, open-dish evaporation, reduced-pressure evaporation, rotary evaporation, vacuum, lyophilization, or a combination of methods thereof.

Isolation of specific alkaloids from the total alkaloid extraction may be achieved using methods known in the art-such as liquid chromatography, column chromatography comprising a reverse stationary phase, a normal stationary phase or combination thereof, high-performance liquid chromatography, ion-exchange chromatography, gel-permeation (molecular sieve) chromatography, affinity chromatography, paper chromatography, thin-layer chromatography, gas chromatography, dye-ligand chromatography, hydrophobic interaction chromatography, pseudoaffinity chromatography, or high-pressure liquid chromatography. The eluents containing the target alkaloids may then be collected for further processing, such as washing, filtering and drying.

Methods for determining the levels of each alkaloid or total alkaloids are known in the art. Such methods include, gas-liquid chromatography, high performance liquid chromatography, mass-spectrometry, ultra-high performance liquid chromatography (UHPLC), high-performance thin layer chromatography, gas chromatography/thermal energy analysis, liquid chromatography/mass spectrometry, ion chromatography, radio-immunoassays, and enzyme-linked immunosorbent assays. Methods for determining the levels of alkaloids are described in Sisson and Severson, 1990 supra, DeBoer et al., 2011 supra, Jones et al., 2001 supra, and Zhang et al. 2007. *J Am Soc Mass Spectrom,* 18:1774-1782). In a preferred example, measurement of each alkaloid or total alkaloids is performed using ultra high-performance liquid chromatography coupled to a mass spectrometer. In a preferred embodiment, UHPLC-MS analysis is used as described in Example 3 herein.

According to the present invention, a vector or expression vector comprising one or more heterologous ADC polynucleotides is disclosed that can be used to express the heterologous ADC in the *Nicotiana tabacum* host cell or plant or part thereof comprising the host cell and the like.

Various forms of expression are contemplated, including nuclear, chloroplast and transient expression.

Nuclear expression involves transcription in the nucleus and translation in the cytoplasm. It involves the expression of a heterologous polypeptide from the nuclear genome, typically introduced into the plant using either *Agrobacterium tumefaciens*-mediated transformation or biolistic gene gun-mediated transformation. A popular promoter is the CaMV 35S promoter from the cauliflower mosaic virus which is a strong constitutive promoter. A variety of polyadenylation sequences can be used-such as the *Agrobacterium tumefaciens* nos gene, the pea ssu gene and the cauliflower mosaic virus 35S transcript. Polyadenylation is one of the major factors determining expression levels and is important for export of mRNA from the nucleus and subsequent translation, as well as being a key element of mRNA stability.

Chloroplast expression is also contemplated, which involves the introduction of a transgene into the chloroplast genome using a particle gun. A transgene cassette can be created to insert a heterologous ADC gene into a spacer region between functional chloroplast genes, using two known flanking sequences in the chloroplast genome, via homologous recombination. This precise targeting can avoid placing the gene into a part of the genome which is poorly transcribed, ensuring a high level of expression. Transgenes are commonly integrated between the trnl-trnA genes in the rrn operon, as this is a transcriptionally active region that offers very high levels of gene expression. Commonly used sequences in plasmid gene vectors include the bacteriophage T7 gene 10 as a 5' untranslated region to enhance ribosome binding, the use of a 3' untranslated region to ensure transcript stability, and the use of a chloroplast promoter such as psbA.

Transient expression also allows the production of recombinant protein. In a first transient expression system, plant viruses such at the tobacco mosaic virus are used to introduce the transgene into an infected plant. In another transient expression method, *Agrobacterium* mediated transient gene expression introducing T-DNA into plant cells is used for high level expression.

The vector can be complexed with a delivery vehicle-such as a liposome, peptide or poloxamer, a viral vector (including adenoviruses, lentiviruses, retroviruses, Geminiviridae, bean yellow dwarf virus, cabbage leaf curl virus, tomato golden mosaic virus, wheat dwarf virus, sun hemp mosaic virus, potato virus X, tomato bushy stunt virus, tobacco mosaic virus, tobacco rattle virus, tobamovirus, Virgaviridae, and vectors derived therefrom), yeast artificial chromosome, episomes capable of extra-chromosomal replication, or phage (bacterial vectors). The vector may be single or double stranded, linearised or circular. The polynucleotide sequence in a vector can be in one of two possible orientations-sense (same) orientation or reverse (anti-sense) orientation—with respect to the orientation of a regulatory element positioned within the vector.

The at least one heterologous polynucleotide sequence encoding an ADC is operably linked to one or more regulatory elements. The regulatory element is typically located upstream (that is, 5') to the heterologous polynucleotide sequence and helps to regulate the expression thereof. The 'regulatory element' may be an enhancer, a transcriptional regulatory region, a termination region, or a promoter.

The promoter sequence can be 'constitutive', that is, a promoter that is continuously expressed throughout the life of the plant, and therefore allows continual transcription of the downstream heterologous polynucleotide sequence. The promoter can be 'inducible' in that it only allows transcription of the at least one heterologous polynucleotide sequence in certain circumstances. The promoter can be tissue specific, in which case the at least one heterologous polynucleotide sequence is expressed in a particular tissue.

Examples of constitutive promoters include carnation etched ring virus (CERV), *Mirabilis* Mosaic Virus (MMV), cauliflower mosaic virus (CaMV) 35S, SSU, OCS, lib4, usp, STLS1, B33, nos, ubiquitin-promoters, phaseolin-promoters, Actin 7 (from *Arabidopsis thalania*), double enhanced cauliflower mosaic virus promoter, AtSCPL30 (from *Arabidopsis thalania*), CAMV 19s, double 35S, MMV, and elF4A-10 (from *N. tabacum*) promoters. In embodiments the promoter may be a constitutive tobacco promoter-such as those described in European patent EP0938572. In embodiments, the promoter may be leaf specific, such as pyruvate, orthophosphate dikinase (PPDK) from the C4 plant (maize), cab-m1Ca+2 promoter from maize, the *Arabidopsis thaliana* myb-related gene promoter (Atmyb5), the ribulose biphosphate carboxylase (RBCS) promoters (such as RBCS1, RBCS2 and RBCS3A genes from tomato). In embodiments, the promoter may be root-specific such as NtREL1 from tobacco (Zhang et al. 2016. *Plant Cell Reports,* 35, 757-769), the tobacco RB7 promoter (U.S. Pat. No. 5,459,252), maize promoter CRWAQ81 (US published patent application Ser. No. 20/050,097633); the *Arabidopsis* ARSKI promoter (Hwang and Goodman (1995) *Plant J.* 8:37-43), the maize MR7 promoter (U.S. Pat. No. 5,837,848), the maize ZRP2 promoter (U.S. Pat. No. 5,633,363), the maize MTL promoter (U.S. Pat. Nos. 5,466,785 and 6,018,099) the maize MRSI, MRS2, MRS3, and MRS4 promoters (U.S. patent application No. 20050010974), or an *Arabidopsis* cryptic promoter (U.S. Pat. No. 7,674,893).

In one embodiment, the promoter is the constitutive MMV promoter.

Examples of termination regions include *Agrobacterium tumefaciens* nopaline synthase terminator (nos), *Agrobacterium tumefaciens* mannopine synthase terminator (Tmas), CaMV 35S terminator (T35S), pea ribulose bisphosphate carboxylase small subunit termination region (TrbcS) or the Tnos termination region.

The vector may additionally comprise or contain a 'selection marker' or 'detectable agent' that permits the selection of, or screening for a plant cell, plant or part thereof containing the selection marker or detectable agent. The selection marker or detectable agent may be a sequence encoding antibiotic or herbicide resistance. The selection marker or detectable agent may be one or more of adenosine deaminase, dihydrofolate reductase, hygromycin-B-phosphotransferase, thymidine kinase, xanthine-guanine phospho-ribosyltransferase, chlorsulfuron, phosphinothricin, glyphosate and glufosinate resistance, and amino-glycoside 3'-O-phosphotransferase. Selection markers may confer resistance to G418, hygromycin, tetracyclin, bleomycin, kanamycin, neomycin, or gentamicin. The construct may also contain a selection marker or detection agent comprising a gene that confers resistance to herbicidal phosphinothricin analogs like ammonium gluphosinate (Thompson et al, EMBO J 9:2519-23 (1987)). In embodiments the selection marker or detectable agent may be a green fluorescent protein (GFP), luciferase, beta-glucuronidase, glutathione S-transferase, polyhistidine, c-myc, hemaglutinin.

Other nucleic acid sequences encoding additional functional elements may also be present as known in the art. These may include replication sequences, or T-DNA sequences, for example.

An exemplary vector for use in the present invention is a GATEWAY vector (Karimi M, Inzé D, Depicker A. GATEWAY vectors for *Agrobacterium*-mediated plant transformation. *Trends Plant Sci.* (2002) May; 7 (5): 193-5) containing the MMV promoter and a 3' nos terminator sequence of the nopaline synthase gene of *Agrobacterium tumefaciens*. The heterologous sequences are flanked between MMV and the 3' nos terminator sequence.

The use of promoters having different strengths is also contemplated herein as the amount of heterologous polypeptide that is expressed may alter the levels of one or more alkaloids. MMV promoter is a very strong promoter, like the 35S promoter. The MMV promoter is described in *Plant Mol Biol.* (1999) July; 40 (5): 771-82. The 35S promoter is described in *Current Plant Biology* (2020), Volume 24. As known in the art, there are a number of methods of introducing polynucleotides or polypeptides or vectors or constructs and the like into a plant cell, plant or part thereof. Such methods may include infiltration with bacteria (such as *Agrobacterium, Rhizobium, Sinorhizobium*, or *Mesorhizobium*), freeze-thaw method, leaf-disc transformation, viral-vector mediated transformation, sonication, microinjection, plant virus-mediated transfer, wound inoculation, particle bombardment, electroporation, direct gene transfer (also referred to as direct DNA uptake), genome editing (including CRISPR (Plant Methods (2016) 12:8; and *Front Plant Sci.* 20 (2016) 7:506), TALENS, zinc finger nucleases), biolistic methods, cationic lipid-mediated transfection or polyethylene glycol-assisted protoplast transformation. Such methods are well known in the art and are described in Davey and Anthony (2010) Plant cell culture: essential methods. Wiley-Blackwell, Gallois and Marinho (1995) Leaf disc transformation using *Agrobacterium tumefaciens*. In: Jones (eds). Plant Gene Transfer and Expression Protocols. Methods in Molecular Biology, 49. *Springer*, and Smith (2013) Plant tissue culture: techniques and experiments. 3rd edition. Elsevier Inc. The host plant can be transformed as a whole plant, for example, by submersion in a medium comprising *Agrobacterium tumafaciens* and placed under a vacuum. The vacuum can be between 40-400 mbar and for between 30 to 60 seconds. The vacuum can be at 50,100,150, 200, 250, 300, 350 or 400 mbar. The vacuum can be applied for 30, 40, 50 or 60 seconds. The host plant is then produced by transforming a plant cell or leaf disc using standard techniques in the art, and then regenerating the plant cell or leaf disc into a plant.

Successful insertion of a heterologous polynucleotide into the host may be detected using methods standard in the art, and include, but are not limited to, methods such as sequencing (such as Sanger sequencing or next-generation sequencing), or microarrays. Expression of a heterologous polynucleotide may be detected by methods standard in the art, and include, but are not limited to, PCR (including RT-PCR, and real time PCR), Northern blotting, in-situ hybridisation, nuclease protection assays, RNA microarrays, Western blotting, enzyme-based immunosorbent assays, dot blotting, immunocytochemistry, immunohistochemistry, mass spectrometry, high-performance liquid chromatography, affinity chromatography, gel-filtration chromatography, ion-exchange chromatography, liquid chromatography, liquid chromatography-mass spectrometry, or immunoprecipitation. PCR may be carried out using one or more primers. Exemplary primers comprise, consist or consist essentially of SEQ ID NOs: 7-12, preferably pairing SEQ ID NOs: 7 and 8, 9 and 10 or 11 and 12. Alternatively, primers or probes may comprise a sequence complementary to at least 10, 15, 17, 18, 19, 20, 21, 22, 25, 30, 50, or 100 nucleotides of SEQ ID NOs: 1, 3 or 5.

In a further aspect, there is also provided a method of detecting a heterologous polynucleotide(s) as described herein in a sample, said method comprising (a) providing a sample comprising, or suspected of comprising, the polynucleotide of interest; (b) contacting said sample with one or more primers or one or more probes for specifically detecting at least a portion of the polynucleotide(s); and (c) detecting the presence of an amplification product, wherein the presence of an amplification product is indicative of the presence of the polynucleotide(s) in the sample.

In a further aspect, there is also provided the use of one or more primers or probes for specifically detecting at least a portion of the polynucleotide(s) described herein.

Kits for detecting at least a portion of the polynucleotide(s) described herein are also provided which comprise one or more primers or probes for specifically detecting at least a portion of the polynucleotide(s). The kit may comprise reagents for polynucleotide amplification-such as PCR—or reagents for probe hybridization-detection technology—such as Southern Blots, Northern Blots, in-situ hybridization, or microarray. The kit may comprise reagents for antibody binding-detection technology such as Western Blot, ELISA, SELDI mass spectrometry or test strips. The kit may comprise reagents for DNA sequencing. The kit may comprise reagents and instructions for using the kit. To facilitate detection of amplification products, the one or more primers or probes may be labelled using any conventional labelling method. The presence of the heterologous polypeptide may be determined by methods including, but not limited to, Western blotting, enzyme-based immunosorbent assays, dot blotting, immunocytochemistry, immunohistochemistry, mass spectrometry, high-performance liquid chromatography, affinity chromatography, gel-filtration chromatography, ion-exchange chromatography, liquid chromatography, liquid chromatography-mass spectrometry, or immunoprecipitation.

Modified alkaloid content, effected in accordance with the present invention, can be combined with other traits of interest-such as disease resistance, pest resistance, high yield or other desirable commercially acceptable genetic background. Accordingly, the presently described host plant cells, plants or parts thereof may also be transformed or transfected with polynucleotides or polypeptides conferring other traits of interest to obtain host cells with more than one desirable characteristic. Alternatively, a stable non-naturally occurring or transgenic plant comprising the transgenic or non-naturally occurring host cell as disclosed herein may be crossed or introgressed with another cultivar, variety or species with a desirable trait to obtain progeny (plants) with more than one desirable characteristic.

One or more of the following further genetic modifications (for example, mutations) can be present in the plants and parts thereof—including modification in one or more genes that are involved in the conversion of nitrogenous metabolic intermediates resulting in lower levels of at least one tobacco-specific nitrosamine (TSNA); modification of one or more genes that are involved in heavy metal uptake or heavy metal transport resulting in lower heavy metal content; modification of isopropylmalate synthase which results in a change in sucrose ester composition which can be used to alter flavour profile (see WO2013029799); modification of threonine synthase in which levels of methional can be modulated (see WO2013029800); modification of neoxanthin synthase, lycopene beta cyclase or 9-cis-epoxy-carotenoid dioxygenase to modulate beta-damascenone content to alter flavour profile (see WO2013064499); modification of the CLC family of chloride channels to modulate nitrate levels therein (see WO2014096283 and WO2015197727); modification of asparagine synthetase to modulate levels of asparagine in leaf and modulated levels of acrylamide in aerosol produced upon heating or combusting the leaf (see WO2017042162). Other traits of interest may include alternative means of altering alkaloid levels. For example, the plant cell, plant or part thereof, tobacco product or smoking article may also comprise a modification in one or more N-demethylases to further alter the levels of nornicotine and metabolites of nornicotine during curing or drying (WO2015/169927). In embodiments, the expression or function of one or more genes involved in synthesising nicotine may also be altered, such as A622, BBLa, BBLb, JRESL 1, JRE5L2, MATE1, MATE 2, MPO1, MPO2, MYC2a, MYC2b, NBB1, nic1, nic2, NUP1, NUP2, PMT1, PMT2, PMT3, PMT4 or QPT. In embodiments, the expression or function of one or more genes involved in modulating the levels of alkaloids may also be altered, such as BBLa, BBLb, JRESL 1, JRE5L2, MATE1, MATE 2, MYC2a, ODC, MYC2b, nic1, nic2, NUP1 or NUP2.

The present disclosure also relates to methods of producing the non-naturally occurring or transgenic host plant cell described herein. The method may comprise (a) providing a host plant cell; and (b) modifying said host plant cell to comprise at least one heterologous polynucleotide or polypeptide as described herein or a construct, vector or expression vector comprising a heterologous ADC polynucleotide as described herein. In embodiments, the method of modifying the plant cell (b) may include but are not limited to bacterial infiltration (such as *Agrobacterium, Rhizobium, Sinorhizobium*, or *Mesorhizobium*), particle bombardment, electroporation, direct gene transfer, freeze-thaw, viral-vector mediated transformation, sonication, microinjection, plant virus-mediated transfer, wound inoculation, biolistic methods, cationic lipid-mediated transfection or polyethylene glycol-assisted protoplast transformation. In embodiments, the plant cell may then be regenerated into a host plant. In embodiments the plant is then propagated and optionally plant material is harvested from the plant. In embodiments, the plant material is cured or dried. In embodiments, the plant material is air cured, fire cured, smoke cured, flue cured or sun cured. In embodiments, the plant material, including the cured or dried plant material, is incorporated into a tobacco product or smoking article. Therefore, the present disclosure describes methods for producing a host plant cell, plant or part thereof (including plant material and cured or dried plant material), tobacco products and smoking articles with altered levels of one or more alkaloids, or total alkaloids. The present disclosure also describes methods for altering the levels of one or more alkaloids, or total alkaloids in *Nicotiana tabacum* plants using the method described herein.

The present disclosure also relates to alternative methods of producing the non-naturally occurring or transgenic host plant described herein. The alternative method may comprise (a) providing a host plant; (b) transforming the plant with bacteria comprising at least one heterologous polynucleotide disclosed herein; and (c) propagating the plant. In embodiments, the method of transforming (b) involves submerging the plant in a medium comprising bacteria comprising the heterologous polynucleotide. In embodiments the method of transforming (b) involves syringe, wound transfer or vacuum infiltration. The bacteria may include, but are not limited to, *Agrobacterium, Rhizobium, Sinorhizobium*, or *Mesorhizobium*. The method may further comprise (d) harvesting plant material from the plant. In embodiments, the plant material is cured or dried. In embodiments, the plant material is air cured, fire cured, smoke cured, flue cured or sun cured. In embodiments, the plant material, including the cured or dried plant material, may be incorporated into a tobacco product or smoking article. Therefore, the present disclosure describes methods for producing a host plant or part thereof (including plant material and cured or dried plant material), tobacco products and smoking articles with altered levels of one or more alkaloids or total alkaloids. The present disclosure also describes methods for altering the levels of one or more alkaloids, or total alkaloids in *Nicotiana tabacum* plants using the method described herein.

In a particular aspect, there is disclosed a method for producing the non-naturally occurring or transgenic host *Nicotiana tabacum* plant cell described herein, said method comprising: (a) providing a host plant cell from a *Nicotiana tabacum* plant; (b) modifying said host *Nicotiana tabacum* plant cell to comprise at least one of: (i) a heterologous polynucleotide comprising, consisting, or consisting essentially of a polynucleotide sequence having at least 96% sequence identity to SEQ ID NO: 1, or at least 97% sequence identity to SEQ ID NO: 3; or (ii) a heterologous polypeptide encoded by the polynucleotide set forth in (i); or (iii) a heterologous polypeptide comprising, consisting or consisting essentially of a polypeptide sequence having at least 97% sequence identity to SEQ ID NO: 2, at least 97.5% sequence identity to SEQ ID NO: 4; or (iv) a construct, vector or expression vector comprising the heterologous polynucleotide of (i), suitably wherein the heterologous polynucleotide is operably linked in the construct, vector or expression construct to a regulatory element, more suitably wherein the regulatory element is a promoter; or (v) a heterologous polynucleotide comprising, consisting, or consisting essentially of a polynucleotide sequence having at least 96.5% sequence identity to SEQ ID NO: 5; or (vi) a heterologous polypeptide encoded by the polynucleotide set forth in (v); or (vii) a heterologous polypeptide comprising, consisting or consisting essentially of a polypeptide sequence having at least 97.5% sequence identity to SEQ ID NO: 6; or (viii) a construct, vector or expression vector comprising the heterologous polynucleotide of (v), suitably wherein the heterologous polynucleotide is operably linked in the construct, vector or expression construct to a regulatory element, more suitably wherein the regulatory element is a promoter; wherein said heterologous polynucleotide or polypeptide encodes an arginine decarboxylase (ADC).

Steps of each method disclosed herein may be performed in any order. In preferred embodiments, the steps of the methods disclosed herein may be performed in the order in which they appear, that is, (a), then (b) then (c) etc.

Any suitable method for regenerating or growing a plant from a plant cell or plant tissue may be used, such as, tissue culture or regeneration from protoplasts. Suitably, plants may be regenerated by growing transformed plant cells on callus induction media, shoot induction media or root induction media. See, for example, Negrutiu (1992) In Linsey (eds). Plant Tissue Culture Manual: 213-223; Hsu et al. 2020. *Frontiers in Genome Editing,* 2:39, and Shoyeb et al. 2020. *Current Journal of Applied Science and Technology,* 39 (32): 1-9. The plants may then be grown, and either pollinated with the same transformed strain or different strains, and the resulting hybrid having expression of the desired characteristic identified. Two or more generations may be grown to ensure that expression of the desired characteristic is stably maintained and inherited and then seeds harvested and analysed using methods for detecting polynucleotide insertion/expression or alkaloid levels as described herein to ensure expression of the desired characteristic has been achieved.

Methods of asexually propagating plants are well known in the art, and include, but are not limited to stem, leaf, and tip cuttings, layering, division, budding and grafting. Methods of sexual propagation include seed propagation. Such sexual propagation methods may comprise (a) crossing the transgenic or non-naturally occurring plant with a second plant to yield progeny tobacco seed; and (b) growing the progeny seed under plant growth conditions to yield the transgenic or non-naturally occurring plant. In embodiments the progeny may be crossed with itself, the parent plant or another plant, and this process repeated to generate further generations of the transgenic or non-naturally occurring plants.

In another embodiment, the expression or activity of the endogenous ADC in the host *Nicotiana tabacum* plant cell is reduced or inactivated. This may reduce or eliminate interference from the endogenous ADC in the host *Nicotiana tabacum* plant cell. An adverse phenotype which is associated with completely silencing ADC would be avoided since ADC activity would still be provided by the heterologous ADC. The expression or activity of the endogenous ADC can be reduced or inactivated using various methods that are well known in the art-such as by breeding genome modified lines via techniques-such as CRISPR, TALENS, ZFN, silencing (RNAi, miRNA), or mutagenesis and the like. A preferred method involves the use of the bacterial CRISPR/Cas system. CRISPR/Cas technology was implemented in plants in the method of WO 2015/189693, which discloses a viral-mediated genome editing platform that is broadly applicable across plant species. In the context of the present disclosure, a guide RNA may be derived from any of the sequences disclosed herein and the teaching of WO2015/189693 applied to edit the genome of a plant cell. The fast pace of the development of the technology has generated a great variety of protocols with broad applicability in plantae, which have been well catalogued in a number of recent scientific review articles (for example, *Plant Methods* (2016) 12:8; and *Front Plant Sci*. (2016) 7:506). A review of CRISPR/Cas systems with a particular focus on its application is described in *Biotechnology Advances* (2015) 33, 1, 41-52. More recent developments in the use of CRISPR/Cas for manipulating plant genomes are discussed in *Acta Pharmaceutica Sinica* B (2017) 7, 3, 292-302 and *Curr. Op. in Plant Biol*. (2017) 36, 1-8. Another preferred method involves the use of mutagenesis, including site-directed mutagenesis, oligonucleotide-directed mutagenesis, chemically-induced mutagenesis, irradiation-induced mutagenesis, mutagenesis utilizing modified bases, mutagenesis utilizing gapped duplex DNA, double-strand break mutagenesis, mutagenesis utilizing repair-deficient host strains, mutagenesis by total gene synthesis, DNA shuffling and the like. Methods that introduce mutations randomly in a polynucleotide can include chemical mutagenesis and radiation mutagenesis. Chemical mutagenesis involves the use of exogenously added chemicals-such as mutagenic, teratogenic, or carcinogenic organic compounds—to induce mutations. Mutagens that create primarily point mutations and short deletions, insertions, missense mutations, simple sequence repeats, transversions or transitions, including chemical mutagens or radiation, may be used to create the mutations. Mutagens include ethyl methanesulfonate, methylmethane sulfonate, N-ethyl-N-nitrosurea, triethylmelamine, N-methyl-N-nitrosourea, procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine, nitrosoguanidine, 2-aminopurine, 7,12 dimethyl-benz (a) anthracene, ethylene oxide, hexamethylphosphoramide, bisulfan, diepoxyalkanes (diepoxyoctane, diepoxybutane, and the like), 2-methoxy-6-chloro-9 [3-(ethyl-2-chloro-ethyl)aminopropylamino]acridine dihydrochloride and formaldehyde. Methods that introduce one or more targeted mutations into a polynucleotide sequence include but are not limited to genome editing technology, particularly zinc finger nuclease-mediated mutagenesis, tilling (targeting induced local lesions in genomes), homologous recombination, oligonucleotide-directed mutagenesis, and meganuclease-mediated mutagenesis.

The present invention also relates to methods of producing one or more alkaloids of interest—such as one or more of nicotine, nornicotine, anabasine and anatabine-said method comprising: (a) providing a host plant cell; (b) modifying said host plant cell to comprise at least one heterologous ADC polynucleotide or polypeptide as described herein or a construct, vector or expression vector comprising the at least one heterologous ADC polynucleotide or polypeptide as described herein; (c) regenerating the host plant cell into a plant; (d) propagating the plant; (e) harvesting the plant material; (f) homogenising the plant material; and (g) extracting one or more alkaloids of interest from the homogenised plant material.

The method of modifying the plant cell may include but are not limited to bacterial infiltration (such as *Agrobacterium, Rhizobium, Sinorhizobium*, or *Mesorhizobium*), particle bombardment, electroporation, direct gene transfer, freeze-thaw, viral-vector mediated transformation, sonication, microinjection, plant virus-mediated transfer, wound inoculation, biolistic methods, cationic lipid-mediated transfection or polyethylene glycol-assisted protoplast transformation.

The plant material may be cured or dried, suitably air cured, fire cured, smoke cured, flue cured or sun cured.

In embodiments, the method of homogenising the plant material includes, but is not limited to, mechanical grinding methods-such as a bead beater, mill, blender, or mortar and pestle. Methods for the extraction of the alkaloids as already described herein may be used. In embodiments the method further comprises: (h) separating or purifying one or more alkaloids. Methods for achieving such separation or purification are described herein.

The present invention also relates to alternative methods of producing one or more alkaloids—such as one or more of nicotine, nornicotine, anabasine and anatabine-said method comprising (a) providing a host plant; (b) transforming the plant with bacteria comprising at least one heterologous polynucleotide disclosed herein; (c) propagating the plant; (d) harvesting the plant material; (e) homogenising the plant material; and (f) extracting alkaloids from the homogenised plant material. In embodiments, the method of transforming (b) involves submerging the plant in a medium comprising bacteria comprising at least one heterologous polynucleotide as disclosed herein. In embodiments the method further comprises: (g) separating or purifying one or more alkaloids from the others.

A tobacco product or smoking article comprising a part of the *Nicotiana tabacum* plant or the *Nicotiana tabacum* plant material as described herein is also disclosed. Parts of the plants and plant material as described herein and more particularly the leaf lamina and midrib of *Nicotiana tabacum* plants, can be incorporated into or used in making various consumable products including but not limited to aerosol forming materials, aerosol forming devices, smoking articles, smokable articles, smokeless products, and tobacco products. Examples of aerosol forming materials include but are not limited to tobacco compositions, tobaccos, tobacco extract, cut tobacco, cut filler, cured or dried tobacco, expanded tobacco, homogenized tobacco, reconstituted tobacco, and pipe tobaccos. Smoking articles and smokable articles are types of aerosol forming devices. Examples of smoking articles or smokable articles include but are not limited to cigarettes, cigarillos, and cigars. Examples of smokeless products comprise chewing tobaccos, and snuffs. In certain aerosol forming devices, rather than combustion (or burning), a tobacco composition or another aerosol forming material is heated, for example, by one or more electrical heating elements or a carbon heat source to produce an aerosol. Typically, in such heated smoking articles, an aerosol is generated by the transfer of heat from a heat source to a physically separate aerosol-forming substrate or material, which may be located within, around or downstream of the heat source. During smoking, volatile compounds are released from the aerosol-forming substrate by heat transfer from the heat source and entrained in air drawn through the smoking article. As the released compounds cool, they condense to form an aerosol that is inhaled by the user. Such devices include, for example, electrically heated aerosol-generating devices in which an aerosol is generated by the transfer of heat from of the aerosol-generating device to the aerosol-forming substrate of a heated smoking article. Suitably, during heating of the aerosol-forming substrate, combustion or burning of the tobacco does not occur. A suitable aerosol forming article is described in WO2013/098405 and comprises an aerosol-forming substrate for generating an inhalable aerosol when heated by an internal heating element of an aerosol-generating device. It can comprise an electrically heated aerosol-generating device comprising an internal heating element. It can further comprise, in a linear sequential arrangement, an aerosol-forming substrate, a support element located immediately downstream of the aerosol-forming substrate, an aerosol-cooling element located downstream of the support element, and an outer wrapper circumscribing the aerosol-forming substrate, the support element and the aerosol-cooling element. The support element can abut the aerosol-forming substrate. The aerosol-forming substrate is penetrable by the heating element of the aerosol-generating device. In another type of heated aerosol forming device, an aerosol is produced by the transfer of heat from a combustible fuel element or heat source to a physically separate aerosol forming material, which may be located within, around or downstream of the heat source. Smokeless tobacco products and various tobacco-containing aerosol forming materials may contain tobacco in any form, including as dried particles, shreds, granules, powders, or slurry, deposited on, mixed in, surrounded by, or otherwise combined with other ingredients in any format, such as flakes, films, tabs, foams, or beads. 'Smoke' is used to describe a type of aerosol that is produced by smoking articles, such as combustible cigarettes, or by combusting an aerosol forming material.

The invention is further described in the Examples below, which are provided to describe the invention in further detail. These examples, which set forth a preferred mode presently contemplated for carrying out the invention, are intended to illustrate and not to limit the invention.

EXAMPLES

Example 1—Identifying ADC Genes in *N. glauca* and *N. debneyi*

Methods

RNA was extracted from *N. debneyi* and *N. glauca* roots using RNeasy Qiagen Plant Mini Kit following manufacturer instructions. The transcriptome was then partially sequenced using the Illumina short-reads sequencing technology. The sequences of the ADC genes in *N. glauca* and *N. debneyi* were identified by aligning the *N debneyi* and *N. glauca* sequencing data to sequences of NtADC1-S(SEQ ID NO: 13), NtADC1-T (SEQ ID NO: 15), NtADC2-S(SEQ ID NO: 17) and NtADC2-T (SEQ ID NO: 19) from *N. tabacum* using Burrows-Wheeler Aligner (BWA; see Li H. and Durbin R. (2009) Bioinformatics, 25:1754-60).

The protein sequences were deduced by converting the codons from the coding regions of the identified ADC genes to amino acids using the standard genetic code. The deduced protein sequences were then aligned with the amino acid ADC sequences of *N. tabacum* (SEQ ID NOs: 14, 16, 18 and 20), tomato (Solyc10g054440) and *Arabidopsis* (AtADC1 and AtADC2) using MUSCLE alignment as described in Edgar (2004) BMC Bioinformatics, 5:113. SIFT, Scale-Invariant Feature Transform, was performed using methods previously described in the art (Kumar et al. (2009) supra). SIFT predicts whether an amino acid substitution affects protein function based on sequence homology and the physical properties of amino acids. SIFT can be applied to naturally occurring nonsynonymous polymorphisms and laboratory-induced missense mutations.

Results

Alignment resulted in the identification of two ADC genes in *N. glauca*; one in the ADC1 cluster (referred to herein as 'NgADC1') and one in the ADC2 cluster (referred to herein as 'NgADC2'). Only one ADC gene was identified in *N. debneyi* which aligned with the ADC1 cluster (referred to herein as 'NdADC1'). The sequence alignment indicated that all ADC sequences, including the ones of Tomato and *Arabidopsis*, started with the amino acids 'MPAL'. In the middle of the sequences, at position 254, another consensus signature sequence of 29 amino acids was found to be present 'IGLRAKLRTKHSGHFGSTSGEKGKFGLTT', and was identified as also being common to ADC proteins from *Brassica napus, Spinacia oleracea, Solanum tuberosum, Nicotiana attenuate, Capsicum annuum, Datura stramonium, Cannabis sativa, Gossypium hirsutum.*

However, the alignment identified differing amino acids in the protein sequences of ADCs from *N. tabacum* (including the two sequences originating from the ancestors *N. sylvestris* and *N. tomentosiformis*), *N. glauca* or *N. debneyi.*

There were 14 amino acid changes in NgADC1 (SEQ ID NO: 2) compared to the *N. tabacum* gene product. The changed amino acids are located at the following positions in NgADC1 (SEQ ID NO: 2): 31G, 40L, 63C, 296E, 355S, 417S, 429Y, 438S, 652M, 658D, 661M, 700D, 707I, and 730V.

There were 9 amino acid changes for NgADC2 compared to the *N. tabacum* gene product. The changed amino acids are located at the following positions in NgADC2 (SEQ ID NO: 4): 12A, 371, 87M, 151F, 317V, 378E, 429V, 530V, and 680V.

There were 13 amino acid changes for NdACD1 compared to the *N. tabacum* gene product. The changed amino acids are located at the following positions in NdACD1 (SEQ ID NO: 6): 90M, 203F, 296E, 342V, 380Q, 441G, 619N, 628S, 663D, 664H, 680L, 698S, and 715S.

These amino acid changes are not expected to change the three-dimensional structure or core of the ADC as the SIFT scores remained in all cases high (not below 0.1). Nevertheless, the amino acid changes suggested that there may be altered functions between the proteins, particularly with regard to the interactions of the protein with the substrate, and may explain the differences in alkaloid levels between *N. debneyi, N. glauca* and *N. tabacum* (see Table 2).

Example 2—Producing *N. tabacum* Overexpressing Heterologous ADCs

Methods

The coding sequence (CDS) of NgADC1 (SEQ ID NO: 1), NgADC2 (SEQ ID NO: 3) or NdADC1 (SEQ ID NO:5) was cloned with the constitutive *Mirabilis* Mosaic Virus (MMV) promoter into a GATEWAY pENTR221 vector (ThermoFisher Scientific, 168 Third Avenue, Waltham, MA, USA). The NgADC1, NgADC2 or NdADC1 gene sequences were flanked between MMV and the 3' nos terminator sequence of the nopaline synthase gene of *Agrobacterium tumefaciens* in the GATEWAY pENTR221 vector. The constructs were then transformed into *A. tumefaciens* using heat shock and cultured overnight on LB medium supplemented with antibiotics.

*N. tabacum* TN90 (Burley) cultivars were then transformed using standard *Agrobacterium*-mediated transformation protocols. Briefly, *N. tabacum* plant tissues were submerged in the transformed *A. tumefaciens* suspended in distilled water and a 100 mbar vacuum applied for 60 seconds. Plants were then grown for 5-7 days under normal growth conditions.

To measure the expression of the MMV-NgADC1, MMV-NgADC2 and MMV-NdADC1 constructs, random leaf samples were collected from the TO plants around 5 to 7 days after transformation and lyophilised in liquid nitrogen to form a fine powder. RNA extraction was then performed using the RNeasy mini kit (Qiagen) according to the manufacturer instructions. Reverse transcription was performed to convert RNA into complementary DNA (cDNA) using Superscript IV reverse transcriptase (Thermo Fisher Scientific) following manufacturer instructions. Quantitative real-time PCR was then performed using primer pairs corresponding to SEQ ID NOs: 7 and 8 for NgADC1, SEQ ID NOs: 9 and 10 for NgADC2, and SEQ ID NOs: 11 and 12 for NdADC1. The PCRs were performed under the following reaction conditions: 95° C. for 15 minutes, followed by 50 cycles of 95° C. for 15 seconds (denaturation), 60° C. for 15 seconds (annealing) and 72° C. for 25 seconds (elongation).

Results

After transformation, expression of NgADC1, NgADC2 and NdADC1 constructs were measured in the flowers of single TO MMV::NgADC1, MMV::NgADC2 and MMV::NdADC1 plants (see FIG. 1). The level of expression of the inserts shown in FIG. 1 demonstrates that these TO plants were correctly transformed. Controls were *N. tabacum* plants transformed with 'empty' vectors (that is, not expressing an ADC). No changes to visual phenotype were observed in TO plants, nor the T1 growing plants, as compared to the control.

Example 3—Levels of Alkaloids in *N. tabacum* Overexpressing Heterologous ADCs

Methods

Green leaves of mature, flowering TO plants (about 3 months after transplantation in pots) were picked at the B-T position on the stalk (upper stalk position) and lyophilised in liquid nitrogen to form a fine powder. To measure the alkaloids, UHPLC-MS analysis was performed. First, alkaloids were extracted from 25 mg of the fine powder using an extraction mixture of water/methanol (3:7 ratio, with 500 ng mL-1 quinoline as internal standard; 5 mL) and agitating on a rotary shaker for 48 hours. The mixture was then filtered (Fisherbrand™ Sterile PES Syringe Filter with pore size of 0.2 μm) and diluted 1:50 with the extraction mixture. A simultaneous determination of alkaloids was performed on an Ultimate 3000 UHPLC system coupled to a Q-Exactive mass spectrometer (Thermo Fisher Scientific, Waltham, MA USA). Chromatographic separation was performed on an Acquity HSS T3 column (1.7 μm; 100×2.1 mm; Waters, Milford, MA USA) with the column temperature set to 45° C. Eluents were ammonium acetate in water (10 mM; pH=8.9; eluent A) and ammonium acetate in methanol (10 mM; eluent B) applied as a gradient (0 min, 10% B; 0.25 min, 10% B; 4.25 min, 98% B; 5.25 min, 98% B; flow: 0.5 mL·min-1). The injection volume was 5 μL. Nicotine, anabasine, myosmine, nornicotine, cotinine, anatabine, and quinoline eluted after 3.89, 3.27, 3.47, 2.76, 2.62, 3.36, and 4.04 min, respectively, and were detected as [M+H]+ pseudomolecular ions after positive electrospray ionization.

Results

The levels of nicotine, nornicotine, anabasine and anatabine were measured in lyophilized green leaves of mature, flowering TO *N. tabacum* overexpressing NgADC1 (OE-NgADC1), NgADC2 (OE-NgADC2) or NdADC1 (OE-NADC1) and their respective controls. The results are shown in Table 3.

Figure 2:
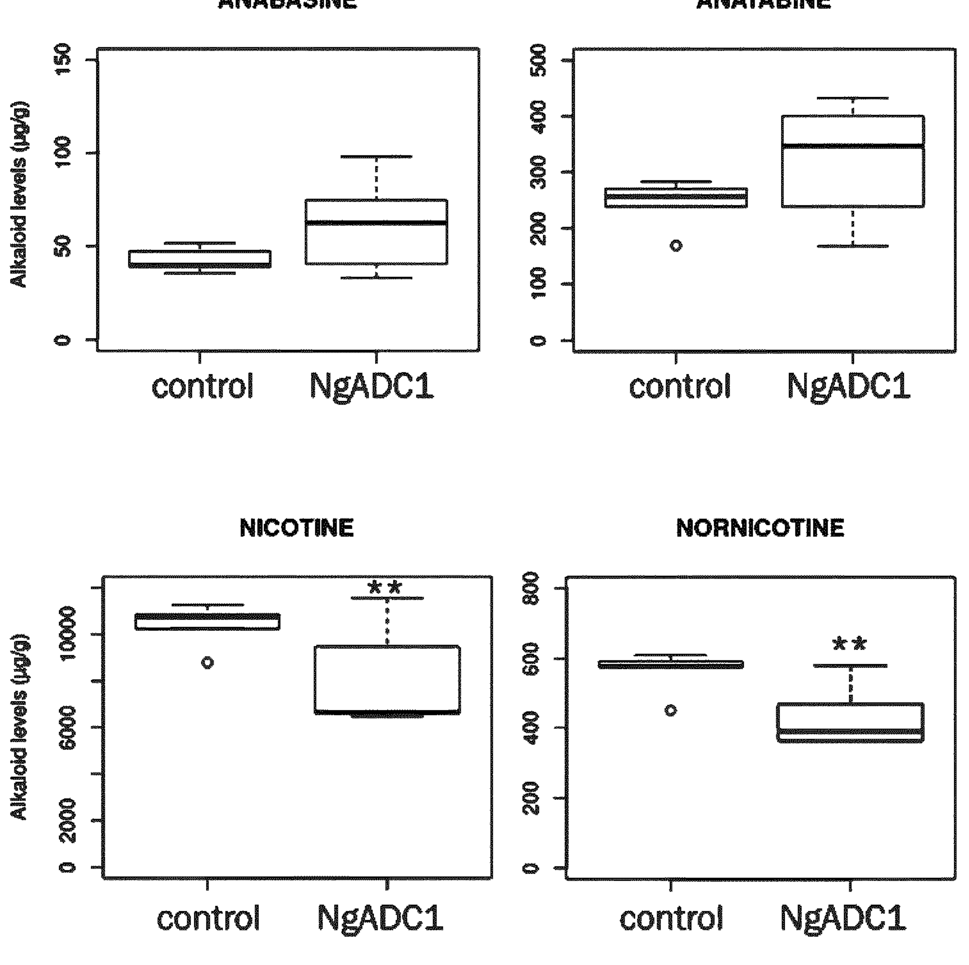
FIG. 2 is a series of graphs showing the overexpression of NgADC1 in TN90 (T0) plants. n=5, t-test, *p<0.05, **P<0.01. Significant reduction of nicotine ~26%. Significant reduction of nornicotine ~24%.

As demonstrated in FIG. 2, overexpressing NgADC1 in *N. tabacum* resulted in a significant (P<0.01) reduction of nicotine (reduced by 26%) and nornicotine (reduced by 24%) in the TO plants as compared to the control. A slight, but non-significant increase of anabasine and anatabine was also observed as compared to the control.

Figure 3:
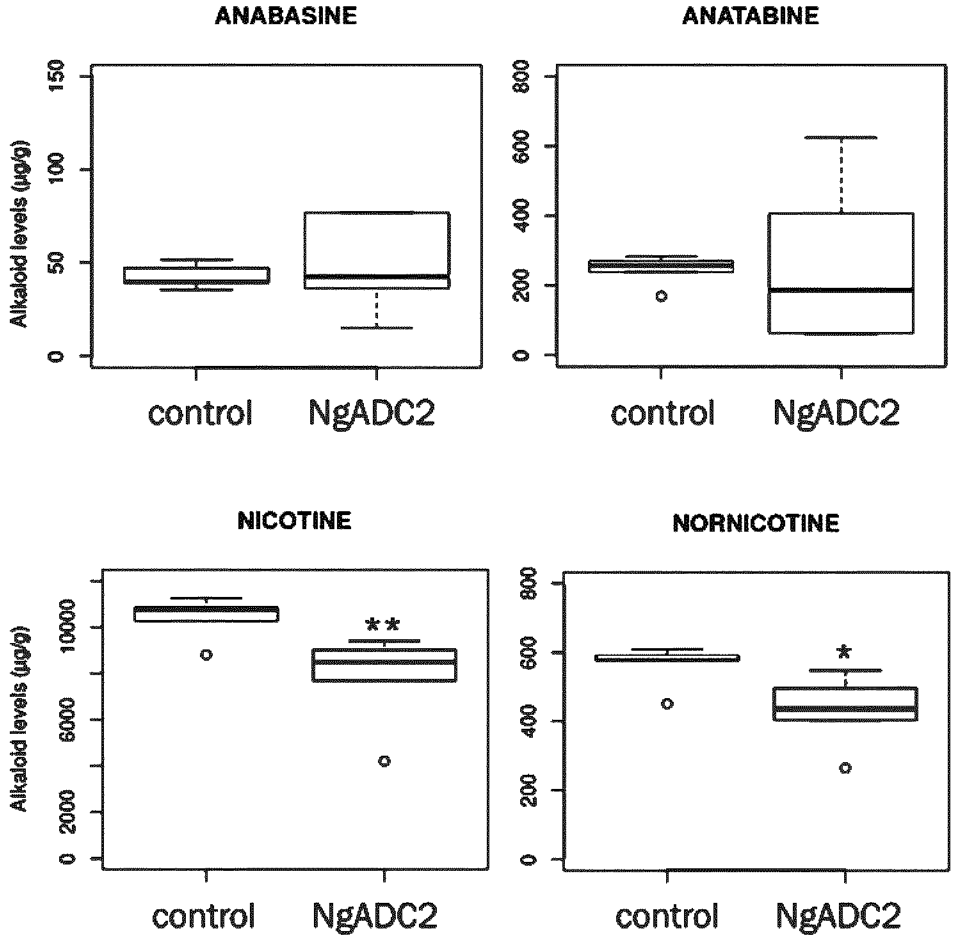
FIG. 3 is a series of graphs showing the overexpression of NgADC2 in TN90 (T0) plants. n=5, t-test, *p<0.05, **P<0.01. Significant reduction of nicotine ~27%. Significant reduction of nornicotine ~25%.

As demonstrated in FIG. 3, overexpressing NgADC2 in *N. tabacum* also resulted in a significant (P<0.05) reduction of nicotine (reduced by 27%) and nornicotine (reduced by 25%) in the T0 plants as compared to the control. No impact on anabasine and anatabine was observed.

Taken together, these data suggest that NgADC1 and NgADC2 have a similar function regarding the production of alkaloids and indicate that their heterologous expression can be used to decrease the level of nicotine and nornicotine in *N. tabacum.*

Figure 4:
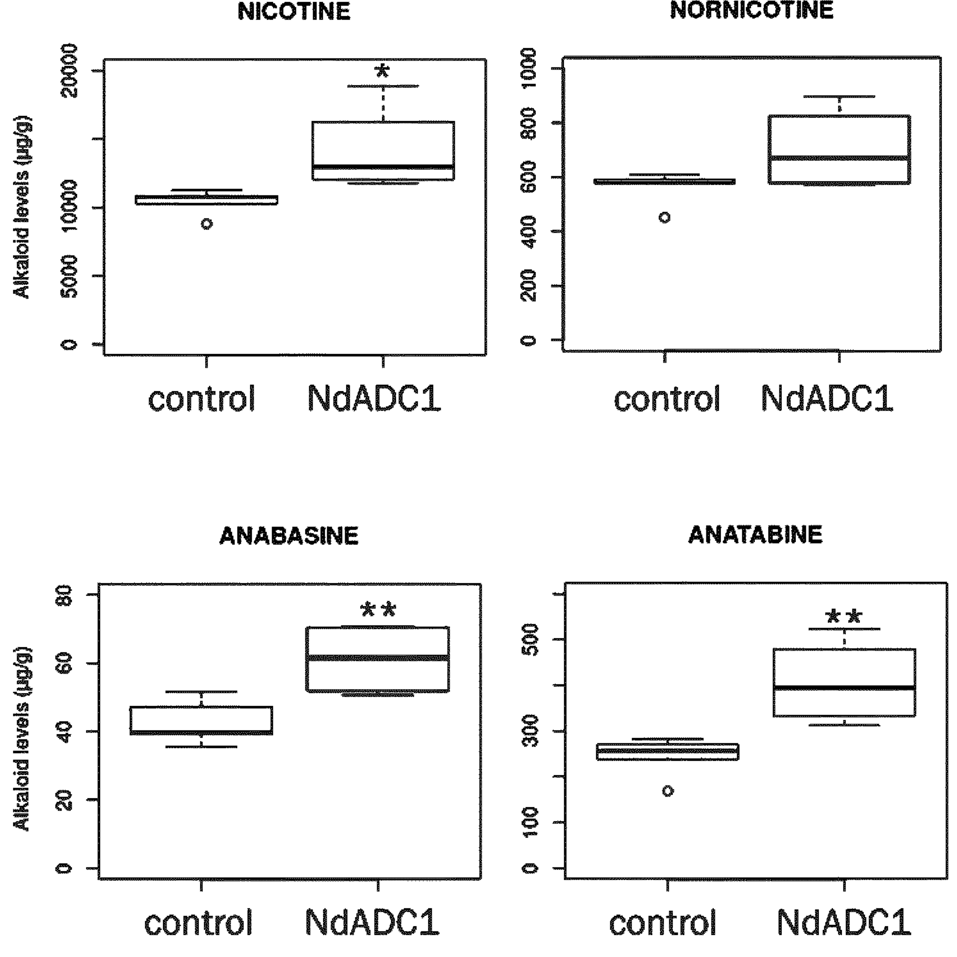
FIG. 4 is a series of graphs showing the overexpression of NdADC1 in TN90 (T0) plants. n=5 (control), n=4 (NdADC1), t-test, *p<0.05, **P<0.01. Significant increase of nicotine 1.3×. Significant increase of anabasine 1.6×. Significant increase of anatabine 1.4×.

As demonstrated in FIG. 4, overexpressing NdADC1 in *N. tabacum* resulted in a significant (P<0.01) increase of nicotine (1.3×, 136%), anabasine (1.4×, 143% and anatabine (1.6×, 167%) in the TO plants as compared to the controls. Nornicotine was also increased (125%). The impact on the alkaloids is the opposite to what was observed in *N. tabacum* overexpressing NgADC1 (see FIG. 2).

Example 4—Statistical Analysis

Statistical analysis of the results was performed using the software package Past3.20 (Øyvind Hammer, April 2018). All experimental results were expressed as mean±standard deviation (SD). Analysis of variance (ANOVA) and mean comparison were performed using Tukey's multiple-range test. A P value of <0.05 was considered to be statistically significant.

Any publication cited or described herein provides relevant information disclosed prior to the filing date of the present application. Statements herein are not to be construed as an admission that the inventors are not entitled to antedate such disclosures. All publications mentioned in the above specification are herein incorporated by reference. Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in cellular, molecular and plant biology or related fields are intended to be within the scope of the following claims.

TABLE 1

Table of amino acid substitutions

| | | |
|---|---|---|
| Aliphatic | Non-polar | Gly Ala Pro |
| | | Ile Leu Val |
| | Polar-uncharged | Cys Ser Thr Met |
| | | Asn Gly |
| | Polar-charged | Asp Glu |
| | | Lys Arg |
| Aromatic | | His Phe Trp Tyr |

TABLE 2

Levels of alkaloids in wild type *Nicotiana* species

| Species | Total alkaloids (mg/g) | Nicotine (%) | Nornicotine (%) | Anabasine (%) | Anatabine (%) |
|---|---|---|---|---|---|
| *N. tabacum* | 6.1 | 95.1 | 1.1 | 0.4 | 3.4 |
| *N. glauca* | 4.2 | 1.8 | 0.3 | 97.6 | 0.3 |
| *N. debneyi* | 5.6 | 40.8 | 5.2 | 48.6 | 5.4 |

Data from Sisson and Severson (1990) Supra

TABLE 3

Alkaloid measurements in Control, OE-NgADC1, OE-NgADC2 and OE-NADC1

| | | Average | SD |
|---|---|---|---|
| Control | NICOTINE | 10388.99 | 954.52 |
| | NORNICOTINE | 561.56 | 62.99 |
| | ANABASINE | 42.66 | 6.54 |
| | ANATABINE | 243.29 | 44.90 |
| OE-NgADC1 | NICOTINE | 8157.17 | 2286.28 |
| | NORNICOTINE | 433.20 | 92.84 |
| | ANABASINE | 61.76 | 26.33 |
| | ANATABINE | 316.98 | 111.46 |

TABLE 3-continued

| Alkaloid measurements in Control, OE-NgADC1, OE-NgADC2 and OE-NADC1 | | | |
|---|---|---|---|
| | | Average | SD |
| OE-NgADC2 | NICOTINE | 7759.15 | 2088.38 |
| | NORNICOTINE | 430.22 | 107.39 |
| | ANABASINE | 66.03 | 56.86 |
| | ANATABINE | 267.68 | 244.46 |
| OE-NdADC1 | NICOTINE | 14152.89 | 3248.47 |
| | NORNICOTINE | 702.13 | 153.70 |
| | ANABASINE | 61.18 | 10.75 |
| | ANATABINE | 406.21 | 93.48 |

Alkaloid measurements (average and SD in μg/g of leaf dry weight) in leaves of control plants TN90 (n=5), MMV::NgADC1 (n=5), MMV::NgADC2 (n=5) and MMV::NdADC1 (n=4). The control is wild-type *N. tabacum*.

TABLE 4

| Ratios of alkaloids in Control, OE-NgADC1, OE-NgADC2 and OE-NADC1 | | | | |
|---|---|---|---|---|
| | Control | OE-NgADC1 | OE-NgADC2 | OE-NdADC1 |
| Anabasine:anatabine | 0.18 | 0.19 | 0.25 | 0.15 |
| Anabasine:nornicotine | 0.08 | 0.14 | 0.15 | 0.09 |
| Anabasine:nicotine | 0.00 | 0.01 | 0.01 | 0.00 |
| Anatabine:nornicotine | 0.43 | 0.73 | 0.62 | 0.58 |
| Anatabine:nicotine | 0.02 | 0.04 | 0.03 | 0.03 |
| Nornicotine:nicotine | 0.05 | 0.05 | 0.06 | 0.05 |

Alkaloid measurements (average and SD in μg/g of leaf dry weight) were determined in leaves of control plants TN90 (n=5), MMV::NgADC1 (n=5), MMV::NgADC2 (n=5) and MMV::NdADC1 (n=4). The control is wild-type *N. tabacum*. All ratios described are calculated by dividing the amount for the first named alkaloid into the amount for the second named alkaloid, for example, to calculate the ratio of anabasine:anatabine the amount of anabasine is divided into the amount of anatabine.

SEQUENCES

```
SEQ ID NO: 1 NgADC1 (CDS)
atgcctgccttaggttgttgtgtagacgctgctgtttctcctcctcccggctattccttcctttgggatagttct
cttcccgcgccggggatttttccctccggcgtacctccgttgacaaacaccgccgctgctgccaccaccaccacc
cattggtctccggctcactcatccgctctttattgtattgacggatggggagctccgtatttcaccgttaattcc
tccggtgatatctccgttaagccacatggtacggaaactctgcctcaccaggaaatcgatctccttaaggtcgtg
aaaaaggcctccgacccgaaaaatttgggcggactcgggttgcagtttccgctcgttgttcggttccctgatatt
ctgaaaaaccggttggagtctcttcaatcggtttttgattatgctgttcagtcacaaggttatgaggctcactac
caaggtgtttatcctgttaaatgcaatcaggacaggttcgttgttgaagatattgtcaaatttgggtcgggtttc
cggttcggtctcgaagctgggtctaaacctgagcttctcctagctatgagctgtctctgcaagggcagtcgtgag
ggtcttcttgtatgcaacgggttcaaggatgctgagtacatttcgcttgctttggttgcaaggaagctaatgttg
aatacagtaattgtgcttgaacaagaagaggagcttgatttggtgattgacatcagcaagaaaatggcggtccgg
cctgtgatagggcttcgggctaagctcaggaccaagcattcgggccatttcggatccacttctggagagaaaggt
aaatttgggcttacaacaacacagatcgttcgtgtggtgaagaagctagaagaatctgaaatgttggattgtctt
cagttgctgcattttcatattggatctcagatcccttcgacagctttgcttgctgatggcgttggtgaggctgcc
cagatttactgtgaattagtccgcctcggagctggcatgaaatacatcgattgtggtggtggccttggaattgac
tatgatggatcaaaatcgtgtgattcagattgttctgttggatatggccttcaggagtatgcatctacggttgtt
caagctgttcgatttgtttgtgatcggaagaatgtgaaacatccggtgatctgtagcgagagtgggagagcaatt
gtatctcatcactctgttctgatatttgaggctgtgtcttcaactagtacacgctcacaagagttgtcttccttt
tatctccagtcatttgtggagaagcttagtgatgatgctcgtgctgattatcggaatttatctgctgctgctatt
cgtggagagtacgatacatgtgtactttatgccgatcagttgaagcagagatgtgtggagcagttcaaagatggt
gatttggacattgaacaacttgctgccgtggacggcatttgtgacttcgtgtcgaaggctattggggcttctgat
cctgtccgcacataccatgtgaatctttcgatcttcacttcaattcctgatttttgggcaattgaccaactattc
ccaattgttcccatccataagctagatgaaaggcctggagtcagaggaattttatcggacttgacctgtgatagt
gatgggaagattgataagttcataggaggagagtcaagcttgccgctccatgaattaggaagtaatggtggtggt
agtggtgatggtgggaaatactatctaggaatgtttttgggtggggcttatgaggaggcgctcgggggactccat
aacctatttggcggacctagcgttttgcgtgtgtcgcagagtgatagcccacacagcttcgctgtgacatgcgct
gttcctggtccatcttgtgctgacgttctccgggcgatgcagcacgagcctgaactcatgttcgagatgctcaag
caccgtgctgatgaattcatgcacaacgacgacgaacaagaagaggataaggggcttgcatttgcatctttggcg
agtagcttagctcagtcattcaacaatatgccttaccttgttactgattcatcttgctgcattactgctgccaat
aacggtggctattactattgcaatgatgagaacattgttggggttgtcgcagaatctgctgcagctgaagaagag
ctttggccttactgtgttgcttga

SEQ ID NO: 2 NgADC1 gene product
MPALGCCVDAAVSPPPGYSFLWDSSLPAPGIFPSGVPPLINTAAAATTTTHWSPAHSSALYCIDGWGAPYFTVNS
SGDISVKPHGTETLPHQEIDLLKVVKKASDPKNLGGLGLQFPLVVRFPDILKNRLESLQSVFDYAVQSQGYEAHY
QGVYPVKCNQDRFVVEDIVKFGSGFRFGLEAGSKPELLLAMSCLCKGSREGLLVCNGFKDAEYISLALVARKLML
NTVIVLEQEEELDLVIDISKKMAVRPVIGLRAKLRTKHSGHFGSTSGEKGKFGLTTTQIVRVVKKLEESEMLDCL
QLLHFHIGSQIPSTALLADGVGEAAQIYCELVRLGAGMKYIDCGGGLGIDYDGSKSCDSDCSVGYGLQEYASTVV
QAVRFVCDRKNVKHPVICSESGRAIVSHHSVLIFEAVSSTSTRSQELSSFYLQSFVEKLSDDARADYRNLSAAAI
RGEYDTCVLYADQLKQRCVEQFKDGDLDIEQLAAVDGICDFVSKAIGASDPVRTYHVNLSIFTSIPDFWAIDQLF
PIVPIHKLDERPGVRGILSDLTCDSDGKIDKFIGGESSLPLHELGSNGGGSGDGGKYYLGMFLGGAYEEALGGLH
NLFGGPSVLRVSQSDSPHSFAVTCAVPGPSCADVLRAMQHEPELMFEMLKHRADEFMHNDDEQEEDKGLAFASLA
SSLAQSFNNMPYLVTDSSCCITAANNGGYYYCNDENIVGVVAESAAAEEELWPYCVA

SEQ ID NO: 3 NgADC2 (CDS):
atgccggccctaggttgttgtgtagacgctgctgctgtttctcctcctcttggctatgccttctctcgggatagc
tctcttcccgcgccggagttctttacctccggcatacctccgacaaattccgccgccgcttcccattggtctccg
gatttgtcctctgctttgtacggggtcgatgggtgggggctccttatttctctgttaactctaacggagatatc
tccgtccgaccacatggtatggacactctccctcaccaggaaattgaccttctcaaggtcgtgaaaaaggcctcc
gacccgaaaaattcaggtgggcttggtcttcagctacctcttgttgttcgcttccctgatgtgctaaaaaaccgg
ttggaatctctgcagtcggcttttgatctcgcggttcattcccagggctatggggcccacttccaaggtgtttat
```

-continued

SEQUENCES cccgtgaaatgcaatcaagaccggttcgtggtggaagatattgtcaaattcgggtcgtcattccggttcgggttg
gaagccgggtctaaacccgagctcctgttagccatgagctgtctctgcaagggtagtgctgagggccttctcgtt
tgcaatggtttcaaggacgctgagtacatttcgcttgctttggttgcaagaaagctcatgttgaacactgtaatt
gtgcttgaacaagaggaggagcttgaccttgtgattgatataagccgtaagatggctgttcggcctgtaattgga
cttcgggctaagctcaggaccaagcattcaggccattttggatccacttctggagaaaaaggtaagtttgggctt
acaactacccaaattgttcgtgtagtgaagaagctggaagaatcaggaatgctggattgccttcagttgctgcat
tttcacattggatctcaaatcccttcaacagcggtgcttgctgacggtgttggtgaggctgctcagatttattgt
gaattagtccgtcttggtgcgggtatgaagttcattgatactggaggtgggcttggaattgattatgatggtact
aaatcatgcgattctgacgtctctgttggctatggcattcaagaatatgcctccacagttgtccaggaggttcaa
tatgtatgcgaccgtaagggcgtgaagcacccagtgatttgcagcgaaagtggcagggcaattgtttctcatcac
tcaattctgattttcgaagccgtgtcttcttctagtactcatgtttcttcttcacatctgtcttctggtgtcctc
caatccatggcggagacgctcaatgaagatgcccttgccgattaccgcaatttatctgctgctgcagttcgtgga
gagtacgagacatgtgtactttactctgatcagttgaaacagagatgtgtggatcagtttaaagaagggtccttg
ggtattgaacatcttgctgctgttgatagcatctgtgactttgtatcaaaggctatgggggctgctgatcctgtc
cgcacttaccatgtgaatctgtcaattttcacttcaattcctgattttgggcctttggtcaattgtttcctgtt
gttccaatacaccgtttagatgaaaagcctgcagtaaggggaatattatcggacttgacttgtgacagtgatggg
aaggttgataagttcattggtggcgaatcaagcttgccgctacatgaattgggaagtaacggcgatggtggtggg
tactatctggggatgtttttgggcggggcttatgaggaggcgctcggaggactccacaacttgtttggtggacca
agtgtcgtgcgcgtggtgcagagcgatagcgctcacagcttcgccatgactcgctccgtccctggcccgtcctgt
gcagacgtgctccgagcgatgcagcacgagcccgagctcatgttcgagacactcaagcaccgtgcagaggaattc
ttggaacaggaagatgacaaagggctggccgttgcatctttggccagcagcttagctcagtccttccataacatg
ccttaccttgtggcgcctgcatcttgctgcttcactgcagcggctgctaacaatggtggctataattactattac
agtgatgagaatgcagcagattctgctacaggggaggatgagatttggtcctattgcactgcttga SEQ ID NO: 4 NgADC2 gene product
MPALGCCVDAAAVSPPLGYAFSRDSSLPAPEFFTSGIPPTNSAAASHWSPDLSSALYGVDGWGAPYFSVNSNGDI
SVRPHGMDTLPHQEIDLLKVVKKASDPKNSGGLGLQLPLVVRFPDVLKNRLESLQSAFDLAVHSQGYGAHFQGVY
PVKCNQDRFVVEDIVKFGSSFRFGLEAGSKPELLLAMSCLCKGSAEGLLVCNGFKDAEYISLALVARKLMLNTVI
VLEQEEELDLVIDISRKMAVRPVIGLRAKLRTKHSGHFGSTSGEKGKFGLTTTQIVRVVKKLEESGMLDCLQLLH
FHIGSQIPSTAVLADGVGEAAQIYCELVRLGAGMKFIDTGGGLGIDYDGTKSCDSDVSVGYGIQEYASTVVQEVQ
YVCDRKGVKHPVICSESGRAIVSHHSILIFEAVSSSSTHVSSSHLSSGVLQSMAETLNEDALADYRNLSAAAVRG
EYETCVLYSDQLKQRCVDQFKEGSLGIEHLAAVDSICDFVSKAMGAADPVRTYHVNLSIFTSIPDFWAFGQLFPV
VPIHRLDEKPAVRGILSDLTCDSDGKVDKFIGGESSLPLHELGSNGDGGGYYLGMFLGGAYEEALGGLHNLFGGP
SVVRVVQSDSAHSFAMTRSVPGPSCADVLRAMQHEPELMFETLKHRAEEFLEQEDDKGLAVASLASSLAQSFHNM
PYLVAPASCCFTAAAANNGGYNYYYSDENAADSATGEDEIWSYCTA SEQ ID NO: 5 NdADC1 (CDS)
atgcctgccttaggttgttgtgtagacgctgctgtttctcctcctcccggctattccttcctttgggatagctct
cttcctgcgccggagattttccctccggcgtacctccgtcgacaaacaccgccgctgccaccaccaccaccacc
cactggtctccggcgcactcatccgctctttattctattgacggatggggtgctccgtatttcaccgttaattcc
tccggtgatatctccgttaagccacatggcacggaaactatgcctcaccaggaaatcgatctccttaaggtcgtg
aaaaaggcctccgatccgaaaaatttgggcggactcgggttgcagtttccgctcgttgttcggttccctgatatt
ctgaaaaatcggttggagtctcttcaatcagtttttgattatgcggttcagtcacaaggttatgaagctcactac
caaggtgtttatcctgtgaaatgcaatcaggacaggttcgttgtagaagatattgtcaaattcgggtcgggtttc
cgcttcggtcttgaagccgggtctaaacctgagctcctcctagctatgagctgtctctgcaaaggcagccgtgag
ggttttcttgtatgcaacgggttcaaggatgcggagtacatttcgcttgctttggttgcaaggaagctcatgttg
aatacagtaattgtgcttgaacaagaggaggagcttgatttggtgattgacatcagcagaaaaatggcggtccga
cctgtgatcgggcttcgggctaagctcaggaccaaacattcaggacatttcggatccacttcgggagagaaaggt
aagtttggacttacgactacacagatagttcgtgtggtgaagaagctagaagaatccgaaatgctggattgtctt
cagttgctgcattttcatattggatctcagataccttcgaccgctttgcttgctgatggcgttggtgaggctgcc
cagatttactgtgaattagtccgcctcggtgctggcatgaaatacgtcgattgtggtggtggccttggaattgac
tatgatggtacaaaatcttgtgattccgattgttctgttggatatggccttcaggagtatgcatctacggttgtt
caagctgttcaatttgtttgtgaccggaagaatgtgaaacatccggtgatctgtagcgagagtggtagagcaatt
gtatctcatcactctgttctaatatttgaggctgtttcttcaactacaacacgctcacaagagttatcttctgtt
gatctccagtcatttgtggagaagcttaatgatgatggtcgtgctgattatcggaatttatctgctgctgctatt
cgtggagagtacgatacatgtgtactttatgccgatcagttgaaacagagatgtgtggagcagttcaaagatggt
gatttggacattgaacaacttgctgccgtggatggcatttgtgacttcgtgtcgaaggctattggggcttctgat
cctgtccgcacataccatgttaatctttcgatcttcacttcaattcctgatttttgggcaattgaccaactattc
ccaattgttcccatccataagctagatgaacggcctggtgtccgaggaattttatcggacttgacctgtgatagt
gatgggaagattgataagttcattggagggggagtcaagtttgccgctccatgaattaggaagcaatggtggtggt
agtggtgatggtgggaaatactatctgggaatgtttttgggtggggcttatgaggaggcgctcggggggactccat
aacctatttggcggacccagcgttttgcgtgtgtcacagagcaatagcccgcacagcttcgctgtgacatccgct
gttcctggtccgtcttgtgctgatgttctccgggcgatgcagcacgagcctgaactcatgttcgagacactcaag
caccgcgctgaagaattcgtgcacgaccacgacgaacaagaagaagataaggggcttgcacttgcctctttggcc
agcagcttagctcagtcattcaacaatatgccttacctttctactaattcatcttgctgccttactgctgccaat
aacagtggctattactattgcaatgatgagaacattgttggagttggcgcagaatctgctgcagctgaagaagag
ctttggccttactgtgttgcttga SEQ ID NO: 6 NdADC1 gene product
MPALGCCVDAAVSPPPGYSFLWDSSLPAPEIFPSGVPPSTNTAAATTTTTHWSPAHSSALYSIDGWGAPYFTVNS
SGDISVKPHGTETMPHQEIDLLKVVKKASDPKNLGGLGLQFPLVVRFPDILKNRLESLQSVFDYAVQSQGYEAHY
QGVYPVKCNQDRFVVEDIVKFGSGFRFGLEAGSKPELLLAMSCLCKGSREGFLVCNGFKDAEYISLALVARKLML
NTVIVLEQEEELDLVIDISRKMAVRPVIGLRAKLRTKHSGHFGSTSGEKGKFGLTTTQIVRVVKKLEESEMLDCL
QLLHFHIGSQIPSTALLADGVGEAAQIYCELVRLGAGMKYVDCGGGLGIDYDGTKSCDSDCSVGYGLQEYASTVV
QAVQFVCDRKNVKHPVICSESGRAIVSHHSVLIFEAVSSTTTRSQELSSVDLQSFVEKLNDDGRADYRNLSAAAI
RGEYDTCVLYADQLKQRCVEQFKDGDLDIEQLAAVDGICDFVSKAIGASDPVRTYHVNLSIFTSIPDFWAIDQLF
PIVPIHKLDERPGVRGILSDLTCDSDGKIDKFIGGESSLPLHELGSNGGGSGDGGKYYLGMFLGGAYEEALGGLH -continued

| SEQUENCES |
| --- |

NLFGGPSVLRVSQSNSPHSFAVTSAVPGPSCADVLRAMQHEPELMFETLKHRAEEFVHDHDEQEEDKGLALASLA
SSLAQSFNNMPYLSTNSSCCLTAANNSGYYYCNDENIVGVGAESAAAEEELWPYCVA

SEQ ID NO: 7 NgADC1 forward primer-OENgADC1-F
agaatctgaaatgttggattgtcttca

SEQ ID NO: 8 NgADC1 reverse primer-OENgADC1-R
tgaatcacacgattttgatccatcata

SEQ ID NO: 9 NgADC2 forward primer-OENgADC2-F
gggctccttatttctctgttaactct

SEQ ID NO: 10 NgADC2 reverse primer-OENgADC2-R
gatcaaaagccgactgcagagattc

SEQ ID NO: 11 NdADC1 forward primer-OENdADC1-F
tgtgtcacagagcaatagcccg

SEQ ID NO: 12 NdADC1 reverse primer-OENdADC1-R
gcaagtgcaagccccttatcttc

SEQ ID NO: 13 NADC1-S (CDS)
atgcctgccttaggttgttgtgtagacgctgctgtttctcctcctcccggctattccttcctttgggatagttct
cttcccgcgccggagattttccctccggcgtacctccgtcgacaaacaccgccgttgccaccaccaccaccacc
cattggtctccggcgcactcatccgctctttattctattgacggatggggcgctccgtatttcaccgttaattcc
tccggtgatatctccgttaagccacatggtacggatactctgcctcaccaggaaatcgatctccttaaggtcgtg
aaaaaggcctccgacccgaaaaatttgggcggactcgggttgcagtttccgctcgttgttcggttccctgatatt
ctgaaaaaccggttggagtctcttcaatccgtttttgattatgcggttcagtcacaaggttatgaagctcactac
caaggtgtttatcctgtgaaatgcaaccaggacaggttcgttgttgaagatattgtcaaattcggatcgggtttc
cggttcggtctcgaagctgggtctaaacctgagctcctcctagctatgagctgtctctgcaaaggcagtcatgag
ggtcttcttgtgtgcaacgggttcaaggatgctgagtacatttcgcttgctttggttgcaaggaagctcatgttg
aatacagtaattgtccttgaacaagaggaggagcttgatttggtgattgacatcagcaagaaaatggcggtccgg
cctgtgatcgggcttcgggctaagctcaggaccaaacattcgggtcatttcggatccacttctggagagaaaggt
aaatttgggctcacgacaacacagattgttcgtgtggtgaagaagctagaagaatccggaatgctggattgtctt
cagttgctgcattttcatatcggatctcaaatcccttcgacggctttgcttgctgatggcgttggtgaggctgcc
cagatttactgtgaattagtccgcctcggtgctggcatgaaatacattgattgtggtggtggccttggaattgac
tatgatggtacaaaatcatgtgattccgattgttctgttggatatggccttcaggaatatgcatctacggttgtt
caagctgttcgatttgtttgtgaccggaagaacgtgaaacatccggtgatctgtagcgagagtgggagagcaatt
gtatctcatcactctgttctgatatttgaggctgtgtcttcaactacaacacgctcacaagagttatcttctgtt
gatctccagtcatttgtggagaagctcaatgatgatgctcgtgctgattatcggaatttatctgctgctgctatt
cgtggagagtacgatacgtgtgtactttatgctgatcagttgaaacagagatgtgtggagcagttcaaagatggt
gatttggacattgaacaacttgctgcagtagatggcatttgtgatttcgtgtcgaaggctattggggcttctgat
cctgtccgcacataccatgtgaatctttcgatcttcacttcagttcctgattttgggcaattgaccaactattc
ccaattgttcccatccataagctagatgaacggcctgtagttcgaggaattttatcggacttgacctgtgatagt
gatgggaagattgataagttcattggaggagagtcaagcttgccgctccatgaattaggaagtaatggtggtggt
ggtggtgatggtggaaaatattatctaggaatgtttttgggtggggcttatgaggaggcgcttggggggactccat
aacctatttggcggacccagcgttttgcgtgtgtcacagagcgatagcccacacagcttcgccgtgacatgtgct
gttcctggtccgtcctgtgctgacgttctccgggcgatgcagcacgagcctgaactcatgttcgagacgctcaag
caccgcgctgaagaattcgtgcacaatgacgacgaacaagaagaagataaagggcttgcatttgcatctttggcc
agcagcttagctcagtcattcaacaatatgccttaccttgttactaattcatcttgctgccttactgctgctgcc
aataacggtggctattactattgcaatgatgagaacattgttggagttggcgcagaatctgctgcagctgaagaa
gagctttggccttactgtgttgcttga SEQ ID NO: 14 NtADC1-S gene product
MPALGCCVDAAVSPPPGYSFLWDSSLPAPEIFPSGVPPSTNTAVATTTTTHWSPAHSSALYSIDGWGAPYFTVNS
SGDISVKPHGTDTLPHQEIDLLKVVKKASDPKNLGGLGLQFPLVVRFPDILKNRLESLQSVFDYAVQSQGYEAHY
QGVYPVKCNQDRFVVEDIVKFGSGFRFGLEAGSKPELLLAMSCLCKGSHEGLLVCNGFKDAEYISLALVARKLML
NTVIVLEQEEELDLVIDISKKMAVRPVIGLRAKLRTKHSGHFGSTSGEKGKFGLTTTQIVRVVKKLEESGMLDCL
QLLHFHIGSQIPSTALLADGVGEAAQIYCELVRLGAGMKYIDCGGGLGIDYDGTKSCDSDCSVGYGLQEYASTVV
QAVRFVCDRKNVKHPVICSESGRAIVSHHSVLIFEAVSSTTTRSQELSSVDLQSFVEKLNDDARADYRNLSAAAI
RGEYDTCVLYADQLKQRCVEQFKDGDLDIEQLAAVDGICDFVSKAIGASDPVRTYHVNLSIFTSVPDFWAIDQLF
PIVPIHKLDERPVVRGILSDLTCDSDGKIDKFIGGESSLPLHELGSNGGGGGDGGKYYLGMFLGGAYEEALGGLH
NLFGGPSVLRVSQSDSPHSFAVTCAVPGPSCADVLRAMQHEPELMFETLKHRAEEFVHNDDEQEEDKGLAFASLA
SSLAQSFNNMPYLVINSSCCLTAAANNGGYYYCNDENIVGVGAESAAAEEELWPYCVA SEQ ID NO: 15 NtADC1-T (CDS)
atgcctgccttaggttgttgtgtagacgctgctgtttctcctcctcccggctattccttcctttgggatagctct
cttcccgcgccggagatttttccctccggcgtacctctgtcgacaaacaccgccgccactaccacgaccaccacc
cattggtctccggcgcactcatccgctctttattctattgacggatggggtgctccgtatttcaccgttaattcc
tccggtgatatctccgttaagccacatggtacggaaactctgcctcaccaggaaattgatctccttaaggtcgtg
aaaaaagcatccgacccgaaaaattcgggtggactcgggttgcagtttccgctcgttgttcggttccctgatatt
ctgaaaaaccggttggagtctctacaatcggcttttgattatgcggttcagtcacaaggttatgaggctcactac
caaggtgtttatcctgttaaatgcaatcaggacaggttcgttgttgaagatattgtcaaattcgggtcgggtttc
cgattcggtctcgaagccggctcgaaacccgagctcctcctagctatgagctgtctctgcaagggcagtcgcgag
ggtcttcttgtatgcaacgggttcaaagatgctgactacatttcgcttgctttggttgcaaggaagctcatgttg
aatacagtaattgtgcttgaacaagaggaggagcttgatttggtgattgacatcagcagaaaaatggctgtccgg
cctttgatcgggcttcgggctaagctcaggaccaaacattccggccatttcggatccacttcaggagagaaaggt -continued

| SEQUENCES |
| --- |

aagtttgggcttacgacaacacagatcgttcgtgtggtgaagaagctagaagaatccggaatgttggattgtctt
cagctgctgcattttcatattggatctcagatcccttcgacggctttgcttgctgatggcgtgggtgaggccgct
cagatttactgtgaattagtccgccttggtgctggcatgaaatacattgattgtggtggtggccttggaattgac
tatgatggtacaaaatcgtgtgattccgattgttcagttggatatggccttcaggagtatgcatctacagttgtt
caagctgttcgatttgtttgtgatcggaagaatgtgaaacatccggtgatttgtagcgagagtgggagagcaatt
gtatctcatcactctgttttgatatttgaggctgtttcttcaactacaacacgctcacaagagttatcttctgtt
gatctccagtcatttgtggagaagcttaatgatgatgctcgtgctgattatcggaatttatctgctgctgctatt
cgtggagagtacgatacgtgtgtactttatgccgatcagttgaaacagagatgtgtggagcagttcaaagatggt
aatttggacattgaacagcttgctgccgtagatggtatttgtgacttcgtgtcgaaggctattggggcttctgat
cctgtccgcacatatcatgtgaatctttcgatcttcacttcaattcccgattttgggcaattgaccaactattc
ccaattgttcccatccataagctagatgaacggcctggagtccgaggaatattatcggacttgacctgtgatagt
gatgggaagattgataagttcattggaggagagtcaagcttgccgctccatgaattaggaagtaatggtggtggt
gatggtgggaaatattatctgggaatgtttttgggtggggcttatgaggaggcgctcgggggcctccataaccta
tttggcggacccagtgttttgcgcgtgtcacagagcgatagcccacacagcttcgctgtgacatgcgctgttcct
ggtccgtcttgtgctgacgttctccgggcgatgcagcacgagcctgaactcatgttcgagacgctcaagcaccgt
gctgaagaattcgtgcataatgacgacgaacaagaagaagataaagggcttgcatttgcatctttagccagcagc
ttagctcagtcattcaacaatatgccttaccttgttaccaattcatcttgctgccttactgctaccaataacggt
ggctattactattgcaatgatgagaacattgttggggttggcgcagaatctgctgcagctgaggaagagctttgg
ccttactgtgttgcttga SEQ ID NO: 16 NtADC1-T gene product
MPALGCCVDAAVSPPPGYSFLWDSSLPAPEIFPSGVPLSTNTAATTTTTTHWSPAHSSALYSIDGWGAPYFTVNS
SGDISVKPHGTETLPHQEIDLLKVVKKASDPKNSGGLGLQFPLVVRFPDILKNRLESLQSAFDYAVQSQGYEAHY
QGVYPVKCNQDRFVVEDIVKFGSGFRFGLEAGSKPELLLAMSCLCKGSREGLLVCNGFKDADYISLALVARKLML
NTVIVLEQEEELDLVIDISRKMAVRPLIGLRAKLRTKHSGHFGSTSGEKGKFGLTTTQIVRVVKKLEESGMLDCL
QLLHFHIGSQIPSTALLADGVGEAAQIYCELVRLGAGMKYIDCGGGLGIDYDGTKSCDSDCSVGYGLQEYASTVV
QAVRFVCDRKNVKHPVICSESGRAIVSHHSVLIFEAVSSTTTRSQELSSVDLQSFVEKLNDDARADYRNLSAAAI
RGEYDTCVLYADQLKQRCVEQFKDGNLDIEQLAAVDGICDFVSKAIGASDPVRTYHVNLSIFTSIPDFWAIDQLF
PIVPIHKLDERPGVRGILSDLTCDSDGKIDKFIGGESSLPLHELGSNGGGDGGKYYLGMFLGGAYEEALGGLHNL
FGGPSVLRVSQSDSPHSFAVTCAVPGPSCADVLRAMQHEPELMFETLKHRAEEFVHNDDEQEEDKGLAFASLASS
LAQSFNNMPYLVINSSCCLTATNNGGYYYCNDENIVGVGAESAAAEEELWPYCVA SEQ ID NO: 17 NtADC2-S (CDS)
atgccggccctaggttgttgtgtagatgctgctgttgtttcccctcctctcagctatgccttctctcgggatagc
tctcttcccgcgccggagttctttgcctccggcgtacctccgacaaattctgccgctgcttcccattggtctccg
gatttgtcgtctgctttatacggggtcgatgggtggggagctccttatttctctgttaactctaatggagatatc
tccgtccgaccacacggtacggacactctccctcaccaggaaattgaccttctcaaggtcgtgaaaaaggcctcc
gacccgaaaaattcaggtgggcttgggcttcagctgcctcttgttgttcgcttccctgatgtgttgaaaaaccgg
ttggaatctctgcaatcggcttttgatctcgcggttcattcccagggctatggggcccactaccaaggtgtttat
cccgtgaaatgcaatcaagacaggttcgtggtggaagatatcgtgaaattcgggtcgccattccggttcgggttg
gaagccgggtctaaacccgagctcctgttagccatgagctgtctctgcaagggcagtgctgagggccttctcgtt
tgcaatggtttcaaggacgctgagtacatttcgcttgctttggttgcaagaaagctcatgttaaacactgtaatt
gtgcttgaacaagaggaggagcttgaccttgtgattgatataagccataagatggctgttcggcctgtaattgga
cttcgggctaagctcaggaccaagcattcaggccattttggatccacttctggagaaaaaggtaagtttgggctt
acaacgacccaaattgttcgtgtggtgaagaagctagaagaatccggaatgctggattgccttcagttgctgcat
tttcacattggatctcagatcccttctacggggttgctagctgatggagttggtgaggccgctcagatttattgt
gaattagtccgtcttggagcgggtatgaagttcattgatattggaggtgggcttggaattgattatgatggtact
aaatcatgcgattctgatgtctctgttggctatggcattcaagaatatgcctccgcagttgttcaggcggttcaa
tatgtatgcgaccgtaagggtgtgaaacacccagtgatctgcagcgaaagtggcagggcaattgtttctcatcac
tcaattctgattttcgaagccgtgtctgcttctagtactcatgtttcttcttcacatctgtcttctggtggcctc
caatccatggcggagacgctcaacgaagatgcccttgctgattaccgcaatttatctgctgctgcagttcgtgga
gagtatgagacatgtgtactttactctgatcagttgaaacagagatgtgtggagcagtttaaagaagggtccttg
ggtattgaacatcttgctgctgttgatagcatctgtgactttgtatcaaaggctatgggggctgctgatcctgtc
cgcacttaccatgtgaatctgtcaattttcacttcaattcctgattttgggcctttggtcaattgtttccgatt
gttccaattcaccgcttagatgaaaagcctgcagtgaggggaatattatcggacttaacttgtgacagtgatggg
aaggttgataagttcattggtggcgaatcaagcttgccgctacatgaattgggaagtaatggcgatggtggtggt
tattatctggggatgtttttgggtggggcttatgaggaggcgctcggaggactccacaacctgtttggtggacca
agtgtcgtgcgcgtggtgcagagcgatagcgctcacagctttgccatgactcgctccgtccctggcccgtcttgc
gctgatgtgctccgagcgatgcagcacgagcccgagctcatgttcgagactctcaagcaccgtgcggaggaattc
ttggaacaagaagatgacaaagggctggctgttgaatctttggccagcagcgtagctcagtccttccataacatg
ccttaccttgtggcgccttcatcttgccgcttcactgctgctactgataacaatggtggctataattactattac
agtgatgagaatgcagcagattctgctacaggggaggatgagatttggtcctattgcactgcttga SEQ ID NO: 18 NtADC2-S gene product
MPALGCCVDAAVVSPPLSYAFSRDSSLPAPEFFASGVPPTNSAAASHWSPDLSSALYGVDGWGAPYFSVNSNGDI
SVRPHGTDTLPHQEIDLLKVVKKASDPKNSGGLGLQLPLVVRFPDVLKNRLESLQSAFDLAVHSQGYGAHYQGVY
PVKCNQDRFVVEDIVKFGSPFRFGLEAGSKPELLLAMSCLCKGSAEGLLVCNGFKDAEYISLALVARKLMLNTVI
VLEQEEELDLVIDISHKMAVRPVIGLRAKLRTKHSGHFGSTSGEKGKFGLTTTQIVRVVKKLEESGMLDCLQLLH
FHIGSQIPSTGLLADGVGEAAQIYCELVRLGAGMKFIDIGGGLGIDYDGTKSCDSDVSVGYGIQEYASAVVQAVQ
YVCDRKGVKHPVICSESGRAIVSHHSILIFEAVSASSTHVSSSHLSSGGLQSMAETLNEDALADYRNLSAAAVRG
EYETCVLYSDQLKQRCVEQFKEGSLGIEHLAAVDSICDFVSKAMGAADPVRTYHVNLSIFTSIPDFWAFGQLFPI
VPIHRLDEKPAVRGILSDLTCDSDGKVDKFIGGESSLPLHELGSNGDGGGYYLGMFLGGAYEEALGGLHNLFGGP
SVVRVVQSDSAHSFAMTRSVPGPSCADVLRAMQHEPELMFETLKHRAEEFLEQEDDKGLAVESLASSVAQSFHNM
PYLVAPSSCRFTAATDNNGGYNYYYSDENAADSATGEDEIWSYCTA -continued

SEQUENCES

SEQ ID NO: 19 NtADC2-T (CDS)

```
atgccggccctaggttgttgcgtagacgctactgtttcccctcctctcggctatgccttctctcgggatagctct
cttcccgcgccggagttctttacctccggcgtacctcctacaaactccgccgccggttcccattggtctccggat
ctgtcctctgctttgtacggggtcgatgggtggggagctccttatttctccgttaactctaacggagatatctcc
gtccgaccacatggtacggacacactcccccaccaggaaattgaccttctcaaggtcgtgaaaaaggcctccgac
ccgaaaaattcagggggggctcgggcttcagctgcctcttgttgttcgcttccctgatgtgctaaaaaaccggttg
gaatctctgcaatcggcttttgatctcgctgttcattcccagggctatggggcccactaccaaggtgtttatccc
gtgaaatgcaatcaagacaggttcgtggtggaagatattgtcaaattcgggtcgtcattccggttcgggttggaa
gctgggtctaaacccgagctcctgttagccatgagctgtctctgcaggggcagtgctgagggccttctcgtttgc
aatggtttcaaggacgctgagtacatttcgcttgctttggttgcaagaaagctcatgttaaacactgtaattgtt
cttgaacaagaggaggagcttgaccttgtgattgatataagccgtaagatggctgttcggcccgtaattggactt
cgggctaagctcaggaccaagcattcaggccattttggatccacttctggagaaaaaggtaagtttgggcttaca
acgacccaaattgttcgtgtagtgaagaagctggaagaatccggaatgctggattgccttcagttgctgcatttt
cacattggatctcagatcccttcaacggcgttgcttgctgatggtgttggtgaggctgctcagatttattgtgaa
ttaatccgtcttggtgcgggtatgaagttcattgatactggaggtgggctcggaattgattatgatggtactaaa
tcatgtgattcagatgtctctgttggctatggcattcaagaatacgcctccacagttgtccaggcggttcaatat
gtttgcgaccgtaagggcgtgaagcacccagtgatttgcagcgaaagtggcagggcaattgtttctcatcactca
attctgattttcgaagccgtgtctgcttctagcactcatgtttcttcttcacatctgtcttctggtggcctccaa
tccatggcggagacgctcaatgaagatgcccttgctgattaccgcaatttatctgctgctgcagttcgtggagag
tacgagacgtgtgtactttactctgatcagttgaaacagagatgtgtggatcagtttaaagaagggtccttgggt
attgaacatcttgctgctgttgatagcatctgtgactttgtatcaaaggctatgggggctgctgatcctatccgc
acttaccatgtgaatctgtcaattttcacttcaattcctgatttttgggcctttggtcaattgtttccgattgtt
ccaatacaccgtttagatgaaaagcctgcagtaaggggaatattatcggacttgacttgtgacagtgatgggaag
gttgataagttcattggtggcgaatcaagcttgcagctgcatgaattgggaagtaatggcgatggtggtgggtat
tatctggggatgtttttgggtggggcttatgaggaggcgctcggaggactccacaacctgtttggtggaccaagc
gtggtgcgcgtggtgcagagcgatagcgctcacagcttcgccatgtctcgctccgtccctggcccgtcctgcgcg
gacgtgctccgagcgatgcagcacgagcccgagctcatgttcgagactctcaagcaccgtgcggaggaattcttg
gaacaagaagaagacaaagggctggccattgcatctttggccagcagcttagctcagtccttccataacatgcct
taccttgtggcgcctgcatcttgctgcttcactgcagttactgctaacaacggtggctataactactattacagt
gatgagaatgcagcagattctgctacaggggaggatgagatttggtcctattgcactgcttga
```

SEQ ID NO: 20 NtADC2-T gene product

```
MPALGCCVDATVSPPLGYAFSRDSSLPAPEFFTSGVPPINSAAGSHWSPDLSSALYGVDGWGAPYFSVNSNGDIS
VRPHGTDTLPHQEIDLLKVVKKASDPKNSGGLGLQLPLVVRFPDVLKNRLESLQSAFDLAVHSQGYGAHYQGVYP
VKCNQDRFVVEDIVKFGSSFRFGLEAGSKPELLLAMSCLCRGSAEGLLVCNGFKDAEYISLALVARKLMLNTVIV
LEQEEELDLVIDISRKMAVRPVIGLRAKLRTKHSGHFGSTSGEKGKFGLTTTQIVRVVKKLEESGMLDCLQLLHF
HIGSQIPSTALLADGVGEAAQIYCELIRLGAGMKFIDTGGGLGIDYDGTKSCDSDVSVGYGIQEYASTVVQAVQY
VCDRKGVKHPVICSESGRAIVSHHSILIFEAVSASSTHVSSSHLSSGGLQSMAETLNEDALADYRNLSAAAVRGE
YETCVLYSDQLKQRCVDQFKEGSLGIEHLAAVDSICDFVSKAMGAADPIRTYHVNLSIFTSIPDFWAFGQLFPIV
PIHRLDEKPAVRGILSDLTCDSDGKVDKFIGGESSLQLHELGSNGDGGGYYLGMFLGGAYEEALGGLHNLFGGPS
VVRVVQSDSAHSFAMSRSVPGPSCADVLRAMQHEPELMFETLKHRAEEFLEQEEDKGLAIASLASSLAQSFHNMP
YLVAPASCCFTAVTANNGGYNYYYSDENAADSATGEDEIWSYCTA
```

The invention claimed is:

1. A transgenic *Nicotiana tabacum* plant cell comprising a heterologous polynucleotide sequence that encodes a heterologous polypeptide sequence selected from:

a) a polypeptide sequence having at least 97% sequence identity to SEQ ID NO: 2, wherein the amino acid at position 31 is G, 40 is L, 63 is C, 296 is E, 355 is S, 417 is S, 429 is Y, 438 is S, 652 is M, 658 is D, 661 is M, 700 is D, 707 is I, and 730 is V; and b) a polypeptide sequence having at least 97.5% sequence identity to SEQ ID NO: 4, wherein the amino acid at position 12 is A, 37 is I, 87 is M, 151 is F, 317 is V, 378 is E, 429 is V, 530 is V, and 680 is V;

wherein the heterologous polynucleotide sequence is operably linked to a promotor directing expression of the heterologous polypeptide sequence.

2. The transgenic *Nicotiana tabacum* plant cell according to claim 1, wherein the heterologous polypeptide sequence is a polypeptide sequence having at least 97% sequence identity to SEQ ID NO: 2, wherein the amino acid at position 31 is G, 40 is L, 63 is C, 296 is E, 355 is S, 417 is S, 429 is Y, 438 is S, 652 is M, 658 is D, 661 is M, 700 is D, 707 is I, and 730 is V.

3. The transgenic *Nicotiana tabacum* plant cell according to claim 1, wherein the heterologous polypeptide sequence is a polypeptide sequence having at least 97.5% sequence identity to SEQ ID NO: 4, wherein the amino acid at position 12 is A, 37 is I, 87 is M, 151 is F, 317 is V, 378 is E, 429 is V, 530 is V, and 680 is V.

4. A transgenic *Nicotiana tabacum* plant comprising a plurality of plant cells according to claim 1.

5. The transgenic *Nicotiana tabacum* plant according to claim 4, wherein levels of nicotine and nornicotine are decreased in the plant compared to an otherwise identical control *Nicotiana tabacum* plant not comprising cells comprising the heterologous polynucleotide.

6. The transgenic *Nicotiana tabacum* plant according to claim 5, wherein levels of nicotine and nornicotine are decreased in the plant by at least 20% compared to an otherwise identical control *Nicotiana tabacum* plant not comprising cells comprising the heterologous polynucleotide.

7. The transgenic *Nicotiana tabacum* plant according to claim 6, wherein levels of anabasine and anatabine are from 90% to 110% the levels of anabasine and anatabine in an otherwise identical control *Nicotiana tabacum* plant not comprising cells comprising the heterologous polynucleotide.

8. The transgenic *Nicotiana tabacum* plant cell according to claim 1, wherein the heterologous polypeptide sequence comprises SEQ ID NO: 2 or SEQ ID NO: 4.

9. A plant material comprising a transgenic *Nicotiana tabacum* plant that comprises the plant cell according to claim 1, wherein the plant material is a cured or dried plant material, and wherein the cured or dried plant material is flue-cured, fire-cured, smoke-cured, sun-cured, or air-cured.

10. A tobacco product or smoking article comprising the transgenic *Nicotiana tabacum* plant material according to claim 9.

11. A transgenic *Nicotiana tabacum* plant cell comprising a heterologous polynucleotide sequence that encodes a heterologous polypeptide sequence having at least at least 97.5% sequence identity to SEQ ID NO: 6, wherein the amino acid at position 90 is M, 203 is F, 296 is E, 342 is V, 380 is Q, 441 is G, 619 is N, 628 is S, 663 is D, 664 is H, 680 is L, 698 is S, and 715 is S;

wherein the heterologous polynucleotide sequence is operably linked to a promotor directing expression of the heterologous polypeptide sequence.

12. A transgenic *Nicotiana tabacum* plant comprising a plurality of plant cells according to claim 11.

13. The transgenic *Nicotiana tabacum* plant according to claim 12, wherein levels of nicotine and nornicotine are increased in the plant compared to an otherwise identical control *Nicotiana tabacum* plant not comprising cells comprising the heterologous polynucleotide.

14. The transgenic *Nicotiana tabacum* plant according to claim 13, wherein levels of nicotine and nornicotine are increased in the plant by at least 20% compared to an otherwise identical control *Nicotiana tabacum* plant not comprising cells comprising the heterologous polynucleotide.

15. The transgenic *Nicotiana tabacum* plant according to claim 14, wherein levels of anabasine and anatabine are increased by at least 25% relative to the levels of anabasine and anatabine in an otherwise identical control *Nicotiana tabacum* plant not comprising cells comprising the heterologous polynucleotide.

16. The transgenic *Nicotiana tabacum* plant cell according to claim 11, wherein the heterologous polypeptide sequence comprises SEQ ID NO: 6.

17. A plant material comprising a transgenic *Nicotiana tabacum* plant that comprises the plant cell according to claim 11, wherein the plant material is a cured or dried plant material, and wherein the cured or dried plant material is flue-cured, fire-cured, smoke-cured, sun-cured, or air-cured.

18. A tobacco product or smoking article comprising the transgenic *Nicotiana tabacum* plant material according to claim 17.

* * * * *

SEQUENCE LISTING

```
Sequence total quantity: 21
SEQ ID NO: 1           moltype = DNA  length = 2199
FEATURE                Location/Qualifiers
source                 1..2199
                       mol_type = genomic DNA
                       organism = Nicotiana glauca
SEQUENCE: 1
atgcctgcct taggttgttg tgtagacgct gctgtttctc ctcctcccgg ctattccttc  60
ctttgggata gttctcttcc cgcgccgggg atttttccct ccggcgtacc tccgttgaca  120
aacaccgccg ctgctgccac caccaccacc cattggtctc cggctcactc atccgctctt  180
tattgtattg acggatgggg agctccgtat ttcaccgtta attcctccgg tgatatctcc  240
gttaagccac atggtacgga aactctgcct caccaggaaa tcgatctcct taaggtcgtg  300
aaaaaggcct ccgacccgaa aaatttgggc ggactcgggt tgcagtttcc gctcgttgtt  360
cggttccctg atattctgaa aaaccggttg gagtctcttc aatcggtttt tgattatgct  420
gttcagtcac aaggttatga ggctcactac caaggtgttt atcctgttaa atgcaatcag  480
gacaggttcg ttgttgaaga tattgtcaaa tttgggtcgg gtttccggtt cggtctcgaa  540
gctgggtcta aacctgagct tctcctagct atgagctgtc tctgcaaggg cagtcgtgag  600
ggtcttcttg tatgcaacgg gttcaaggat gctgagtaca tttcgcttgc tttggttgca  660
aggaagctaa tgttgaatac agtaattgtg cttgaacaag aagaggagct tgatttggtg  720
attgacatca gcaagaaaat ggcggtccgg cctgtgatag ggcttcgggc taagctcagg  780
accaagcatt cgggccattt cggatccact tctggagaga aaggtaaatt tgggcttaca  840
acaacacaga tcgttcgtgt ggtgaagaag ctagaagaat ctgaaatgtt ggattgtctt  900
cagttgctgc attttcatat tggatctcag atcccttcga cagctttgct tgctgatggc  960
gttggtgagg ctgcccagat ttactgtgaa ttagtccgcc tcggagctgg catgaaatac  1020
atcgattgtg gtggtggcct tggaattgac tatgatggat caaaatcgtg tgattcagat  1080
tgttctgttg gatatggcct tcaggagtat gcatctacgg ttgttcaagc tgttcgattt  1140
gtttgtgatc ggaagaatgt gaaacatccg gtgatctgta gcgagagtgg gagagcaatt  1200
```

```
gtatctcatc actctgttct gatatttgag gctgtgtctt caactagtac acgctcacaa  1260
gagttgtctt ccttttatct ccagtcattt gtggagaagc ttagtgatga tgctcgtgct  1320
gattatcgga atttatctgc tgctgctatt cgtggagagt acgatacatg tgtactttat  1380
gccgatcagt tgaagcagag atgtgtggag cagttcaaag atggtgattt ggacattgaa  1440
caacttgctg ccgtggacgg catttgtgac ttcgtgtcga aggctattgg ggcttctgat  1500
cctgtccgca cataccatgt gaatctttcg atcttcactt caattcctga tttttgggca  1560
attgaccaac tattcccaat tgttcccatc cataagctag atgaaaggcc tggagtcaga  1620
ggaattttat cggacttgac ctgtgatagt gatgggaaga ttgataagtt cataggagga  1680
gagtcaagct tgccgctcca tgaattagga agtaatggtg gtggtagtgg tgatggtggg  1740
aaatactatc taggaatgtt tttgggtggg gcttatgagg aggcgctcgg gggactccat  1800
aacctatttg gcggacctag cgttttgcgt gtgtcgcaga gtgatagccc acacagcttc  1860
gctgtgacat gcgctgttcc tggtccatct tgtgctgacg ttctccgggc gatgcagcac  1920
gagcctgaac tcatgttcga gatgctcaag caccgtgctg atgaattcat gcacaacgac  1980
gacgaacaag aagaggataa ggggcttgca tttgcatctt tggcgagtag cttagctcag  2040
tcattcaaca atatgcctta ccttgttact gattcatctt gctgcattac tgctgccaat  2100
aacggtggct attactattg caatgatgag aacattgttg ggttgtcgc agaatctgct  2160
gcagctgaag aagagctttg gccttactgt gttgcttga                         2199

SEQ ID NO: 2           moltype = AA  length = 732
FEATURE                Location/Qualifiers
source                 1..732
                       mol_type = protein
                       organism = Nicotiana glauca
SEQUENCE: 2
MPALGCCVDA AVSPPPGYSF LWDSSLPAPG IFPSGVPPLT NTAAAATTTT HWSPAHSSAL  60
YCIDGWGAPY FTVNSSGDIS VKPHGTETLP HQEIDLLKVV KKASDPKNLG GLGLQFPLVV  120
RFPDILKNRL ESLQSVFDYA VQSQGYEAHY QGVYPVKCNQ DRFVVEDIVK FGSGFRFGLE  180
AGSKPELLLA MSCLCKGSRE GLLVCNGFKD AEYISLALVA RKLMLNTVIV LEQEEELDLV  240
IDISKKMAVR PVIGLRAKLR TKHSGHFGST SGEKGKFGLT TTQIVRVVKK LEESEMLDCL  300
QLLHFHIGSQ IPSTALLADG VGEAAQIYCE LVRLGAGMKY IDCGGGLGID YDGSKSCDSD  360
CSVGYGLQEY ASTVVQAVRF VCDRKNVKHP VICSESGRAI VSHHSVLIFE AVSSTSTRSQ  420
ELSSFYLQSF VEKLSDDARA DYRNLSAAAI RGEYDTCVLY ADQLKQRCVE QFKDGDLDIE  480
QLAAVDGICD FVSKAIGASD PVRTYHVNLS IFTSIPDFWA IDQLFPIVPI HKLDERPGVR  540
GILSDLTCDS DGKIDKFIGG ESSLPLHELG SNGGGSGDGG KYYLGMFLGG AYEEALGGLH  600
NLFGGPSVLR VSQSDSPHSF AVTCAVPGPS CADVLRAMQH EPELMFEMLK HRADEFMHND  660
DEQEEDKGLA FASLASSLAQ SFNNMPYLVT DSSCCITAAN NGGYYYCNDE NIVGVVAESA  720
AAEEELWPYC VA                                                      732

SEQ ID NO: 3           moltype = DNA  length = 2166
FEATURE                Location/Qualifiers
source                 1..2166
                       mol_type = genomic DNA
                       organism = Nicotiana glauca
SEQUENCE: 3
atgccggccc taggttgttg tgtagacgct gctgctgttt ctcctcctct tggctatgcc  60
ttctctcggg atagctctct tcccgcgccg gagttcttta cctccggcat acctccgaca  120
aattccgccg ccgcttccca ttggtctccg gatttgtcct ctgctttgta cggggtcgat  180
gggtgggggg ctccttattt ctctgttaac tctaacggag atatctccgt ccgaccacat  240
ggtatggaca ctctccctca ccaggaaatt gaccttctca aggtcgtgaa aaaggcctcc  300
gacccgaaaa attcaggtgg gcttggtctt cagctacctc ttgttgttcg cttccctgat  360
gtgctaaaaa accggttgga atctctgcag tcggcttttg atctcgcggt tcattcccag  420
ggctatgggg cccacttcca aggtgtttat cccgtgaaat gcaatcaaga ccggttcgtg  480
gtggaagata ttgtcaaatt cgggtcgtca ttccggttcg ggttggaagc cgggtctaaa  540
cccgagctcc tgttagccat gagctgtctc tgcaagggta gtgctgaggg ccttctcgtt  600
tgcaatggtt tcaaggacgc tgagtacatt tcgcttgctt tggttgcaag aaagctcatg  660
ttgaacactg taattgtgct tgaacaagag gaggagcttg accttgtgat tgatataagc  720
cgtaagatgg ctgttcggcc tgtaattgga cttcgggcta agctcaggac caagcattca  780
ggccattttg gatccacttc tggagaaaaa ggtaagtttg ggcttacaac tacccaaatt  840
gttcgtgtag tgaagaagct ggaagaatca ggaatgctgg attgccttca gttgctgcat  900
tttcacattg gatctcaaat cccttcaaca gcggtgcttg ctgacggtgt tggtgaggct  960
gctcagattt attgtgaatt agtccgtctt ggtgcgggta tgaagttcat tgatactgga  1020
ggtgggcttg gaattgatta tgatggtact aaatcatgcg attctgacgt ctctgttggc  1080
tatggcattc aagaatatgc ctccacagtt gtccaggagg ttcaatatgt atgcgaccgt  1140
aagggcgtga agcacccagt gatttgcagc gaaagtggca gggcaattgt ttctcatcac  1200
tcaattctga ttttcgaagc cgtgtcttct tctagtactc atgtttcttc ttcacatctg  1260
tcttctggtg tcctccaatc catggcggag acgctcaatg aagatgccct tgccgattac  1320
cgcaatttat ctgctgctgc agttcgtgga gagtacgaga catgtgtact ttactctgat  1380
cagttgaaac agagatgtgt ggatcagttt aaagaagggt ccttgggtat tgaacatctt  1440
gctgctgttg atagcatctg tgactttgta tcaaaggcta tgggggctgc tgatcctgtc  1500
cgcacttacc atgtgaatct gtcaattttc acttcaattc ctgatttttg ggcctttggt  1560
caattgtttc ctgttgttcc aatacaccgt ttagatgaaa agcctgcagt aaggggaata  1620
ttatcggact tgacttgtga cagtgatggg aaggttgata agttcattgg tggcgaatca  1680
agcttgccgc tacatgaatt gggaagtaac ggcgatggtg gtgggtacta tctggggatg  1740
tttttgggcg gggcttatga ggaggcgctc ggaggactcc acaacttgtt tggtggacca  1800
agtgtcgtgc gcgtggtgca gagcgatagc gctcacagct tcgccatgac tcgctccgtc  1860
cctggcccgt cctgtgcaga cgtgctccga gcgatgcagc acgagcccga gctcatgttc  1920
gagacactca agcaccgtgc agaggaattc ttggaacagg aagatgacaa agggctggcc  1980
gttgcatctt tggccagcag cttagctcag tccttccata acatgcctta ccttgtggcg  2040
cctgcatctt gctgcttcac tgcagcggct gctaacaatg gtggctataa ttactattac  2100
```

```
agtgatgaga atgcagcaga ttctgctaca ggggaggatg agatttggtc ctattgcact  2160
gcttga                                                             2166

SEQ ID NO: 4           moltype = AA  length = 721
FEATURE                Location/Qualifiers
source                 1..721
                       mol_type = protein
                       organism = Nicotiana glauca
SEQUENCE: 4
MPALGCCVDA AAVSPPLGYA FSRDSSLPAP EFFTSGIPPT NSAAASHWSP DLSSALYGVD  60
GWGAPYFSVN SNGDISVRPH GMDTLPHQEI DLLKVVKKAS DPKNSGGLGL QLPLVVRFPD  120
VLKNRLESLQ SAFDLAVHSQ GYGAHFQGVY PVKCNQDRFV VEDIVKFGSS FRFGLEAGSK  180
PELLLAMSCL CKGSAEGLLV CNGFKDAEYI SLALVARKLM LNTVIVLEQE EELDLVIDIS  240
RKMAVRPVIG LRAKLRTKHS GHFGSTSGEK GKFGLTTTQI VRVVKKLEES GMLDCLQLLH  300
FHIGSQIPST AVLADGVGEA AQIYCELVRL GAGMKFIDTG GGLGIDYDGT KSCDSDVSVG  360
YGIQEYASTV VQEVQYVCDR KGVKHPVICS ESGRAIVSHH SILIFEAVSS SSTHVSSSHL  420
SSGVLQSMAE TLNEDALADY RNLSAAAVRG EYETCVLYSD QLKQRCVDQF KEGSLGIEHL  480
AAVDSICDFV SKAMGAADPV RTYHVNLSIF TSIPDFWAFG QLFPVVPIHR LDEKPAVRGI  540
LSDLTCDSDG KVDKFIGGES SLPLHELGSN GDGGGYYLGM FLGGAYEEAL GGLHNLFGGP  600
SVVRVVQSDS AHSFAMTRSV PGPSCADVLR AMQHEPELMF ETLKHRAEEF LEQEDDKGLA  660
VASLASSLAQ SFHNMPYLVA PASCCFTAAA ANNGGYNYYY SDENAADSAT GEDEIWSYCT  720
A                                                                  721

SEQ ID NO: 5           moltype = DNA  length = 2199
FEATURE                Location/Qualifiers
source                 1..2199
                       mol_type = genomic DNA
                       organism = Nicotiana debneyi
SEQUENCE: 5
atgcctgcct taggttgttg tgtagacgct gctgtttctc ctcctcccgg ctattccttc  60
ctttgggata gctctcttcc tgcgccggag atttttccct ccggcgtacc tccgtcgaca  120
aacaccgccg ctgccaccac caccaccacc cactggtctc cggcgcactc atccgctctt  180
tattctattg acggatgggg tgctccgtat ttcaccgtta attcctccgg tgatatctcc  240
gttaagccac atggcacgga aactatgcct caccaggaaa tcgatctcct taaggtcgtg  300
aaaaaggcct ccgatccgaa aaatttgggc ggactcgggt tgcagtttcc gctcgttgtt  360
cggttccctg atattctgaa aaatcggttg gagtctcttc aatcagtttt tgattatgcg  420
gttcagtcac aaggttatga agctcactac caaggtgttt atcctgtgaa atgcaatcag  480
gacaggttcg ttgtagaaga tattgtcaaa ttcgggtcgg gtttccgctt cggtcttgaa  540
gccgggtcta aacctgagct cctcctagct atgagctgtc tctgcaaagg cagccgtgag  600
ggttttcttg tatgcaacgg gttcaaggat gcggagtaca tttcgcttgc tttggttgca  660
aggaagctca tgttgaatac agtaattgtg cttgaacaag aggaggagct tgatttggtg  720
attgacatca gcagaaaaat ggcggtccga cctgtgatcg ggcttcgggc taagctcagg  780
accaaacatt caggacattt cggatccact tcgggagaga aaggtaagtt tggacttacg  840
actacacaga tagttcgtgt ggtgaagaag ctagaagaat ccgaaatgct ggattgtctt  900
cagttgctgc attttcatat tggatctcag ataccttcga ccgctttgct tgctgatggc  960
gttggtgagg ctgcccagat ttactgtgaa ttagtccgcc tcggtgctgg catgaaatac  1020
gtcgattgtg gtggtggcct tggaattgac tatgatggta caaaatcttg tgattccgat  1080
tgttctgttg gatatggcct tcaggagtat gcatctacgg ttgttcaagc tgttcaattt  1140
gtttgtgacc ggaagaatgt gaaacatccg gtgatctgta gcgagagtgg tagagcaatt  1200
gtatctcatc actctgttct aatatttgag gctgtttctt caactacaac acgctcacaa  1260
gagttatctt ctgttgatct ccagtcattt gtggagaagc ttaatgatga tggtcgtgct  1320
gattatcgga atttatctgc tgctgctatt cgtggagagt acgatacatg tgtactttat  1380
gccgatcagt tgaaacagag atgtgtggag cagttcaaag atggtgattt ggacattgaa  1440
caacttgctg ccgtggatgg catttgtgac ttcgtgtcga aggctattgg ggcttctgat  1500
cctgtccgca cataccatgt taatctttcg atcttcactt caattcctga tttttgggca  1560
attgaccaac tattcccaat tgttcccatc cataagctag atgaacggcc tggtgtccga  1620
ggaattttat cggacttgac ctgtgatagt gatgggaaga ttgataagtt cattggaggg  1680
gagtcaagtt tgccgctcca tgaattagga agcaatggtg gtggtagtgg tgatggtggg  1740
aaatactatc tgggaatgtt tttgggtggg gcttatgagg aggcgctcgg gggactccat  1800
aacctatttg gcggacccag cgttttgcgt gtgtcacaga gcaatagccc gcacagcttc  1860
gctgtgacat ccgctgttcc tggtccgtct tgtgctgatg ttctccgggc gatgcagcac  1920
gagcctgaac tcatgttcga gacactcaag caccgcgctg aagaattcgt gcacgaccac  1980
gacgaacaag aagaagataa ggggcttgca cttgcctctt tggccagcag cttagctcag  2040
tcattcaaca atatgcctta cctttctact aattcatctt gctgccttac tgctgccaat  2100
aacagtggct attactattg caatgatgag aacattgttg gagttggcgc agaatctgct  2160
gcagctgaag aagagctttg gccttactgt gttgcttga                         2199

SEQ ID NO: 6           moltype = AA  length = 732
FEATURE                Location/Qualifiers
source                 1..732
                       mol_type = protein
                       organism = Nicotiana debneyi
SEQUENCE: 6
MPALGCCVDA AVSPPPGYSF LWDSSLPAPE IFPSGVPPST NTAAATTTTT HWSPAHSSAL  60
YSIDGWGAPY FTVNSSGDIS VKPHGTETMP HQEIDLLKVV KKASDPKNLG GLGLQFPLVV  120
RFPDILKNRL ESLQSVFDYA VQSQGYEAHY QGVYPVKCNQ DRFVVEDIVK FGSGFRFGLE  180
AGSKPELLLA MSCLCKGSRE GFLVCNGFKD AEYISLALVA RKLMLNTVIV LEQEEELDLV  240
IDISRKMAVR PVIGLRAKLR TKHSGHFGST SGEKGKFGLT TTQIVRVVKK LEESEMLDCL  300
QLLHFHIGSQ IPSTALLADG VGEAAQIYCE LVRLGAGMKY VDCGGGLGID YDGTKSCDSD  360
```

```
CSVGYGLQEY ASTVVQAVQF VCDRKNVKHP VICSESGRAI VSHHSVLIFE AVSSTTTRSQ  420
ELSSVDLQSF VEKLNDDGRA DYRNLSAAAI RGEYDTCVLY ADQLKQRCVE QFKDGDLDIE  480
QLAAVDGICD FVSKAIGASD PVRTYHVNLS IFTSIPDFWA IDQLFPIVPI HKLDERPGVR  540
GILSDLTCDS DGKIDKFIGG ESSLPLHELG SNGGGSGDGG KYYLGMFLGG AYEEALGGLH  600
NLFGGPSVLR VSQSNSPHSF AVTSAVPGPS CADVLRAMQH EPELMFETLK HRAEEFVHDH  660
DEQEEDKGLA LASLASSLAQ SFNNMPYLST NSSCCLTAAN NSGYYYCNDE NIVGVGAESA  720
AAEEELWPYC VA                                                      732

SEQ ID NO: 7            moltype = DNA  length = 27
FEATURE                 Location/Qualifiers
source                  1..27
                        mol_type = other DNA
                        organism = Nicotiana glauca
SEQUENCE: 7
agaatctgaa atgttggatt gtcttca                                      27

SEQ ID NO: 8            moltype = DNA  length = 27
FEATURE                 Location/Qualifiers
source                  1..27
                        mol_type = other DNA
                        organism = Nicotiana glauca
SEQUENCE: 8
tgaatcacac gattttgatc catcata                                      27

SEQ ID NO: 9            moltype = DNA  length = 26
FEATURE                 Location/Qualifiers
source                  1..26
                        mol_type = other DNA
                        organism = Nicotiana glauca
SEQUENCE: 9
gggctcctta tttctctgtt aactct                                       26

SEQ ID NO: 10           moltype = DNA  length = 25
FEATURE                 Location/Qualifiers
source                  1..25
                        mol_type = other DNA
                        organism = Nicotiana glauca
SEQUENCE: 10
gatcaaaagc cgactgcaga gattc                                        25

SEQ ID NO: 11           moltype = DNA  length = 22
FEATURE                 Location/Qualifiers
source                  1..22
                        mol_type = other DNA
                        organism = Nicotiana debneyi
SEQUENCE: 11
tgtgtcacag agcaatagcc cg                                           22

SEQ ID NO: 12           moltype = DNA  length = 23
FEATURE                 Location/Qualifiers
source                  1..23
                        mol_type = other DNA
                        organism = Nicotiana debneyi
SEQUENCE: 12
gcaagtgcaa gcccottatc ttc                                          23

SEQ ID NO: 13           moltype = DNA  length = 2202
FEATURE                 Location/Qualifiers
source                  1..2202
                        mol_type = genomic DNA
                        organism = Nicotiana tabacum
SEQUENCE: 13
atgcctgcct taggttgttg tgtagacgct gctgtttctc ctcctcccgg ctattccttc  60
ctttgggata gttctcttcc cgcgccggag atttttccct ccggcgtacc tccgtcgaca  120
aacaccgccg ttgccaccac caccaccacc cattggtctc cggcgcactc atccgctctt  180
tattctattg acggatgggg cgctccgtat ttcaccgtta attcctccgg tgatatctcc  240
gttaagccac atggtacgga tactctgcct caccaggaaa tcgatctcct taaggtcgtg  300
aaaaaggcct ccgacccgaa aaatttgggc ggactcgggt tgcagtttcc gctcgttgtt  360
cggttccctg atattctgaa aaaccggttg gagtctcttc aatccgtttt tgattatgcg  420
gttcagtcac aaggttatga agctcactac caaggtgttt atcctgtgaa atgcaaccag  480
gacaggttcg ttgttgaaga tattgtcaaa ttcggatcgg gtttccggtt cggtctcgaa  540
gctgggtcta aacctgagct cctcctagct atgagctgtc tctgcaaagg cagtcatgag  600
ggtcttcttg tgtgcaacgg gttcaaggat gctgagtaca tttcgcttgc tttggttgca  660
aggaagctca tgttgaatac agtaattgtc cttgaacaag aggaggagct tgatttggtg  720
attgacatca gcaagaaaat ggcggtccgg cctgtgatcg ggcttcgggc taagctcagg  780
accaaacatt cgggtcattt cggatccact tctggagaga aaggtaaatt tgggctcacg  840
acaacacaga ttgttcgtgt ggtgaagaag ctagaagaat ccggaatgct ggattgtctt  900
cagttgctgc attttcatat cggatctcaa atcccttcga cggctttgct tgctgatggc  960
gttggtgagg ctgcccagat ttactgtgaa ttagtccgcc tcggtgctgg catgaaatac  1020
```

```
attgattgtg gtggtggcct tggaattgac tatgatggta caaaatcatg tgattccgat  1080
tgttctgttg gatatggcct tcaggaatat gcatctacgg ttgttcaagc tgttcgattt  1140
gtttgtgacc ggaagaacgt gaaacatccg gtgatctgta gcgagagtgg gagagcaatt  1200
gtatctcatc actctgttct gatatttgag gctgtgtctt caactacaac acgctcacaa  1260
gagttatctt ctgttgatct ccagtcattt gtggagaagc tcaatgatga tgctcgtgct  1320
gattatcgga atttatctgc tgctgctatt cgtggagagt acgatacgtg tgtactttat  1380
gctgatcagt tgaaacagag atgtgtggag cagttcaaag atggtgattt ggacattgaa  1440
caacttgctg cagtagatgg catttgtgat ttcgtgtcga aggctattgg ggcttctgat  1500
cctgtccgca cataccatgt gaatctttcg atcttcactt cagttcctga tttttgggca  1560
attgaccaac tattcccaat tgttcccatc cataagctag atgaacggcc tgtagttcga  1620
ggaattttat cggacttgac ctgtgatagt gatgggaaga ttgataagtt cattggagga  1680
gagtcaagct tgccgctcca tgaattagga agtaatggtg gtggtggtgg tgatggtgga  1740
aaatattatc taggaatgtt tttgggtggg gcttatgagg aggcgcttgg gggactccat  1800
aacctatttg gcggacccag cgttttgcgt gtgtcacaga gcgatagccc acacagcttc  1860
gccgtgacat gtgctgttcc tggtccgtcc tgtgctgacg ttctccgggc gatgcagcac  1920
gagcctgaac tcatgttcga gacgctcaag caccgcgctg aagaattcgt gcacaatgac  1980
gacgaacaag aagaagataa agggcttgca tttgcatctt tggccagcag cttagctcag  2040
tcattcaaca atatgcctta ccttgttact aattcatctt gctgccttac tgctgctgcc  2100
aataacggtg gctattacta ttgcaatgat gagaacattg ttggagttgg cgcagaatct  2160
gctgcagctg aagaagagct ttggccttac tgtgttgctt ga                    2202

SEQ ID NO: 14           moltype = AA  length = 733
FEATURE                 Location/Qualifiers
source                  1..733
                        mol_type = protein
                        organism = Nicotiana tabacum
SEQUENCE: 14
MPALGCCVDA AVSPPPGYSF LWDSSLPAPE IFPSGVPPST NTAVATTTTT HWSPAHSSAL  60
YSIDGWGAPY FTVNSSGDIS VKPHGTDTLP HQEIDLLKVV KKASDPKNLG GLGLQFPLVV  120
RFPDILKNRL ESLQSVFDYA VQSQGYEAHY QGVYPVKCNQ DRFVVEDIVK FGSGFRFGLE  180
AGSKPELLLA MSCLCKGSHE GLLVCNGFKD AEYISLALVA RKLMLNTVIV LEQEEELDLV  240
IDISKKMAVR PVIGLRAKLR TKHSGHFGST SGEKGKFGLT TTQIVRVVKK LEESGMLDCL  300
QLLHFHIGSQ IPSTALLADG VGEAAQIYCE LVRLGAGMKY IDCGGGLGID YDGTKSCDSD  360
CSVGYGLQEY ASTVVQAVRF VCDRKNVKHP VICSESGRAI VSHHSVLIFE AVSSTTTRSQ  420
ELSSVDLQSF VEKLNDDARA DYRNLSAAAI RGEYDTCVLY ADQLKQRCVE QFKDGDLDIE  480
QLAAVDGICD FVSKAIGASD PVRTYHVNLS IFTSVPDFWA IDQLFPIVPI HKLDERPVVR  540
GILSDLTCDS DGKIDKFIGG ESSLPLHELG SNGGGGGDGG KYYLGMFLGG AYEEALGGLH  600
NLFGGPSVLR VSQSDSPHSF AVTCAVPGPS CADVLRAMQH EPELMFETLK HRAEEFVHND  660
DEQEEDKGLA FASLASSLAQ SFNNMPYLVT NSSCCLTAAA NNGGYYYCND ENIVGVGAES  720
AAAEEELWPY CVA                                                     733

SEQ ID NO: 15           moltype = DNA  length = 2193
FEATURE                 Location/Qualifiers
source                  1..2193
                        mol_type = genomic DNA
                        organism = Nicotiana tabacum
SEQUENCE: 15
atgcctgcct taggttgttg tgtagacgct gctgtttctc ctcctcccgg ctattccttc  60
ctttgggata gctctcttcc cgcgccggag atttttccct ccggcgtacc tctgtcgaca  120
aacaccgccg ccactaccac gaccaccacc cattggtctc cggcgcactc atccgctctt  180
tattctattg acggatgggg tgctccgtat ttcaccgtta attcctccgg tgatatctcc  240
gttaagccac atggtacgga aactctgcct caccaggaaa ttgatctcct taaggtcgtg  300
aaaaaagcat ccgacccgaa aaattcgggt ggactcgggt tgcagtttcc gctcgttgtt  360
cggttccctg atattctgaa aaaccggttg gagtctctac aatcggcttt tgattatgcg  420
gttcagtcac aaggttatga ggctcactac caaggtgttt atcctgttaa atgcaatcag  480
gacaggttcg ttgttgaaga tattgtcaaa ttcgggtcgg gtttccgatt cggtctcgaa  540
gccggctcga aacccgagct cctcctagct atgagctgtc tctgcaaggg cagtcgcgag  600
ggtcttcttg tatgcaacgg gttcaaagat gctgactaca tttcgcttgc tttggttgca  660
aggaagctca tgttgaatac agtaattgtg cttgaacaag aggaggagct tgatttggtg  720
attgacatca gcagaaaaat ggctgtccgg cctttgatcg ggcttcgggc taagctcagg  780
accaaacatt ccggccattt cggatccact tcaggagaga aaggtaagtt tgggcttacg  840
acaacacaga tcgttcgtgt ggtgaagaag ctagaagaat ccggaatgtt ggattgtctt  900
cagctgctgc atttcatat tggatctcag atcccttcga cggctttgct tgctgatggc  960
gtgggtgagg ccgctcagat ttactgtgaa ttagtccgcc ttggtgctgg catgaaatac  1020
attgattgtg gtggtggcct tggaattgac tatgatggta caaaatcgtg tgattccgat  1080
tgttcagttg gatatggcct tcaggagtat gcatctacag ttgttcaagc tgttcgattt  1140
gtttgtgatc ggaagaatgt gaaacatccg gtgatttgta gcgagagtgg gagagcaatt  1200
gtatctcatc actctgtttt gatatttgag gctgtttctt caactacaac acgctcacaa  1260
gagttatctt ctgttgatct ccagtcattt gtggagaagc ttaatgatga tgctcgtgct  1320
gattatcgga atttatctgc tgctgctatt cgtggagagt acgatacgtg tgtactttat  1380
gccgatcagt tgaaacagag atgtgtggag cagttcaaag atggtaattt ggacattgaa  1440
cagcttgctg ccgtagatgg tatttgtgac ttcgtgtcga aggctattgg ggcttctgat  1500
cctgtccgca catatcatgt gaatctttcg atcttcactt caattcccga tttttgggca  1560
attgaccaac tattcccaat tgttcccatc cataagctag atgaacggcc tggagtccga  1620
ggaatattat cggacttgac ctgtgatagt gatgggaaga ttgataagtt cattggagga  1680
gagtcaagct tgccgctcca tgaattagga agtaatggtg gtggtgatgg tgggaaatat  1740
tatctgggaa tgtttttggg tggggcttat gaggaggcgc tcgggggcct ccataaccta  1800
tttggcggac ccagtgtttt gcgcgtgtca cagagcgata gcccacacag cttcgctgtg  1860
acatgcgctg ttcctggtcc gtcttgtgct gacgttctcc gggcgatgca gcacgagcct  1920
```

```
gaactcatgt tcgagacgct caagcaccgt gctgaagaat tcgtgcataa tgacgacgaa  1980
caagaagaag ataaagggct tgcatttgca tctttagcca gcagcttagc tcagtcattc  2040
aacaatatgc cttaccttgt taccaattca tcttgctgcc ttactgctac caataacggt  2100
ggctattact attgcaatga tgagaacatt gttggggttg gcgcagaatc tgctgcagct  2160
gaggaagagc tttggcctta ctgtgttgct tga                                2193

SEQ ID NO: 16          moltype = AA  length = 730
FEATURE                Location/Qualifiers
source                 1..730
                       mol_type = protein
                       organism = Nicotiana tabacum
SEQUENCE: 16
MPALGCCVDA AVSPPPGYSF LWDSSLPAPE IFPSGVPLST NTAATTTTTT HWSPAHSSAL  60
YSIDGWGAPY FTVNSSGDIS VKPHGTETLP HQEIDLLKVV KKASDPKNSG GLGLQFPLVV  120
RFPDILKNRL ESLQSAFDYA VQSQGYEAHY QGVYPVKCNQ DRFVVEDIVK FGSGFRFGLE  180
AGSKPELLLA MSCLCKGSRE GLLVCNGFKD ADYISLALVA RKLMLNTVIV LEQEEELDLV  240
IDISRKMAVR PLIGLRAKLR TKHSGHFGST SGEKGKFGLT TTQIVRVVKK LEESGMLDCL  300
QLLHFHIGSQ IPSTALLADG VGEAAQIYCE LVRLGAGMKY IDCGGGLGID YDGTKSCDSD  360
CSVGYGLQEY ASTVVQAVRF VCDRKNVKHP VICSESGRAI VSHHSVLIFE AVSSTTTRSQ  420
ELSSVDLQSF VEKLNDDARA DYRNLSAAAI RGEYDTCVLY ADQLKQRCVE QFKDGNLDIE  480
QLAAVDGICD FVSKAIGASD PVRTYHVNLS IFTSIPDFWA IDQLFPIVPI HKLDERPGVR  540
GILSDLTCDS DGKIDKFIGG ESSLPLHELG SNGGGDGGKY YLGMFLGGAY EEALGGLHNL  600
FGGPSVLRVS QSDSPHSFAV TCAVPGPSCA DVLRAMQHEP ELMFETLKHR AEEFVHNDDE  660
QEEDKGLAFA SLASSLAQSF NNMPYLVTNS SCCLTATNNG GYYYCNDENI VGVGAESAAA  720
EEELWPYCVA                                                          730

SEQ ID NO: 17          moltype = DNA  length = 2166
FEATURE                Location/Qualifiers
source                 1..2166
                       mol_type = genomic DNA
                       organism = Nicotiana tabacum
SEQUENCE: 17
atgccggccc taggttgttg tgtagatgct gctgttgttt cccctcctct cagctatgcc  60
ttctctcggg atagctctct tcccgcgccg gagttctttg cctccggcgt acctccgaca  120
aattctgccg ctgcttccca ttggtctccg gatttgtcgt ctgctttata cggggtcgat  180
gggtggggag ctccttattt ctctgttaac tctaatggag atatctccgt ccgaccacac  240
ggtacggaca ctctccctca ccaggaaatt gaccttctca aggtcgtgaa aaaggcctcc  300
gacccgaaaa attcaggtgg gcttgggctt cagctgcctc ttgttgttcg cttccctgat  360
gtgttgaaaa accggttgga atctctgcaa tcggcttttg atctcgcggt tcattcccag  420
ggctatgggg cccactacca aggtgtttat cccgtgaaat gcaatcaaga caggttcgtg  480
gtggaagata tcgtgaaatt cgggtcgcca ttccggttcg ggttggaagc cgggtctaaa  540
cccgagctcc tgttagccat gagctgtctc tgcaagggca gtgctgaggg ccttctcgtt  600
tgcaatggtt tcaaggacgc tgagtacatt tcgcttgctt tggttgcaag aaagctcatg  660
ttaaacactg taattgtgct tgaacaagag gaggagcttg accttgtgat tgatataagc  720
cataagatgg ctgttcggcc tgtaattgga cttcgggcta agctcaggac caagcattca  780
ggccattttg gatccacttc tggagaaaaa ggtaagtttg ggcttacaac gacccaaatt  840
gttcgtgtgg tgaagaagct agaagaatcc ggaatgctgg attgccttca gttgctgcat  900
tttcacattg gatctcagat cccttctacg ggggttgctag ctgatggagt tggtgaggcc  960
gctcagattt attgtgaatt agtccgtctt ggagcgggta tgaagttcat tgatattgga  1020
ggtgggcttg gaattgatta tgatggtact aaatcatgcg attctgatgt ctctgttggc  1080
tatggcattc aagaatatgc ctccgcagtt gttcaggcgg ttcaatatgt atgcgaccgt  1140
aagggtgtga aacacccagt gatctgcagc gaaagtggca gggcaattgt ttctcatcac  1200
tcaattctga ttttcgaagc cgtgtctgct tctagtactc atgtttcttc ttcacatctg  1260
tcttctggtg gcctccaatc catggcggag acgctcaacg aagatgccct tgctgattac  1320
cgcaatttat ctgctgctgc agttcgtgga gagtatgaga catgtgtact ttactctgat  1380
cagttgaaac agagatgtgt ggagcagttt aaagaagggt ccttgggtat tgaacatctt  1440
gctgctgttg atagcatctg tgactttgta tcaaaggcta tgggggctgc tgatcctgtc  1500
cgcacttacc atgtgaatct gtcaattttc acttcaattc ctgatttttg ggcctttggt  1560
caattgtttc cgattgttcc aattcaccgc ttagatgaaa agcctgcagt gaggggaata  1620
ttatcggact taacttgtga cagtgatggg aaggttgata agttcattgg tggcgaatca  1680
agcttgccgc tacatgaatt gggaagtaat ggcgatggtg gtggttatta tctggggatg  1740
tttttgggtg gggcttatga ggaggcgctc ggaggactcc acaacctgtt tggtggacca  1800
agtgtcgtgc gcgtggtgca gagcgatagc gctcacagct ttgccatgac tcgctccgtc  1860
cctggcccgt cttgcgctga tgtgctccga gcgatgcagc acgagcccga gctcatgttc  1920
gagactctca agcaccgtgc ggaggaattc ttggaacaag aagatgacaa agggctggct  1980
gttgaatctt tggccagcag cgtagctcag tccttccata acatgcctta ccttgtggcg  2040
ccttcatctt gccgcttcac tgctgctact gataacaatg gtggctataa ttactattac  2100
agtgatgaga atgcagcaga ttctgctaca ggggaggatg agatttggtc ctattgcact  2160
gcttga                                                              2166

SEQ ID NO: 18          moltype = AA  length = 721
FEATURE                Location/Qualifiers
source                 1..721
                       mol_type = protein
                       organism = Nicotiana tabacum
SEQUENCE: 18
MPALGCCVDA AVVSPPLSYA FSRDSSLPAP EFFASGVPPT NSAAASHWSP DLSSALYGVD  60
GWGAPYFSVN SNGDISVRPH GTDTLPHQEI DLLKVVKKAS DPKNSGGLGL QLPLVVRFPD  120
VLKNRLESLQ SAFDLAVHSQ GYGAHYQGVY PVKCNQDRFV VEDIVKFGSP FRFGLEAGSK  180
```

```
PELLLAMSCL CKGSAEGLLV CNGFKDAEYI SLALVARKLM LNTVIVLEQE EELDLVIDIS  240
HKMAVRPVIG LRAKLRTKHS GHFGSTSGEK GKFGLTTTQI VRVVKKLEES GMLDCLQLLH  300
FHIGSQIPST GLLADGVGEA AQIYCELVRL GAGMKFIDIG GGLGIDYDGT KSCDSDVSVG  360
YGIQEYASAV VQAVQYVCDR KGVKHPVICS ESGRAIVSHH SILIFEAVSA SSTHVSSSHL  420
SSGGLQSMAE TLNEDALADY RNLSAAAVRG EYETCVLYSD QLKQRCVEQF KEGSLGIEHL  480
AAVDSICDFV SKAMGAADPV RTYHVNLSIF TSIPDFWAFG QLFPIVPIHR LDEKPAVRGI  540
LSDLTCDSDG KVDKFIGGES SLPLHELGSN GDGGGYYLGM FLGGAYEEAL GGLHNLFGGP  600
SVVRVVQSDS AHSFAMTRSV PGPSCADVLR AMQHEPELMF ETLKHRAEEF LEQEDDKGLA  660
VESLASSVAQ SFHNMPYLVA PSSCRFTAAT DNNGGYNYYY SDENAADSAT GEDEIWSYCT  720
A                                                                  721

SEQ ID NO: 19          moltype = DNA  length = 2163
FEATURE                Location/Qualifiers
source                 1..2163
                       mol_type = genomic DNA
                       organism = Nicotiana tabacum
SEQUENCE: 19
atgccggccc taggttgttg cgtagacgct actgtttccc ctcctctcgg ctatgccttc  60
tctcgggata gctctcttcc cgcgccggag ttctttacct ccggcgtacc tcctacaaac  120
tccgccgccg gttcccattg gtctccggat ctgtcctctg ctttgtacgg ggtcgatggg  180
tggggagctc cttatttctc cgttaactct aacggagata tctccgtccg accacatggt  240
acggacacac tcccccacca ggaaattgac cttctcaagg tcgtgaaaaa ggcctccgac  300
ccgaaaaatt caggggggct cggcttcag ctgcctcttg ttgttcgctt ccctgatgtg  360
ctaaaaaacc ggttggaatc tctgcaatcg gcttttgatc tcgctgttca ttcccagggc  420
tatggggccc actaccaagg tgtttatccc gtgaaatgca atcaagacag gttcgtggtg  480
gaagatattg tcaaattcgg gtcgtcattc cggttcgggt tggaagctgg gtctaaaccc  540
gagctcctgt tagccatgag ctgtctctgc aggggcagtg ctgagggcct tctcgtttgc  600
aatggtttca aggacgctga gtacatttcg cttgctttgg ttgcaagaaa gctcatgtta  660
aacactgtaa ttgttcttga acaagaggag gagcttgacc ttgtgattga tataagccgt  720
aagatggctg ttcggcccgt aattggactt cgggctaagc tcaggaccaa gcattcaggc  780
cattttggat ccacttctgg agaaaaaggt aagtttgggc ttacaacgac ccaaattgtt  840
cgtgtagtga agaagctgga agaatccgga atgctggatt gccttcagtt gctgcatttt  900
cacattggat ctcagatccc ttcaacggcg ttgcttgctg atggtgttgg tgaggctgct  960
cagatttatt gtgaattaat ccgtcttggt gcgggtatga agttcattga tactggaggt  1020
gggctcggaa ttgattatga tggtactaaa tcatgtgatt cagatgtctc tgttggctat  1080
ggcattcaag aatacgcctc cacagttgtc caggcggttc aatatgtttg cgaccgtaag  1140
ggcgtgaagc acccagtgat ttgcagcgaa agtggcaggg caattgtttc tcatcactca  1200
attctgattt tcgaagccgt gtctgcttct agcactcatg tttcttcttc acatctgtct  1260
tctggtggcc tccaatccat ggcggagacg ctcaatgaag atgcccttgc tgattaccgc  1320
aatttatctg ctgctgcagt tcgtggagag tacgagacgt gtgtacttta ctctgatcag  1380
ttgaaacaga gatgtgtgga tcagtttaaa gaagggtcct tgggtattga acatcttgct  1440
gctgttgata gcatctgtga ctttgtatca aaggctatgg gggctgctga tcctatccgc  1500
acttaccatg tgaatctgtc aattttcact tcaattcctg atttttgggc ctttggtcaa  1560
ttgtttccga ttgttccaat acaccgttta gatgaaaagc ctgcagtaag gggaatatta  1620
tcggacttga cttgtgacag tgatgggaag gttgataagt tcattggtgg cgaatcaagc  1680
ttgcagctgc atgaattggg aagtaatggc gatggtggtg ggtattatct ggggatgttt  1740
ttgggtgggg cttatgagga ggcgctcgga ggactccaca acctgtttgg tggaccaagc  1800
gtggtgcgcg tggtgcagag cgatagcgct cacagcttcg ccatgtctcg ctccgtccct  1860
ggcccgtcct gcgcggacgt gctccgagcg atgcagcacg agcccgagct catgttcgag  1920
actctcaagc accgtgcgga ggaattcttg gaacaagaag aagacaaagg gctggccatt  1980
gcatctttgg ccagcagctt agctcagtcc ttccataaca tgccttacct tgtggcgcct  2040
gcatcttgct gcttcactgc agttactgct aacaacggtg gctataacta ctattacagt  2100
gatgagaatg cagcagattc tgctacaggg gaggatgaga tttggtccta ttgcactgct  2160
tga                                                                2163

SEQ ID NO: 20          moltype = AA  length = 720
FEATURE                Location/Qualifiers
source                 1..720
                       mol_type = protein
                       organism = Nicotiana tabacum
SEQUENCE: 20
MPALGCCVDA TVSPPLGYAF SRDSSLPAPE FFTSGVPPTN SAAGSHWSPD LSSALYGVDG  60
WGAPYFSVNS NGDISVRPHG TDTLPHQEID LLKVVKKASD PKNSGGLGLQ LPLVVRFPDV  120
LKNRLESLQS AFDLAVHSQG YGAHYQGVYP VKCNQDRFVV EDIVKFGSSF RFGLEAGSKP  180
ELLLAMSCLC RGSAEGLLVC NGFKDAEYIS LALVARKLML NTVIVLEQEE ELDLVIDISR  240
KMAVRPVIGL RAKLRTKHSG HFGSTSGEKG KFGLTTTQIV RVVKKLEESG MLDCLQLLHF  300
HIGSQIPSTA LLADGVGEAA QIYCELIRLG AGMKFIDTGG GLGIDYDGTK SCDSDVSVGY  360
GIQEYASTVV QAVQYVCDRK GVKHPVICSE SGRAIVSHHS ILIFEAVSAS STHVSSSHLS  420
SGGLQSMAET LNEDALADYR NLSAAAVRGE YETCVLYSDQ LKQRCVDQFK EGSLGIEHLA  480
AVDSICDFVS KAMGAADPIR TYHVNLSIFT SIPDFWAFGQ LFPIVPIHRL DEKPAVRGIL  540
SDLTCDSDGK VDKFIGGESS LQLHELGSNG DGGGYYLGMF LGGAYEEALG GLHNLFGGPS  600
VVRVVQSDSA HSFAMSRSVP GPSCADVLRA MQHEPELMFE TLKHRAEEFL EQEEDKGLAI  660
ASLASSLAQS FHNMPYLVAP ASCCFTAVTA NNGGYNYYYS DENAADSATG EDEIWSYCTA  720

SEQ ID NO: 21          moltype = AA  length = 29
FEATURE                Location/Qualifiers
source                 1..29
                       mol_type = protein
                       organism = Nicotiana debneyi
```

-continued

```
SEQUENCE: 21
IGLRAKLRTK HSGHFGSTSG EKGKFGLTT                                    29
```